US011208430B2

(12) United States Patent
Stetsenko et al.

(10) Patent No.: US 11,208,430 B2
(45) Date of Patent: Dec. 28, 2021

(54) MODIFIED OLIGONUCLEOTIDES AND METHODS FOR THEIR SYNTHESIS

(71) Applicant: NooGen LLC, Novosibirsk (RU)

(72) Inventors: Dmitry Stetsenko, Hampshire (GB); Maxim Kupryushkin, Kemerovo (RU); Dmitrii Pyshnyi, Novosibirsk (RU)

(73) Assignee: NOOGEN LLC, Novosibirsk (RU)

( * ) Notice: Subject to any disclaimer, the term of this patent is extended or adjusted under 35 U.S.C. 154(b) by 59 days.

(21) Appl. No.: 15/329,764

(22) PCT Filed: Aug. 28, 2014

(86) PCT No.: PCT/RU2014/000647
§ 371 (c)(1),
(2) Date: Jan. 27, 2017

(87) PCT Pub. No.: WO2016/028187
PCT Pub. Date: Feb. 25, 2016

(65) Prior Publication Data
US 2017/0362270 A1    Dec. 21, 2017

(30) Foreign Application Priority Data
Aug. 22, 2014   (RU) .............................. 2014134380

(51) Int. Cl.
| C07H 21/04 | (2006.01) |
| C07H 21/02 | (2006.01) |
| C07H 19/067 | (2006.01) |
| C07H 19/167 | (2006.01) |
| C12N 15/11 | (2006.01) |

(52) U.S. Cl.
CPC ........... C07H 21/04 (2013.01); C07H 19/067 (2013.01); C07H 19/167 (2013.01); C07H 21/02 (2013.01); C12N 15/11 (2013.01); *C12N 2310/314* (2013.01); *C12N 2310/315* (2013.01); *C12N 2310/3517* (2013.01); *C12N 2330/30* (2013.01)

(58) Field of Classification Search
CPC .... C07H 19/067; C07H 19/167; C07H 21/02; C07H 21/04; C12N 15/11; C12N 2330/30; C12N 2310/314; C12N 2310/315; C12N 2310/3517
See application file for complete search history.

(56) References Cited

U.S. PATENT DOCUMENTS

| 3,634,555 A | 1/1972 | Sherif |
| 3,769,406 A | 10/1973 | Anatol et al. |
| 4,154,826 A | 5/1979 | Rathgeb |
| 2020/0157545 A1 | 5/2020 | Vargeese et al. |
| 2020/0362337 A1 | 11/2020 | Dodart et al. |
| 2020/0369709 A1 | 11/2020 | Kupryushkin et al. |

FOREIGN PATENT DOCUMENTS

| RU | 2115658 C1 | 7/1998 |
| WO | WO-89/09221 A1 | 10/1989 |
| WO | WO-1989/09221 A1 | 10/1989 |
| WO | WO-94/02498 A1 | 2/1994 |
| WO | WO-01/15737 A2 | 3/2001 |
| WO | WO-03/002587 A2 | 1/2003 |
| WO | WO-2003/002587 A2 | 1/2003 |
| WO | WO-2006/023880 A2 | 3/2006 |
| WO | WO-2007/059816 A1 | 5/2007 |
| WO | WO-2008/128686 A1 | 10/2008 |
| WO | WO-2008/141799 A1 | 11/2008 |
| WO | WO-2009/147368 A1 | 12/2009 |
| WO | WO-2010/064146 A2 | 6/2010 |
| WO | WO-2011/005761 A1 | 1/2011 |
| WO | WO-2013/012758 A1 | 1/2013 |
| WO | WO-2014/010250 A1 | 1/2014 |
| WO | WO-2014/012081 A2 | 1/2014 |
| WO | WO-2015/107425 A2 | 7/2015 |
| WO | WO-2018/056871 A1 | 3/2018 |
| WO | WO-201 8/156056 A1 | 8/2018 |
| WO | WO-201 8/223056 A1 | 12/2018 |
| WO | WO-2019/032607 A1 | 2/2019 |
| WO | WO-2019/112485 A1 | 6/2019 |

(Continued)

OTHER PUBLICATIONS

Pon et al., Hydroquinone-O-O'-diacetic acid (Q-linker) as a Replacement for Succinyl and Oxalyl Linker Arms in Solid Phase Oligonucleotide Synthesis, Nucleic Acids Research, 25(18), 3629-3635 (1997); copy supplied by applicant and is in the instant record.*
International Preliminary Report on Patentability (PCT/IB/373) dated Feb. 28, 2017 in International application No. PCT/RU2014/000647 (7 pages).
Belikova et al., "Synthesis of Ribonucleosides and Diribonucleoside Phosphates Containing 2-Chloroethylamine and Nitrogen Mustard Residues," Tetrahedron Letters, No. 37, 1967, pp. 3557-3562.
Jager et al., "Oligonucleotide N-Alkylphosphoramidates: Synthesis and Binding to Polynucleotides," Biochemistry, vol. 27, 1998, pp. 7237-7246.
Kurata et al., "Characterization of high molecular weight impurities in synthetic phosphorothioate oligonucleotides," Bioorganic & Medicinal Chemistry Letters, vol. 16, pp. 607-614, 2006.

(Continued)

*Primary Examiner* — Lawrence E Crane

(74) *Attorney, Agent, or Firm* — Muncy, Geissler, Olds & Lowe, P.C.

(57) ABSTRACT

The present invention is directed to modified oligonucleotides having the following Formula (I)

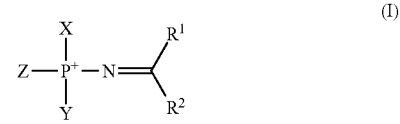

Figure 1:
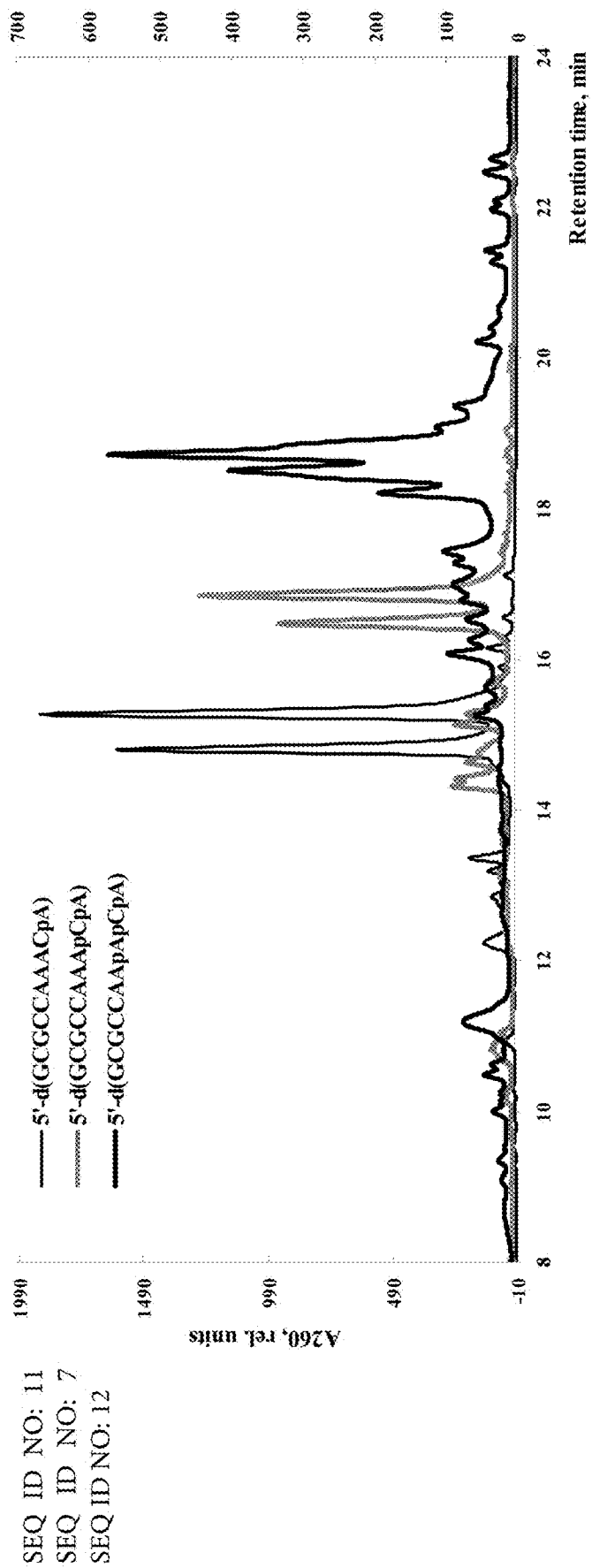

wherein one or more of phosphate groups are substituted at phosphorus, and methods for their synthesis. The modified oligonucleotides are useful for diagnostic applications involving sequence specific recognition of a nucleic acid and for use in a method of medical treatment.

26 Claims, 8 Drawing Sheets

Specification includes a Sequence Listing.

(56) References Cited

FOREIGN PATENT DOCUMENTS

| WO | WO-2019/200185 A1 | 10/2019 |
| WO | WO-2019/217784 A1 | 11/2019 |
| WO | WO-2020/118243 A1 | 6/2020 |
| WO | WO-2020/191252 A1 | 9/2020 |

OTHER PUBLICATIONS

Lee et al., "Synthesis and SAR of sulfonyl- and phosphoryl amidine compounds as anti-resorptive agents," Bioorganic & Medicinal Chemistry Letters, vol. 20, 2010, pp. 541-545.

Ohkubo et al., "O-Selectivity and Utility of Phosphorylation Mediated by Phosphite Triester Intermediates in the N-Unprotected Phosphoramidite Method," J. American Chemical Society, vol. 126, pp. 10884-10896, 2004.

Ohkubo et al., "A new strategy for the synthesis of oligodeoxynucleotides directed towards perfect O-selective internucleotidic bond formation without base protection," Tetrahedron Letters, vol. 45, pp. 363-366, 2004.

Sekine et al., "Proton-Block Stategy for the Synthesis of Oligodeoxynucleotides without Base Protection, Capping Reaction, and P—N Bond Cleavage Reaction," J. Org. Chem., vol. 68, pp. 5478-5492, 2003.

Skaric et al., "The Homologation of 1-(2,3-Dihydroxypropyl)- into 1-(2,4-Dihydroxybutyl)-thymine," Croatica Chemica Acta, vol. 52, No. 1, pp. 51-59, 1979.

Sakaric et al., "Alophatic Thymidine and Deoxyuridine Analogs," Chroatica Chemica Acta, vol. 52, No. 3, pp. 281-292, 1979.

U.S. Appl. No. 16/636,902, Feb. 5, 2020, Vargeese, et al.
U.S. Appl. No. 16/755,544, Apr. 10, 2020, Zhang et al.
U.S. Appl. No. 17/046,752, Oct. 9, 2020, Shang et al.
U.S. Appl. No. 17/054,452, Nov. 10, 2020, Zhang et al.

Kupryushkin, M et al., 'Dodecyl-modified oligodeoxyribonucleotides as platform for oligonucleotide delivery into eukaryotic cells,' 13th Annual Meeting of the Oligonucleotide Therapeutics Society, (2017), abstract 057.

Kupryushkin, M. S. Phosphoryl Guanidines: A New Type of Nucleic Acid Analogues, Acta Naturae, 6(4): 116-118 (2014).

Stetsenko, D.A. and Pyshnyi, D.V., Ex Siberia Semper Novi: Siberia Always Brings Us Something New, Phosphoryl Guidelines: New Chemical Analogues of Nucleic Acids, Science First Hand, N2(41): 2 pages (Aug. 30, 2015). URL: https://scfh.ru/en/papers/phosphoryl-guanidines-new-chemical-analogues-of-nucleic-acids-/.

Confirmatory license agreement and security agreement between NooGen and Wave Life Sciences, Ltd., dated Jul. 22, 2002, recorded with the USPTO on Aug. 17, 2020.

RN 937803-19-5, CAS Registry, Found on STN. Retrieved Mar. 2021.

RN 937803-20-8, CAS Registry, Found on STN. Retrieved Mar. 2021.

Alimov, P.I. and Levkova, L.N., Derivatives of the Methyleneamide of Diethylphosphoric Acid, ANSSSR. Ser. Khim. 10:1889-1892 (1964).

Angell, S.M. and Baulcombe, D.C., et al. Consistent gene silencing in transgemnic plants expressing a replicating potato virus X RNA, The EMBO Jrnl., 16(12):3675-3684 (1997).

Atherton F.R et al., Studies on Phosphorylation. Part II. The Reaction of Dialkyl Phosphites with Polyhalogen Compounds in Presence of Bases. A New Method for the Phosphorylation of Amines., J. Chem. Soc., 660-663 (1945).

Barnett, R.W. and Letsinger R.L., Debenzoylation of N-Benzoylnucleoside Derivates With Ethylenediamine-Phenol, Tetra. Lett., 22:991-994 (1981).

Bazhenov, M.A. et al., Study of the Staudinger Reaction and Reveal of Key Factors Affecting the Efficacy of Automatic Synthesis of Phosphoryl Guanidinic Oligonucleotide Analogs, Russ. Jrnl. Bioorg. Chem., 45(6):699-708 (2019).

Bazhenov, M.A., Development of Effective Methods of Producing Functionalized Oligonucleotides, Inst. Chem. Bio. Bas. Med. Sib. Bran. Russ. Aca. Sci., 37 pages (2016).

Beaucage, S.L. and Caruthers, M.H., Deoxynucleoside Phosphoramidites—A New Class of Key Intermediates for Deoxypolynucleotide Synthesis, Tetra. Lett., 22(20):1859-1862 (1981).

Behlke, M.A., Chemical modification of siRNAs for in vivo use, Oligonucleotides, 18(4):305-319 (2008).

Bell, N.M. and Micklefield, J., Chemical modification of oligonucleotides for therapeutic, bioanalytical and other applications, Chembiochem, 10(17):2691-2703 (2009).

Bezgubenko, L.V. et al., Phosphorus Halides Complexes with 4-Dimethylaminopyridine and N-Methylimidazole, *Heteroatom Chemistry*, 79(5): 740-746 (2009).

Boyd, G.V. et al., Formation of 1,2,4-Triazinium 1-Imides from 4-Aryl-1-azido-13-bis(dimethylamino)-2-azabutenylium Salts: Heterocyclic N-Imides lacking Exocyclic Stabilisation, J. Chem. Soc. Chem. Commun., 1522-23 (1985).

Cates, L. et al., Phosphorus-nitrogen compounds. V. Some guanidine and 2-aminopyrimidine derivatives, J. Pharm. Sci., 55(9):966-9 (1966).

Chi, K.N et al., A phase I pharmacokinetic and pharmacodynamic study of OGX-011, a 2'-methoxyethyl antisense oligonucleotide to clusterin, in patients with localized prostate cancer, J. Natl. Cancer Inst., 97(17):1287-1296 (2005).

Chubarov, A.S. et al., Allele-Specific PCR for KRAS Mutation Detection Using Phosphoryl Guanidine Modified Primers, Diagnostics, 10(872):1-14 (2020).

Crooke, S.T., Progress in antisense technology: the end of the beginning, Methods Enzymol., 313:3-45 (2000).

Dellinger, D. et al., Solid-phase chemical synthesis of phosphonoacetate and thiophosphonoacetate oligodeoxynucleotides, J. Am. Chem. Soc., 125(4):940-50 (2003).

Dmitrienko, E. et al., Surface modification of SOI-FET sensors for label-free and specific detection of short RNA analyte, Nanomed., 11(16):2073-2082 (2016).

Dolinnaya, N. et al., Site-directed modification of DNA duplexes by chemical ligation, Nucleic Acids Res., 16(9):3721-38 (1998).

Dovydenko, I.S. et al., A convenient solid phase approach to obtain lipophilic 5'-phosphoramidate derivatives of DNA and RNA oligonucleotides (Electronic Supporting Information), Nucleos. Nucleot. Nucl. Acids, 37(2): 102-111 (2018).

Du, L. and Gatti, R.A., Progress toward therapy with antisense-mediated splicing modulation, Curr. Opin. Mol. Ther., 11(2):116-123 (2009).

Duca, M. et al., The triple helix: 50 years later, the outcome, Nucl. Acids Res., 36(16): 5123-5138 (2008).

Dyudeeva, E.S. et al., Physicochemical Properties of the Phosphoryl Guanidine Oligodeoxyribonucleotide Analogs, Russ. Jrnl. Bioorg. Chem., 45(6):709-718 (2019).

Egholm, M. et al., Peptide Nucleic Acids (PNA). Oligonucleotide Analogues with an Achiral Peptide Backbone, J. Am. Chem. Soc., 114:1895-1897 (1992).

Epanchintseva, A. et al., Non-covalent binding of nucleic acids with gold nanoparticles provides their stability and effective desorption in environment mimicking biological media, Nanotech., 29:1-12 (2018).

Fire, A. et al., Potent and specific genetic interference by double-stranded RNA in Caenorhabditis elegans, Nature, 391:806-811 (1998).

Fire, A., RNA-triggered gene silencing, Trends in Genetics, 115(9):358-363 (1999).

Fokina, A. et al., Analysis of a new charge-neutral DNA/RNA analogues Phosphoryl guanidine oligonucleotides (PGO) by gel electrophoresis, Analyt. Biochem., 555:9-11 (2018)

Froehler, B. et al., Phosphoramidate analogues of DNAL systhesis and thermal stability of heteroduplexes, Nucleic Acids Res., 16(11):4931-9 (1988).

Frohler, BC et al., Synthesis of DNA via deoxynucleoside H-phosphonate intermediates, Nucleic Acids Res., 14(13):5399-407 (1986).

(56) References Cited

OTHER PUBLICATIONS

Garafutdinov, R.R. et al., Data on multimerization for short linear DNA templated and phosphoryl guanidine promers during isothermal amplification with Bst exo-DNA polymerase, 12 pages, Data in brief 29 (2020).

Garafutdinov, R.R. et al., Prevention of DNA multimerization using phosphoryl guanidine primers during isothermal amplification with Bst exo-DNS polymerase, Biochimie, 168:259-267 (2020).

Garegg, P.J. et al., Nucleoside H-Phosphonates. III. Chemical Synthesis of Oligodeoxyribonucleotides by the Hydrogenphosphonate Approach, Tetra. Lett., 37(34):4051-4054 (1986).

Hall, A.H. et al., Highh potency silencing by single-stranded boranophosphate siRNA, Nucleic Acids Res., 34(9):2773-2781 (2006).

Hammond, S.M. et al., Post-Transcriptional Gene Silencing by Double-Stranded RNA, Nature Rev., 2:110-119 (2001).

Hau, J.F. et al., Octathymidylates Involving Alternating Neopentylphosphothionotriester-phosphodiester Linkages With Controlled Stereochemistry at the Modified P-Center, Tetra. Lett., 32(22):2497-98 (1991).

International Preliminary Report on Patentability for PCT/RU2014/000647, 7 pages (dated Feb. 28, 2017).

Jäger, A. and Engeles, J., Systhesis of Deoxynucleoside Methylphosphonates Via a Phosphonamidite Approacch, Tetra. Lett., 25(14):1437-1440 (1984).

Jearawiriyapaisarn, N., et al., Sustained dystrophin expression induced by peptide-conjugated morpholino olgomers in the muscles of mdx mice, Mol Ther., 16(9):1624-9 (2008).

Jones, S.S. et all., The Protection of Uracil and Guanine Residues in Oligonucleotide Synthesis, Tetra. Lett., 22:4755-4758 (1991).

Kaur, H. et al., Perspectives on chemistry and therapeutic applications of Locked Nucleic Acis (LNA), Chem. Rev., 107(11):4672-4697 (2007).

Kitaamura, M. et al., Direct Synthesis of Organic Azides from Primary Amines with 2-Azido-1, 3-dimethylimidazolinium Hexafluorophophate, Eur. J. Org. Chem., 458-462 (2011).

Kokel, B. and Viehe, H.G., Iminium-Activated Azides—New Reagents for the Transfer of Diazonium or Diazo Groups, Angew. Chem. Int. Engl., 19(9):716-17 (1980).

Krishna, H. and Caruthers, M., Alkynyl phosphonate DNA: a versatile "click"able backbone for DNA-based biological applications, J Am Chem Soc., 134 (28):11618-31 (2012).

Kupryushkin, M. et al., Dodectl-Modified Oligodeoxyribonucleotides as Platform for Oligonucleotide Delivery Into Eukaryotic Cells, Poster, ICBFM SB RAS, 1 page (2017).

Kupryushkin, M. et al., Phosphoryl Guanidines: A New Class of Uncharged Oligonucleotide Analogues with Remarkable Properties, Poster, ICBFM SB RAS, 1 page (2014).

Kupryushkin, M. et al., Phosphoryl Guanidines: A New Type of Nucleic Acid Analogues Presentation, Ceppheid, 20 pages (presented Dec. 2014).

Kupryushkin, M. et al., Phosphoryl Guanidines: A New Type of Nucleic Acid Analogues Presentation, ICBFM SB RAS, 15 pages (2016).

Kupryushkin, M. et al., Phosphoryl Guanidines: A New Type of Nucleic Acid Analogues Presentation, ICBFM SB RAS, 19 pages (2017).

Kupryushkin, M. et al., Precision medicine New innovative platform for development of RNA-targeted antisense drugs Presentation ICBFM SB RAS, 20 pages (2017).

Kupryushkin, M. et al., Some Properties of Phosphoryl Guanidine Oligonucleotide Analogues Poster, ICBFM SB RAS, 1 page (2015).

Kupryushkin, M.S., Phosphorryl guanidine oligonucleotides (PGO)— structural and functional features and a little bit history of its discovery Presentation, Bavarian-Russian Conference "Chemistry meets Biomedicine," 30 pages (2019).

Kuznetsov, N.A. et al., New oligonucleotide derivatives as unreactive substrate analogues and potential inhibitors of human apurinic/apyrimidinic endonuclease APE1, Mol. BioSyst., 12(67):67-75 (2016).

Kuznetsov, N.A. et al., Pre-steady state kinetics of DNA binding and abasic site hydrolysis by tyrosyl-DNA Phosphodiesterase 1, Jrnl. Biomol. Struc. Dynam., 35(11):2314-2327 (2017).

Lamond, A.I. and Sprroat, Antisense oligonucleotides made of 2'-O-AlkylRNA: their properties and applications in RNA biochemistry, B.S. FEBS Lett., 325(1-2):123-127 (1993).

Lebedeva, N.A. et al., Design of a New Fluorescent Oligonucleotide- Based Assay for a Highly Specific Real-Time Detection of Apurrinic/Apyrimidinic Site Cleavage by Tyrosyl-DNA Phophodiesterase 1, Biocon. Chem., 26:2046-2053 (2015).

Lee, J.F. et al., Aptamer therapeutics advance, Curr. Opin. Chem. Biol., 10:282-289 (2006).

Letsinger, R.L. et al., Cationic Oligonucleotides, J. Am. Chem Soc., 110:4470-4471 (1988).

Levina, A.S. et al., Impact of Delivery Method on Antiviral Activity of Phosphodiester, Phosphorothioate, and Phosphoryl Guanidine Oligonucleotides, in MDCK Cells Infected with H5N1 Bird Flu Virus, Mol. Bio., 51(4):633-638 (2017).

Lin, W.O. et al., Systhesis and Preliminary Complexation Studies of Dialkylphosphorylthiourea and guanidines, Phosphorus. Sulfur. and Silicon., 92:1-9 (1994).

Lomzov, A.A. et al., Comparaative physico chemical and biological studies of phosphorylguanidine oligonuclettide diasteriomers, Abstract 124, Books of Abstracts (2019).

Lomzov, A.A. et al., Data for isolation and properties analysis of diastereomers of a mono-substituted phosphoryl guanidine trideoxyribonucleotide, 25 pages, Data in brief 25 (2019).

Lomzov, A.A. et al., Diastereomers of a mono-substituted phosphoryl guanidine trideoxyribonucleotide: Isolation ad properties, Biochem. Biophys. Res. Comm., 513:807-811 (2019).

Lomzov, A.A. et al., Structure and hybridization properties pf phosphorylguanidine oligonucleotides, Abstract 136, Jrnl of Biomil. Struct, Dynam (2019).

Markov, A.V. et al., Antiviral Activity of a New Class of Chemically Modified Antisense Oligonucleotides against Influenza A Virus, Russ. Jrnl. Bioorg. Chem., 45(6):774-782 (2019).

Markov O.V. et al., Transport Oligonucleotides—A Novel System for Intracellular Delivery of Antisense Therapeutics, Molecules, 25(3663):1-27 (2020).

McMurry, J.E. and Coppolino, A.P., The Cyanogen Azide Ring-Expansion Reaction J. Org. Chem., 38(16):2821-2827 (1973).

Mellbye, B., et al., Cationic phosphorodiamidate morpholino oligomers efficiently prevent growth of Escherichia coli in vitro and in vivo, J Antimicrob Chemother., 65(1):98-106 (2010).

Mendell, J. et al., Eteplirsen Study Group. Eteplirsen for the treatment of Duchenne muscular dystrophy, Ann Neurol., 74(5):637-47 (2013).

Merki, E. et al., Antisense oligonucleotide directed to human aapolipoprotein B-100 reduces lipoprotein(a) levels and oxidized phospholipids on human apolipoprotein B-100 particles in Lipoprotein (a) transgenic mice, Circulation, 118(7):743-753 (2008).

Mignet, N. and Gryaznov, S., Zwitterionic oligodeoxyribonucleotide N3'—>P5'phosphoramidates:synthesis and properties, Nucleic Acids Res., 26(2):431-8 (1998).

Mulaamba, G.B. et al., Human cytomegalovirus mutant with sequence-dependent resistance to the phosphorothioate oligonucleotide fomivirsen (ISIS 2922), Antimicrob Agents Chemother., 42(2):791-973 (1998).

Nielsen. P.E. Seqquence-selective targeting of duplex DNA by peptide nucleic acids, Curr. Opin Mol. Ther., 12:184-191 (2010).

Novopashina, D. et al., Novel Peptide Conjugates of Modified Olignucleotides for Inhibition of Bacterial RNase P and Supplementary Material, Front. Pharm., 10:1-8, 13 pages (2019).

Pâtureau, B.M. et al., Induction of RNase H activity by Arabinose-peptide nucleic acid chimeras Bioconjugate Chem., 18(2):421-430 (2007).

Pavlova, A.S. et al., Amphiphilic "Like-a-Brush" Oligonucleotide Conjugates with Three Dodecyl Chains: Self-Assembly Features of Novel Scaffold Compounds for Nucleic Acids Delivery, Nanomaterials, 10(1948):1-19 (2020).

Pavlova, A.S. et al., SDS-PAGE procedure: Application for characterization of new ntirely uncharges nucleic acids analogs, Electropho., 39:670-674 (2018).

(56) References Cited

OTHER PUBLICATIONS

Pérez, B. et al., Present and future antisense therapy for splicing modulation in inherited metabolic disease, Inherit. Metabol. Disease, 33(4):397-403 (2010).

Reese, C.B. and Ubasawa, A., Reaction Between 1-Arenesulphonyl-3-Nitro-1,2,2-Triazoles and Nucleoside Base Residues. Education of the Nature of Side-Reaction During Oligonucleotide Synthesis, *Tetra. Lett.*, 21:2265-2268 (1980).

Ruckman, J. et al., 2'-Fluoropyrimidine RNA-based aptaamers to the 165-amino acid form of vascular endothelial growth factor (VEGF165). Inhibition of receptor binding VEGF-induced vascular permeability through interactions requiring the exon 7-encoded domain, J. Biol. Chem., 273(32)20556-20567 (1998).

Sarepta Therapeuttics, Sarepta Therapeutics Announces Positive Saftey Results from Phase I Clinical Study of Marburg Candidate, PipelineReview.com, La Merie Publishingm 2 pages (Feb. 10, 2014).

Sazani, P. et al., Nuclear antosense effects of neutral, anionic and cationic oligonucleotide analogs, Nucleic Acids Res., 29(19):3965-74 (2001).

Seeberger, P.H. et al., 2'-Deoxynnucleoside Dithiophosphates: Synthesis abd Biological Studies, J. Am. Chem. Soc., 117:1472-1478 (1995).

Sharp, P.A., RNAi abd double strand RNA, Genes and Development, 13:139-141 (1999).

Sinha, ND et al., Polymer suport oligonucleotide synthesis XVIII: use of beta-cyanorthyl-N, N-dialkylamino-/N-morpholino and phosphoramidite of deoxynucleosides for the synthesis of DNA fragments simplify deprotection and isolation of the final product, Nucleic Acids Res., 12(11):4539-57 (1984).

Skvortsova, Y.V. et al., A New Antisense Phosphoryl Guanidine Oligo-2'-O-Methylribonucleotide Penetrates Into Intracellular Mycobacteria and Suppresses Target Gene Expression, Front. Pharm., 10:1-9 (2019).

Stec, W.J. et al., Automated Solid-Phase Synthesis, Separation and Sterochemistry of Phosphorothioate Analogues of Oligodeoxyribonucleotides, J. Am. Chem. Soc., 106-6077-6079 (1984).

Stein, C.A. et al., Physicochemical properties of phosphorothioate oligodeoxynucleotides, Nucl. Acids Res., 16(8):3209-3221 (1988).

Stetsenko, D., A New Class of Oligonuccletide Analogues with Remarkable Properties Presentation, XXI International Round Table on Nucleot. Nucleic Acids, 11 pages (presented Aug. 2014).

Stetsenko, D., A new oligonucleotide-based therapy for Duchenne muscular dystrophy Presentation, ICBFM SB RAS, 11 pages (2016).

SU, Y. et al., Neutral and Negatively Charged Phosphate Modification Altering Thermal Stability, Kinetics of Formation and Monovalent Ion Dependence of Formation and Monovalent Ion Dependence of DNA G-Quadruplexes, Chem. Asian J., 14:1212-1220 (2019).

Su, Y. et al., The Importance of Phosphates for DNA-G-Quadruplex FoOrmation: Evaluation of Zwitterionic G-Rich Oligodeoxynucleotides, ChemBioChem, 21:1-13 (2020).

Summerton, J. and Weller, D. Morpholino Antisense Oligomers: Design, Preparation, and Properties, Antisense Nucl. Acid Drug Dev., 7:187-195 (1997).

Summerton, J.E. In *Peptide Nucleeic Acids, Morpholinos and Related Antisense Biomolecules* (Janson, C.G.; During, M.J., Eds), 2003, Kluwer Academic/Plenum Publishers, Chapter 6.

Swenson, d. et al., Chemical modifications of antisense morpholino oligomers enhance their efficacy aagainst Ebola virus infection, Antimicrob Agents Chemother., 53(5):2089-99 (2009).

Tuerk, C. and Gold, L., Systematic Evolution of Ligands by Exponential Enrichment: RNA Ligands to Bacteriophage T4 DNA Polymearase, Science, 249:505-510 (1990).

Tuschl, T., RNA Interference and Amall Interfering RNAs, ChemBioChem, 2:239-245 (2001).

Vinores, S.A. Pegaptanib in the treatment of wet, age-related macular degeneration, Int. J. Nanomed. 1(3):263-268 (2006).

Vladyko, A. et al., Synthesis, Purification and Delivery into Mammalian Cells of Phosphoryl Guanidine Oligonucleotides (PGO) with Either DNA ot 2'-OME RNA Backbone Poster, ICBFM SB RAS, 1 page (2015).

Vionnet, O. and Baulcombe, D.C, Systemic signalling in gene silencing, Nature, 389:553 (1997).

Wilson, C., and Keefe, A.D. et al., Building oligonuccleotide therapeutics uusing non-natural chemistries, Curr Opin Chem Biol., 10(6):607-614 (2006).

Wu, B. et al., Effective rescue of dystrophin improves cardiac function in dystrophin-deficient mice by a modified morpholino oligomer, Proc Natl Acad Sci USA, 105(39):14814 (2008).

Hi, S. and Zhao, Y., Synthesis of the Bidentate Organophosphorus Compounds with Anurea Substituents, Synth, Commun., 20(21):3295-3301 (1990).

Xu, Z.J. et al., Use of DNAzymes for cancer research and therapy, Chin. Sci. Bull., 57(26):3404-3408 (2012).

Yamada, C. et al., Synthesis and biochemiical evaluation of phosphonoformate oligodeoxyribonucleotides, J Am Chem Soc., 128(15):5251-61 (2006).

Yin, H. et al., Cell-penetrating peptide-conjugated antisense oligonucleotides restore systemic muscle and cardiac dystrophin expression and function, Hum Mol Genet., 17(24):3909-18 (2008).

Zamecnik, P.C. and Stephensom, M.L. Inhibition of Rous sarcoma virus replication and cell transformation by a specific oligodeoxynnucleotide, Proc, Natl. Acad. Sci, USA, 75(1):280-284 (1978).

Zhukov, S.A., Production of Tetrasubstituted Diaminocarbenium Azides for Systhesis of Oligonucleotide Derivates, Presentation, Min. Sci. Higher Ed. Rudd. Fed., 40 pages (2020).

\* cited by examiner

MODIFIED OLIGONUCLEOTIDES AND METHODS FOR THEIR SYNTHESIS

CROSS-REFERENCE TO RELATED APPLICATIONS

This application is a national stage of International Application No. PCT/RU2014/000647, which was filed on Aug. 28, 2014, and which claims priority to RU 2014134380 which was filed on Aug. 22, 2014, and which are both herein incorporated by reference.

REFERENCE TO SEQUENCE LISTING SUBMITTED VIA EFS-WEB

This application includes an electronically submitted sequence listing in .txt format. The .txt file contains a sequence listing entitled "6611_0005PUS1_ST25.txt" created on Nov. 12, 2019 and is 17,281 bytes in size. The sequence listing contained in this .txt file is part of the specification and is hereby incorporated by reference herein in its entirety.

TECHNICAL FIELD

The present invention relates to nucleotides and oligonucleotides having a modified phosphate group, and methods for their synthesis.

BACKGROUND

Nucleic acid derivatives such as oligonucleotides appended with various additional functionalities are used widely as research tools in life sciences, in particular, they are regarded as promising therapeutics [1] and sensitive probes for molecular diagnostics [2]. Several oligonucleotide therapeutics have received FDA approval to go into clinic. Examples include an antiviral agent Vitravene (Fomivirsen, ISIS 2922) [3], an anti-angiogenic aptamer Macugen (Pegaptanib sodium) [4] and an anti-cholesterol gapmer Mipomersen (Kynamro, ISIS 301012) [5]. A number of other oligonucleotide candidates such as siRNA, DNAzymes and antisense morpholino analogues (PMO) are currently undergoing various phases of clinical trials.

To be regarded as potential therapeutic candidates, oligonucleotides should correspond to the following requirements.
1. Sufficient stability and sequence-specificity of a complementary complex with their biological target (most often it is a cellular RNA).
2. Increased resistance in biological media such as serum.
3. Beneficial physico-chemical properties such as aqueous solubility and chemical stability.
4. Cost-effective synthesis and affordable price.
5. Efficient cell uptake and in vivo delivery, preferably in the absence of external transfection agents.

According to the mechanism of action, oligonucleotide analogues can interfere with practically any stage of genetic information transfer: either from DNA to RNA (transcription) or from RNA to protein (translation). Inhibition of transcription is performed by binding genomic DNA by triplex-forming oligonucleotides (TFOs) [6], in particular, peptide nucleic acids (PNAs) [7]. Inhibition of translation (antisense mechanism) is realised through mRNA blocking [8]. Most of known to-date oligonucleotide analogues act by antisense mechanism. Those are small interfering RNAs (siRNAs) [9], nucleic acid enzymes (ribozymes or DNAzymes) [10], and a majority of chemically modified oligonucleotide analogues [11]. Specific oligonucleotide derivatives such as aptamers can also block protein function by direct binding to proteins or small molecule co-factors [12].

Most of antisense oligonucleotide analogues bind mRNA and inhibit translation via steric block [13]. Those include a majority of analogues with modifications in the sugar such as 2'-fluoro[14], 2'-O-methyl [15], 2'-O-β-methoxyethyl (2'-MOE) [16] or locked nucleic acid (LNA) [17] derivatives. Oligonucleotide analogues, which substitute an uncharged group for anionic internucleoside phosphate group such as methylphosphonates [18], phosphotriesters [19] or phosphoramidates [20] also act by steric block. The same antisense mechanism is involved in action of distant nucleic acid mimics such as PNAs [21] or phosphorodiamidate morpholino oligonucleotides (PMO) [22].

Additional interest attract those analogues, which are able to irreversibly inactivate RNA by catalysing its hydrolytic cleavage, for example, via recruiting cellular enzyme RNase H by 2'-deoxy phosphorothioates [23], ara-2'-fluoro derivatives (2'-FANA) [24] or gapmers [24]. SiRNAs induce catalytic cleavage of mRNA by activating RISC complex with ribonuclease activity [25] whereas nucleic acid enzymes (ribozymes or DNAzymes) do not require proteins for their catalytic RNA-cleaving action [27].

Many oligonucleotide analogues have modified internucleoside phosphate groups. Among them phosphorothioates [28], phosphorodithioates [29] and boranophosphates [30]. A positive feature of those derivatives is their relatively low cost due to the use of natural 2'-deoxyribonucleotides and highly effective solid-phase DNA phosphoramidite chemistry [31]. Phosphate-modified analogues contain asymmetric phosphorus atom(s) and are usually obtained as a mixture of $2^{n-1}$ diastereomers for n-mer oligonucleotide. Different diastereomers often have different affinity to RNA and enzyme resistance, which are crucial for potential antisense action.

Currently, a task of especial priority is the development of oligonucleotide analogues with efficient cell uptake and in vivo delivery, preferably in the absence of external delivery agents such as cationic lipids, polymers or nanoparticles. Here, oligonucleotide analogues with reduced or completely eliminated negative charge may be particularly interesting [32]. Among them are oligonucleoside phosphoramidates that substitute charge neutral phosphoramidate group for anionic phosphate. Chemical synthesis of phosphoramidates is relatively straightforward. However, those analogues exhibit reduced affinity to RNA [33] and are sensitive to acidic hydrolysis [34]. N3'→P5' phosphoramidates have improved RNA binding but are difficult to synthesise [35]. Those representatives that have positively charged groups in the side chains are more accessible and have excellent enzymatic stability but their affinity to RNA is lower [36]. At the same time a majority of known phosphoramidate derivatives including such useful antisense agents as morpholinos (PMOs) [37] show some lability at acidic pH. Improved acid stability would be required to prevent degradation of oligonucleotide analogues inside endosomes.

Over the last decade new phosphonate oligonucleotide analogues have emerged, which substitute an ionisable phosphonate group for natural phosphate. Among them are phosphonoacetates and thiophosphonoacetates [38], phosphonoformates [39] and 1,2,3-triazol-4-ylphosphonates [40]. Those compounds exhibit increased biological resistance and adequate RNA binding, and, additionally, they support RNase H cleavage and have improved cell uptake even in the absence of transfection agents. However, their chemical synthesis is difficult and costly.

Modified nucleotides and oligonuclides containing at least once the structure P=N-Acc, wherein Acc is an electronic acceptor have also been described [41]. Suitable identities for Acc are —CN, —SO$_2$R and electron-deficient, six membered N$^+$ heterocycles in which at least one nitrogen is alkylated and in an ortho or para position.

At the moment, considerable attention is drawn to phosphorodiamidate morpholino oligonucleotides (PMOs), which are known antisense agents [42]. They are commercially available from GeneTools LLC. PMOs are actively explored as potential therapeutics by Sarepta Therapeutics, (until 2012 AVI Biopharma). In 2013 the company announced successful completion of Phase III clinical trials agenst Duchenne muscular dystrophy (DMD) by a PMO drug Eteplirsen (AVI-4658), which corrects aberrant splicing of dystrophin pre-mRNA [43]. At the beginning of 2014 Sarepta Therapeutics has said that their morpholino drug candidate AVI-7288 has successfully passed Phase I clinical trials against deadly Marburg hemorrhagic fever caused by an RNA-containing virus [44].

However, morpholinos are acid-sensitive just as other phosphoramidates [45]. Moreover, their synthesis is based on P(V) chemistry [46]. The chemistry may lead to side-reactions such as the modification of the O$^6$ in guanine [47]. It can be prevented by a protecting group at the O$^6$ position [48] but that requires a special G monomer, which adds up to the costs of PMO synthesis. Another drawback of the chemistry is that it is incompatible with common phosphoramidite method and cannot use the modifying and labeling reagents available from usual suppliers such as Glen Research, Inc.

Another serious handicap of PMOs is the difficulty of their chemical modification to obtain various derivatives for structure-activity studies. Only a few side-chain modifications to PMO were proposed that are claimed to enhance their cell uptake and therapeutic efficacy [49].

Morpholinos often show relatively poor efficiencies of cell uptake and hence high repeated doses are required for good therapeutic effect to be seen. Cell uptake of PMO-peptide conjugates is much higher than for naked PMO and thus much lower doses are needed in vivo [50]. There is a need to obtain better oligonucleotide analogues that will show greater levels of cell and tissue delivery and improved therapeutic efficacy in the absence of delivery aids.

Thus, the development of new oligonucleotide analogues remains an important task.

SUMMARY OF THE INVENTION

This present invention is based on the inventors' insight into prospective candidates for oligonucleotide therapeutics with improved cell uptake. Specifically, the present invention is based on the following ideas for suitable approaches to/characteristics for new such oligonucleotide therapeutics:
1. Substitute charge neutral or positively charged groups for natural anionic phosphate.
2. Comply with the requirements for potential oligonucleotide therapeutics outlined above.
3. Preferably retain a conventional nucleotide backbone.
4. Display sufficient chemical stability.
5. Possess structural flexibility that allows for incorporation of diverse side-chain groups.
6. Have low toxicity.

New oligonucleotide analogues that correspond to the above requirements and may potentially exhibit improved cell uptake are disclosed herein. Broadly speaking, these oligonucleotide analogues are in the class of phosphoryl imines and analogues thereof, for example, phosphoryl guanidines, phosphoryl amidines, phosphoryl isoureas, phosphoryl isothioureas, phosphoryl imidates, phosphoryl imidothioates and analogues thereof.

Accordingly, in one aspect the present invention relates to a nucleotide or oligonucleotide comprising a phosphoryl guanidine (FI), phosphoryl amidine (FII), phosphoryl isourea (FIII), phosphoryl isothiourea (FIV), phosphoryl imidate (FV) or phosphoryl imidothioate (FVI), for example, a phosphoryl guanidine (FI), phosphoryl amidine (FII), phosphoryl isourea (FIII), phosphoryl isothiourea (FIV). It will be appreciated that the invention also relates to modified phosphate versions of these moieties; that is, phosphates in which one or more of the oxygen atoms surrounding the phosphorus atoms has been replaced, for example, by a sulfur atom, selenium atom, imino group or a borane.

For example, the present invention relates to, inter alia, nucleotides or oligonucleotides, and analogues thereof, comprising one or more of the following motifs:

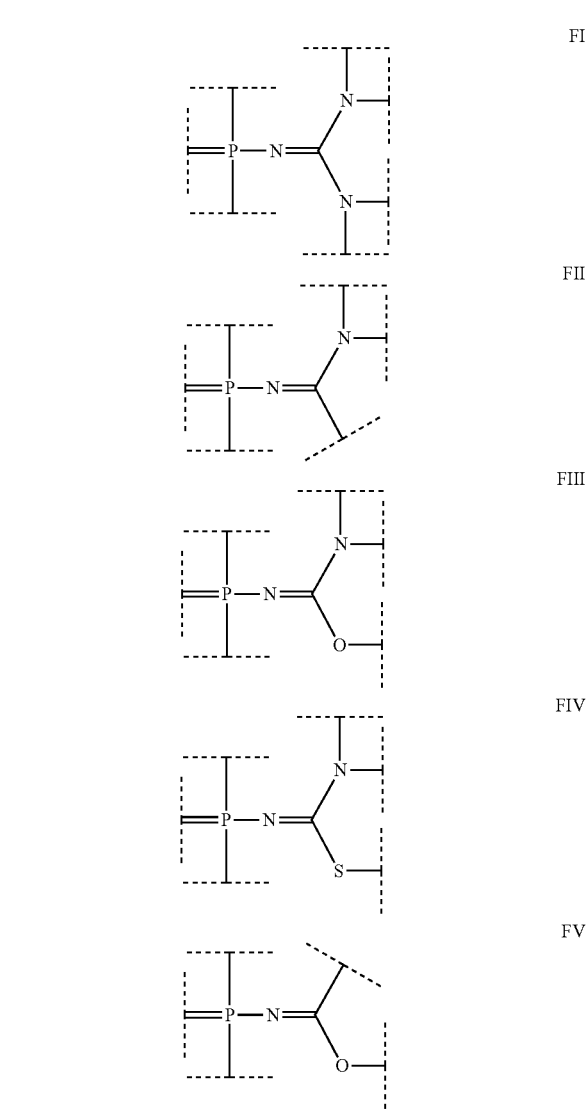

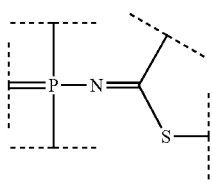

wherein ---- indicates a point of attachment to a substituent.

These modified phosphate groups are of considerable interest because of their physico-chemical properties. Without wishing to be bound to any particular theory, the present inventors believe that these moieties can be charge neutral, charge negative or charge positive at physiological pH, making them of considerable interest for the synthesis of nucleotides and oligonucleotides useful in therapeutic, diagnostic and research applications.

Furthermore, the present inventors have found that these modified phosphate groups can be incorporated into oligonucleotide structures conveniently using methods as described herein, and are compatible with many known and biologically interesting modified and/or labelled oligonucleotide motifs and sequences.

For example, the motif may be:

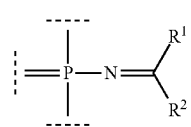
(FVII)

wherein:

$R^1$ is selected from —$NR^{1A}R^{1B}$, —$OR^3$, —$SR^3$, —H, —S(O)H, —S(O)$R^3$, —S(O)$_2$H, —S(O)$_2R^3$, —S(O)$_2NH_2$, —S(O)$_2N$ H$R^3$, —S(O)$_2NR^3_2$, —C$_{2-10}$alkenyl, —C$_{2-10}$alkynyl, —C$_{6-10}$aryl, or —O$_{5-10}$heteroaryl;

$R^2$ is selected from —H, —$NR^{2A}R^{2B}$, —$OR^3$, —$SR^3$, halogen, —CN, —S(O)H, —S(O)$R^3$, —S(O)$_2$H, —S(O)$_2R^3$, —S(O)$_2NH_2$, —S(O)$_2NHR^3$, —S(O)$_2NR^3_2$, C$_{2-10}$alkenyl, C$_{2-10}$alkynyl, —C$_{6-10}$aryl, or —C$_{5-10}$heteroaryl;

wherein each $R^{1A}$, and $R^{2B}$ is independently selected from —H, —C$_{2-10}$alkenyl, —C$_{2-10}$alkynyl, —C$_{6-10}$aryl, or —O$_{5-10}$heteroaryl;

optionally wherein $R^{1A}$ and $R^{2A}$ together form an alkylene or heteroalkylene chain of 2-4 atoms in length;

optionally wherein $R^{1A}$ and $R^{1B}$, together with the atom to which they are bound, form a 5-8 membered heterocycle;

optionally wherein $R^{2A}$ and $R^{2B}$, together with the atom to which they are bound, form a 5-8 membered heterocycle;

$R^3$ is selected from —C$_{1-10}$alkyl, —C$_{2-10}$alkenyl, —C$_{2-10}$alkynyl, —C$_{6-10}$aryl, or —O$_{5-10}$heteroaryl;

wherein each alkyl, alkenyl, alkynyl, aryl, heteroaryl, alkylene or heteroalkylene is optionally substituted.

Accordingly, in a first aspect, the present invention may provide a compound of Formula (I):

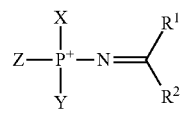
(I)

wherein Z is selected from —O$^-$, —S$^-$, —Se$^-$, —N$^-R^N$, or —BH$_3^-$, wherein $R^N$ is H, C$_{1-4}$alkyl, or a protecting group;
X is selected from the 5' end of a nucleoside, nucleoside analogue, oligonucleotide, or oligonucleotide analogue and Y is selected from the 3' end of a nucleoside, nucleoside analogue, oligonucleotide, or oligonucleotide analogue; —H, —OH, —SH, NHR$^N$, —O-PG, or S-PG, wherein PG is a protecting group; a linker, a monophosphate or diphosphate, or a label or quencher;
or
Y is selected from the 3' end of a nucleoside, nucleoside analogue, oligonucleotide, or oligonucleotide analogue and X is selected from the 5' end of a nucleoside, nucleoside analogue, oligonucleotide, or oligonucleotide analogue, —H, —OH, —SH, NHR$^N$, —O-PG, or S-PG, wherein PG is a protecting group; a linker, a monophosphate or diphosphate, or a label or quencher;

$R^1$ is selected from —$NR^{1A}R^{1B}$, —$OR^3$, —$SR^3$, —H, —S(O)H, —S(O)$R^3$, —S(O)$_2$H, —S(O)$_2R^3$, —S(O)$_2NH_2$, —S(O)$_2N$ HR$^3$, —S(O)$_2NR^3_2$, —C$_{2-10}$alkenyl, —C$_{2-10}$alkynyl, —C$_{6-10}$aryl, or —O$_{5-10}$heteroaryl;

$R^2$ is selected from —H, —$NR^{2A}R^{2B}$, —$OR^3$, —$SR^3$, halogen, —CN, —S(O)H, —S(O)$R^3$, —S(O)$_2$H, —S(O)$_2R^3$, —S(O)$_2NH_2$, —S(O)$_2NHR^3$, —S(O)$_2NR^3_2$, C$_{2-10}$alkenyl, C$_{2-10}$alkynyl, —C$_{6-10}$aryl, or —C$_{5-10}$heteroaryl;

wherein each $R^{1A}$, $R^{2A}$, and $R^{2B}$ is independently selected from —H, —C$_{1-10}$alkyl, —C$_{2-10}$alkenyl, —C$_{2-10}$alkynyl, —C$_{6-10}$aryl, or —C$_{5-10}$heteroaryl;

optionally wherein $R^{1A}$ and $R^{2A}$ together form an alkylene or heteroalkylene chain of 2-4 atoms in length;

optionally wherein $R^{1A}$ and $R^{1B}$, together with the atom to which they are bound, form a 5-8 membered heterocycle;

optionally wherein $R^{2A}$ and $R^{2B}$, together with the atom to which they are bound, form a 5-8 membered heterocycle;

$R^3$ is selected from —C$_{1-10}$alkyl, —C$_{2-10}$alkenyl, —C$_{2-10}$alkynyl, —C$_{6-10}$aryl, or —C$_{5-10}$heteroaryl;

wherein each alkyl, aryl, heteroaryl, alkylene or heteroalkylene is optionally substituted.

In some embodiments, $R^1$ is selected from —$NR^{1A}R^{1B}$, —$OR^3$, and —$SR^3$. In some embodiments, $R^1$ is —$NR^{1A}R^{1B}$.

Accordingly, the compound may be a compound of formula (Ia), wherein X, Y, Z, $R^{1A}$, $R^{1B}$ and $R^2$ are as defined herein.

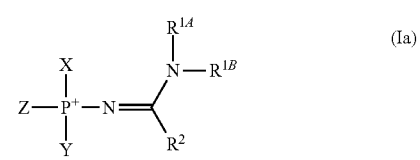
(Ia)

The compound maybe a "modified" nucleotide, "modified" oligonucleotide, or "modified" nucleoside triphosphate. It will be understood that the term "modified" in this context refers to the incorporation of the modified phosphate moiety depicted in Formula (I), that is, a phosphate comprising the motif depicted in Formula (FVII).

Nucleoside triphosphates are molecules containing a nucleoside bound to three phosphate groups. It will be understood that in this context, the term phosphate includes modified phosphates, as defined herein. Suitably, the nucleoside triphosphate has a triphosphate group that is three phosphates linked together in a row; that is, the molecule may be a dNTP or similar. In other embodiments, nucleosides may have phosphates at both the 5' and 3' positions, for example, a single phosphate group at the 5' position and diphosphate group (two phosphates linked together) at the 3' position. It will be appreciated that any and all of these phosphate groups may be modified as described herein.

When the compound is an oligonucleotide, it will be understood that each further nucleoside may itself independently be a nucleoside analogue and, additionally or alternatively, each further phosphate group (if present) may in itself be modified.

In some embodiments, $R^2$ is selected from —H, —NR$^{2A}$R$^{2B}$, —OR$^3$, —SR$^3$, —S(O)H, —S(O)R$^3$, —S(O)$_2$H, —S(O)$_2$R$^3$, —S(O)$_2$NH$_2$, —S(O)$_2$NHR$^3$, —S(O)$_2$NR$^3_2$, —C$_{2-10}$alkenyl, —C$_{2-10}$alkynyl, —C$_{6-10}$aryl, or —O$_{5-10}$heteroaryl, wherein each alkyl, aryl, heteroaryl, alkylene or heteroalkylene is optionally substituted.

In some embodiments, $R^2$ is —H, —NR$^{2A}$R$^{2B}$, —OR$^3$, —SR$^3$, C$_{1-10}$alkyl, C$_{2-10}$alkenyl, C$_{2-10}$alkynyl, —C$_{6-10}$aryl, or —C$_{5-10}$heteroaryl, wherein each alkyl, aryl, heteroaryl, alkylene or heteroalkylene is optionally substituted.

In some embodiments, $R^2$ is —H, —NR$^{2A}$R$^{2B}$ or —OR$^3$. For example, the compound may contain a phosphoryl formamidine (P—N=CHNR$^{1A}$R$^{1B}$) group, a phosphoryl guanidine (P—N=C(NR$^{1A}$R$^{1B}$)(NR$^{2A}$R$^{2B}$)), or a phosphoryl isourea (P—N=C(NR$^{1A}$R$^{1B}$)OR$^3$) group.

In some embodiments, $R^3$ is C$_{1-4}$alkyl, preferably methyl.

In some embodiments, $R^{1A}$ is independently selected from —H and —C$_{1-4}$alkyl optionally substituted with one or more substituents selected from —F, —Cl, —Br, —I, —OH, —C$_{1-4}$alkoxy, —NH$_2$, —NH(C$_{1-4}$alkyl), and —N(C$_{1-4}$alkyl)$_2$; preferably from —H and —C$_{1-4}$alkyl, more preferably from —H and methyl.

In some embodiments, $R^{1B}$ is independently selected from —H and —C$_{1-4}$alkyl optionally substituted with one or more substituents selected from —F, —Cl, —Br, —I, —OH, —C$_{1-4}$alkoxy, —NH$_2$, —NH(C$_{1-4}$alkyl), and —N(C$_{1-4}$alkyl)$_2$; preferably from —H and —C$_{1-4}$alkyl, more preferably from —H and methyl.

In some embodiments, $R^{2A}$ is independently selected from —H and —C$_{1-4}$alkyl optionally substituted with one or more substituents selected from —F, —Cl, —Br, —I, —OH, —C$_{1-4}$alkoxy, —NH$_2$, —NH(C$_{1-4}$alkyl), and —N(C$_{1-4}$alkyl)$_2$; preferably from —H and —C$_{1-4}$alkyl, more preferably from —H and methyl.

In some embodiments, $R^{2B}$ is independently selected from —H and —C$_{1-4}$alkyl optionally substituted with one or more substituents selected from —F, —Cl, —OH, —C$_{1-4}$alkoxy, —NH(C$_{1-4}$alkyl), and —N(C$_{1-4}$alkyl)$_2$; preferably from —H and —C$_{1-4}$alkyl, more preferably from —H and methyl.

In some embodiments, each $R^{1A}$, $R^{1B}$, $R^{2A}$, and $R^{2B}$ is independently selected from —H and —C$_{1-4}$alkyl optionally substituted with one or more substituents selected from —F, —Cl, —Br, —I, —OH, —C$_{1-4}$alkoxy, —NH$_2$, —NH(C$_{1-4}$alkyl), and —N(C$_{1-4}$alkyl)$_2$; preferably from —H and —C$_{1-4}$alkyl optionally substituted with one to three substituents selected from —F, —Cl, —OH, and —NH$_2$, more preferably from —H and —C$_{1-4}$alkyl, more preferably from —H and methyl.

In some embodiments, $R^2$ is —NR$^{2A}$R$^{2B}$, preferably —NMe$_2$.

In some embodiments, $R^1$ is —NH$_2$ or —NMe$_2$.

In some embodiments, $R^{1A}$ and $R^{2A}$ together form an alkylene or heteroalkylene chain of 2-4 atoms in length and $R^{1B}$ and $R^{2B}$ are each independently selected from —H and —C$_{1-4}$alkyl. In some embodiments, $R^{1A}$ and $R^{2A}$ together form —CH$_2$—CH$_2$—. In some embodiments, $R^{1A}$ and $R^{2A}$ together form —CH$_2$—CH$_2$— and $R^{1B}$ and $R^{2B}$ are —H or methyl.

In some embodiments, $R^{1A}$ and $R^{1B}$, together with the atom to which they are bound, form a 5-8 membered heterocycle, preferably a pyrrolidine, piperidine, piperazine or morpholine. Suitably they, together with the atom to which they are bound, form a 5-membered heterocycle, preferably a pyrrolidine.

In some embodiments, $R^{2A}$ and $R^{2B}$, together with the atom to which they are bound, form a 5-8 membered heterocycle, preferably pyrrolidine, piperidine, piperazine or morpholine. Suitably they, together with the atom to which they are bound, form a 5-membered heterocycle, preferably a pyrrolidine.

As described herein, Z may be selected from —O$^-$, —S$^-$, —Se$^-$, —N$^-$R$^N$, or —BH$_3$, wherein R$^N$ is —H, —C$_{1-4}$alkyl, or a protecting group. Preferably, Z is from —O$^-$ or —S$^-$, most preferably —O$^-$. It will be appreciated that —P$^+$—O$^-$ is a resonance structure of —P=O.

Certain preferred compounds are compounds of the following formulae:

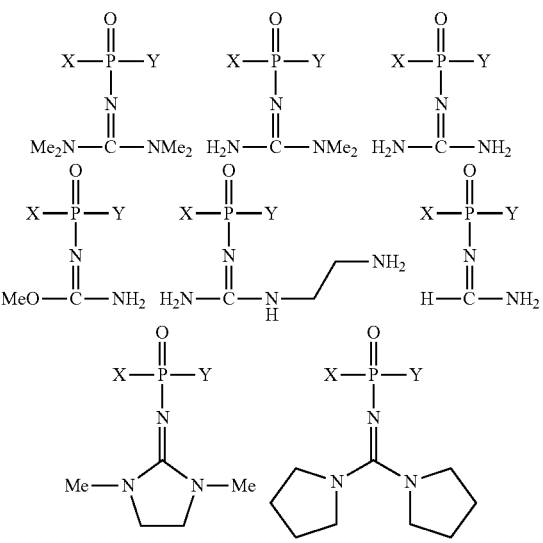

In a further aspect, the present invention provides an oligonucleotide having at least one modified phosphate moiety of formula FVII:

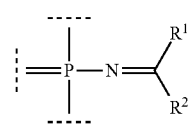

wherein $R^1$ and $R^2$ are as defined herein.

In a further aspect, the present invention provides an oligonucleotide wherein a phosphate linking adjacent nucleosides/nucleoside analogues comprises a phosphoryl guanidine, phosphoryl amidine, phosphoryl isourea, phosphoryl isothiourea, phosphoryl imidate or phosphoryl imidothioate.

In a further aspect, the present invention provides a method of synthesizing a compound comprising a motif of Formula FVII:

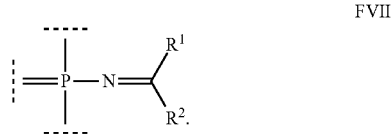

FVII

In one aspect, the method comprises reaction of a phosphorous acid derivative with an imino derivative $HN=CR^1R^2$ or an N-silylated imino derivative $R^{Si}_3SiN=CR^1R^2$ in the presence of an oxidant, and optionally a silylating agent and/or a base (Procedure A), wherein each $R^{Si}$ is an alkyl or aryl group. For example, the phosphorous acid derivative may be a phosphite or H-phosphonate.

Examples of imino derivatives for Procedure A include, without limitation, 1,1,3,3-tetramethylguanidine (TMG), guanidine hydrochloride, 1,1-dimethylguanidine sulphate, 1,3-diphenylguanidine, formamidine hydrochloride, acetamidine hydrochloride, 1H-pyrazole-1-carboxamidine hydrochloride, N-Boc-1H-pyrazole-1-carboxamidine, ethyl formimidate hydrochloride, ethyl acetimidate hydrochloride, O-methylisourea hydrogen sulfate, S-methylisothiourea hydrogen sulphate, S-benzylisothiourea hydrochloride and the like.

It will be appreciated that an imino derivative may be in the form of a free base or a salt as described herein. If the imino derivative is a salt, a base may be added to liberate a free base of the imino derivative and/or a silylating agent may be employed to produce an N-silylated derivative of an imino compound.

The oxidant may be iodine $I_2$, bromine $Br_2$, chlorine $Cl_2$, iodine chloride ICl, N-bromosuccinimide, N-chlorosuccinimide, N-iodosuccinimide, carbon tetrachloride $CCl_4$, bromotrichloromethane $CCl_3Br$, tetrabromomethane $CBr_4$, tetraiodomethane $CI_4$, iodoform $CHI_3$, hexachloroethane $C_2Cl_6$, hexachloroacetone $(CCl_3)_2CO$ or the like. A preferred oxidant is iodine $I_2$.

In a further aspect, the method comprises reaction of a phosphorous acid derivative with an organic azide, optionally in the presence of a silylating agent and/or a base (Procedure B).

For example, the organic azide may be selected from a bis(disubstituted amino)-1-azidocarbenium salt, a 1-(disubstituted amino)-1-azidocarbamidinium salt, a 1-(disubstituted amino)-1-azido-ethene, an N-substituted-1-azidocarbamidine and the like.

In the reactions of Procedure A and Procedure B, the reaction may be carried out in the presence of a silylating agent, for example, N,O-bis(trimethylsilyl)acetamide (BSA), N,O-bis(trimethylsilyl)trifluoroacetamide (BSTFA), chlorotrimethylsilane, bromotrimethylsilane, iodotrimethylsilane, triethylsilyl chloride, triphenylsilyl chloride, hexamethyldisilazane, trimethylsilyl trifluoromethanesulfonate (TMSOTf), dimethylisopropylsilyl chloride, diethylisopropylsilyl chloride, tert-butyldimethylsilyl chloride, tert-butyldiphenylsilyl chloride, triisopropylsilyl chloride, dimethyldichlorosilane, diphenyldichlorosilane and the like. For example, the reaction may be carried out in the presence of a silylating agent selected from N,O-bis(trimethylsilyl)acetamide (BSA), N,O-bis(trimethylsilyl)trifluoroacetamide (BSTFA), and chlorotrimethylsilane.

In the reactions of Procedure A and Procedure B, the reaction may be carried out in the presence of a base, for example, triethylamine, N,N-diisopropylethylamine (DIEA), N-methylmorpholine, N-ethylmorpholine, tributylamine, 1,4-diazabicyclo[2.2.2]octane (DABCO), N-methylimidazole (NMI), pyridine, 2,6-lutidine, 2,4,6-collidine, 4-dimethylaminopyridine (DMAP), 1,8-bis(dimethylamino)naphthalene ("proton sponge"), 1,8-diazabicyclo[5.4.0]undec-7-ene (DBU), 1,5-diazabicyclo[4.3.0]non-5-ene (DBN), 1,5,7-triazabicyclo[4.4.0]dec-5-ene (TBD), 7-methyl-1,5,7-triazabicyclo[4.4.0]-dec-5-ene (MTBD), 1,1,3,3-tetramethylguanidine (TMG), 2-tert-butyl-1,1,3,3-tetramethylguanidine, 2,8,9-trimethyl-2,5,8,9-tetraaza-1-phosphabicyclo[3.3.3]-undecane, phosphazene base or the like.

Examples of solvents for Procedure A include, without limitation, pyridine, 2-picoline, 3-picoline, 4-picoline, quinoline, tetrahydrofuran (THF), 1,4-dioxane, 1,2-dimethoxyethane (DME), diethylene glycol dimethyl ether (diglym), diethyl ether, acetonitrile and the like.

Examples of solvents for Procedure B include, without limitation, acetonitrile, N,N-dimethylformamide (DMF), N,N-dimethylacetamide (DMA), N-methylpyrrolidone (NMP), tetramethyl urea, 1,3-dimethylimidazolidin-2-one, sulfolane, hexamethyl phosphortriamide (HMPT), 1,4-dioxane, tetrahydrofuran (THF), acetone, ethyl acetate and the like.

Further details of these Procedures are provided below.

As described herein, a particular advantage of the modified phosphate moieties of the present invention is the convenient incorporation of these moieties as demonstrated by the present inventors. For example, a modified phosphate moiety of Formula VI can be readily incorporated into an oligonucleotide during sequential oligonucleotide synthesis based on H-phosphonate or phosphoramidite chemistry. Further details are provided below.

Any one or more of the aspects of the present invention may be combined with any one or more of the other aspects of the present invention. Similarly, any one or more of the features and optional features of any of the aspects may be applied to any one of the other aspects. Thus, the discussion herein of optional and preferred features may apply to some or all of the aspects. In particular, optional and preferred features relating to the compounds, motifs, and intermediates, methods of making the compounds and methods of using the compounds, etc apply to all of the other aspects. For example, substituents preferences for the compounds also apply to the azides/imino derivatives and visa versa. Furthermore, optional and preferred features associated with a method or use may also apply to a product and vice versa.

FIGURES

The invention is further described, without limitation, with reference to the following:

FIG. 1. RP-HPLC of oligonucleotides 5'-d(GCGC-CAAACpA)(SEQ ID NO: 11) (thin black line), 5'-d(GCGC-CAAApCpA) (SEQ ID NO: 7) (grey line) and 5'-d(GCGC-CAApApCpA) (SEQ ID NO: 12) (bold black line) modified with N,N,N',N'-tetramethyl-N"-phosphorylguanidine groups; p here and below marks position of a modifying group.

Figure 2:
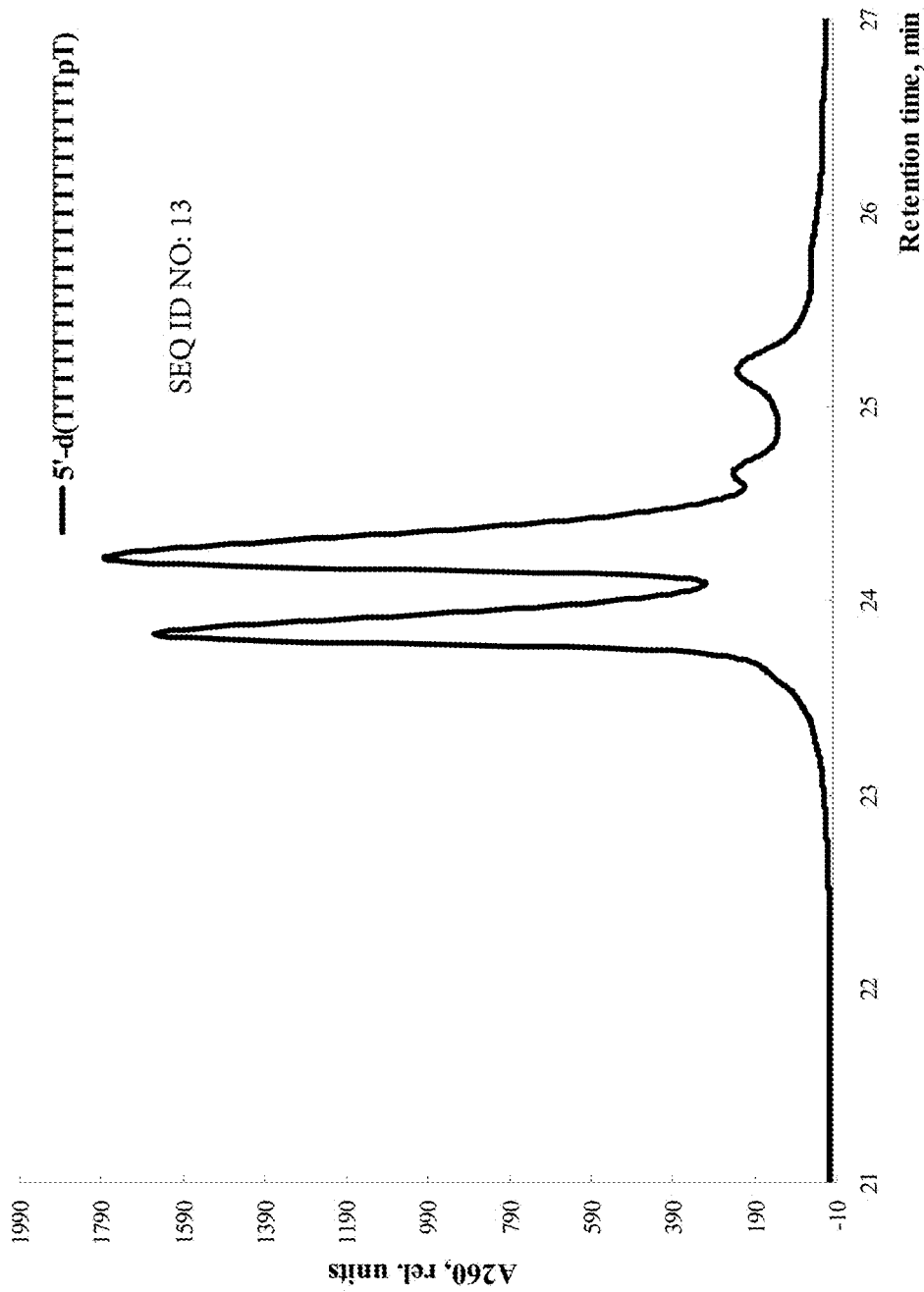

FIG. 2. RP-HPLC of oligonucleotide 5'-d(TTTTTTTTTTTTTTTTTTTpT) (SEQ ID NO: 13) modified with N-phosphorylguanidine group.

Figure 3:
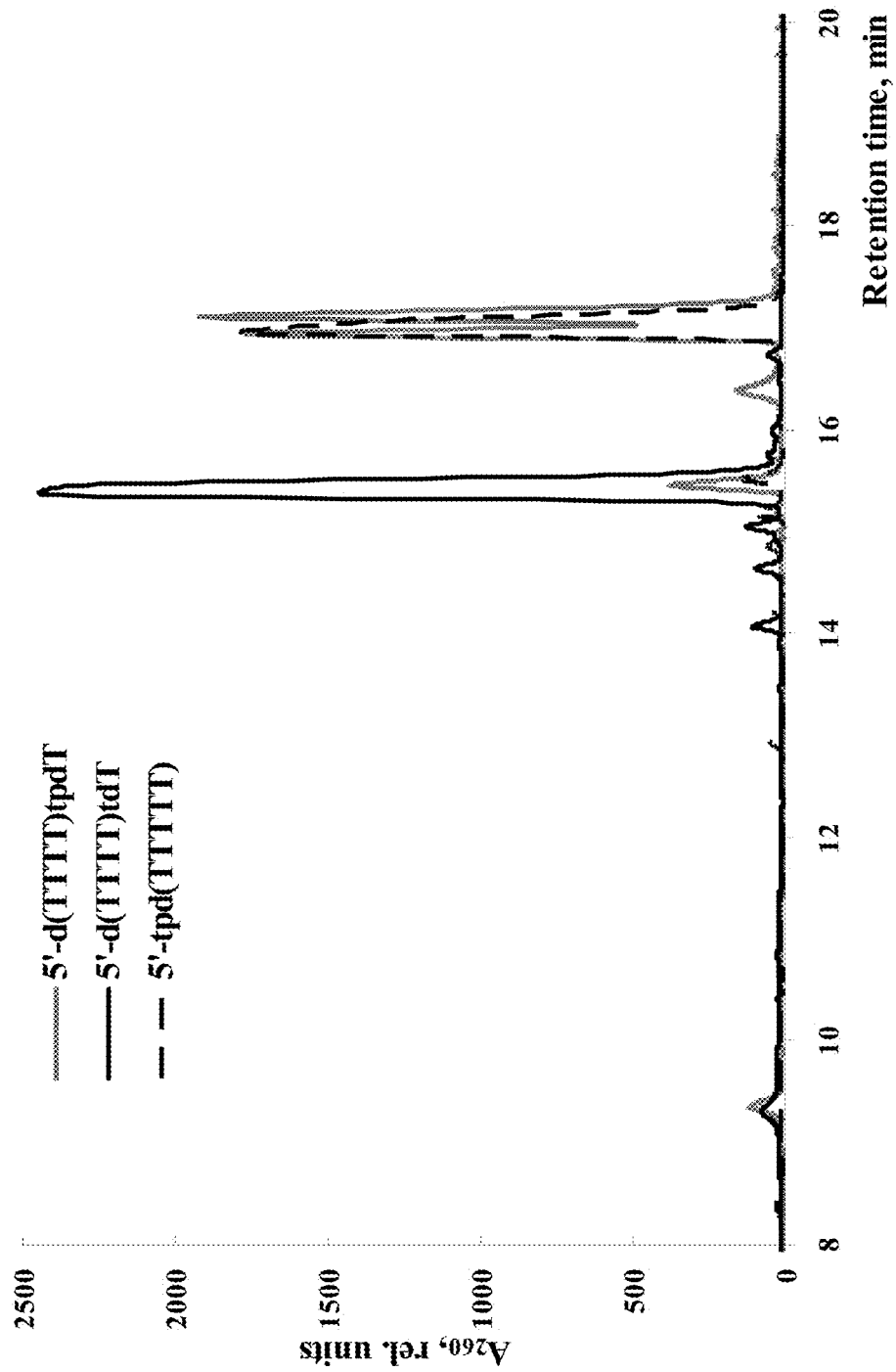

FIG. 3. RP-HPLC of oligodeoxyribonucleotides with an LNA nucleotide 5'-d(TTTT)tdT (thin black line), 5'-d(TTTT)tpdT (grey line) and 5'-tpd(TTTTT) (dashed line) modified with N,N,N',N'-tetramethyl-N"-phosphorylguanidine groups; t marks position of an LNA nucleotide.

Figure 4:
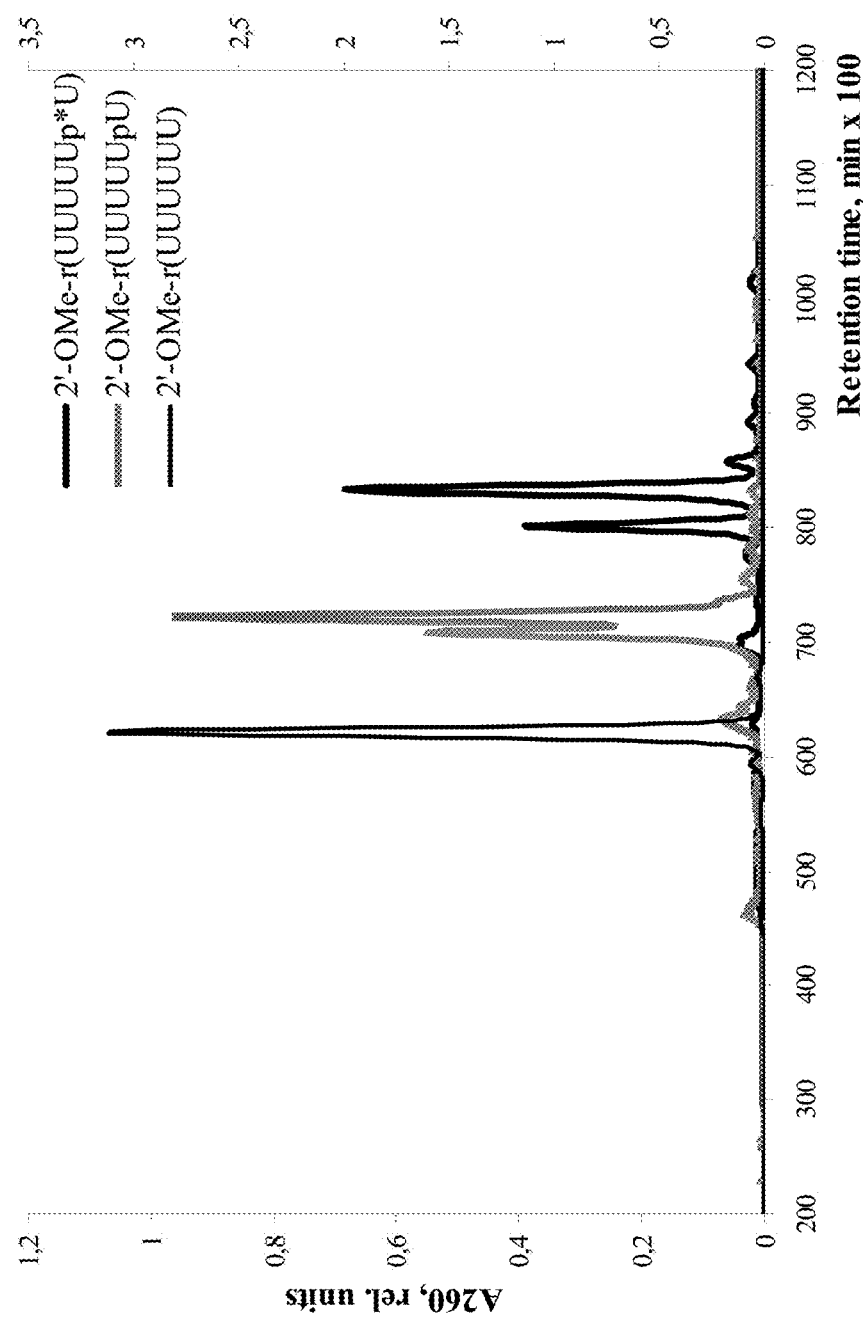

FIG. 4. RP-HPLC of oligo-2'-O-methylribonucleotides 5'-UUUUUp*U modified with a N,N'-bis(tetramethylene)-N"-phosphorylguanidine group (bold black line), 5'-UUUUUpU modified with a N,N'-dimethyl-N"-phosphorylimino-2-imidazolidine group (grey line), and an unmodified oligo-2'-O-methylribonucleotide 5'-UUUUUU (thin black line).

Figure 5:
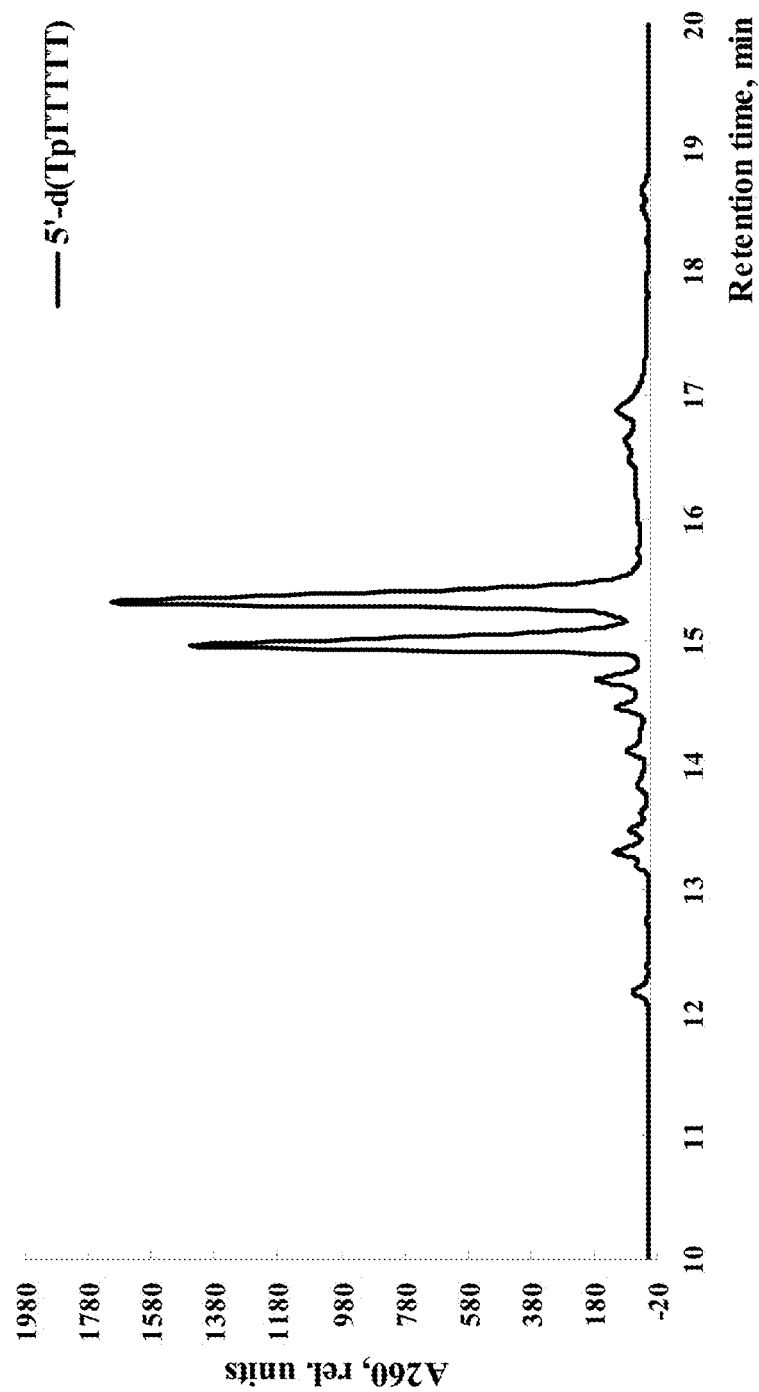

FIG. 5. RP-UPLC of an oligonucleotide 5'-d(TpTTTTT) modified with a N-cyanoiminophosphate group.

Figure 6:
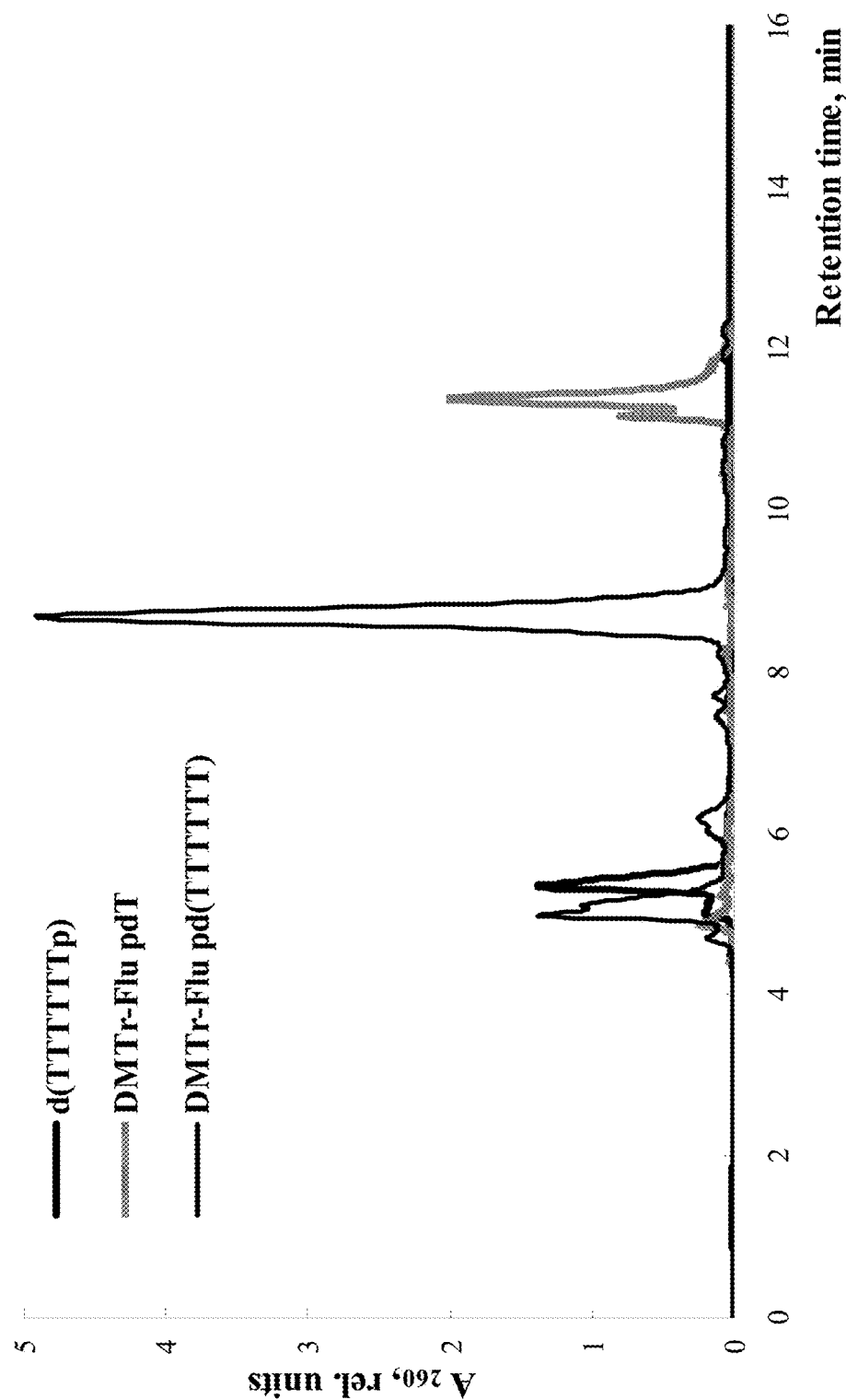

FIG. 6. RP-HPLC of oligonucleotides 5'-d(TTTTTT)p (bold black line), 5'-DMTr-Flu pd(TTTTTT) (thin black line) and a nucleotide 5'-DMTr-Flu pdT (grey line) modified with a N,N'-bis(tetramethylene)-N"-guanidinophosphate group.

Figure 7:
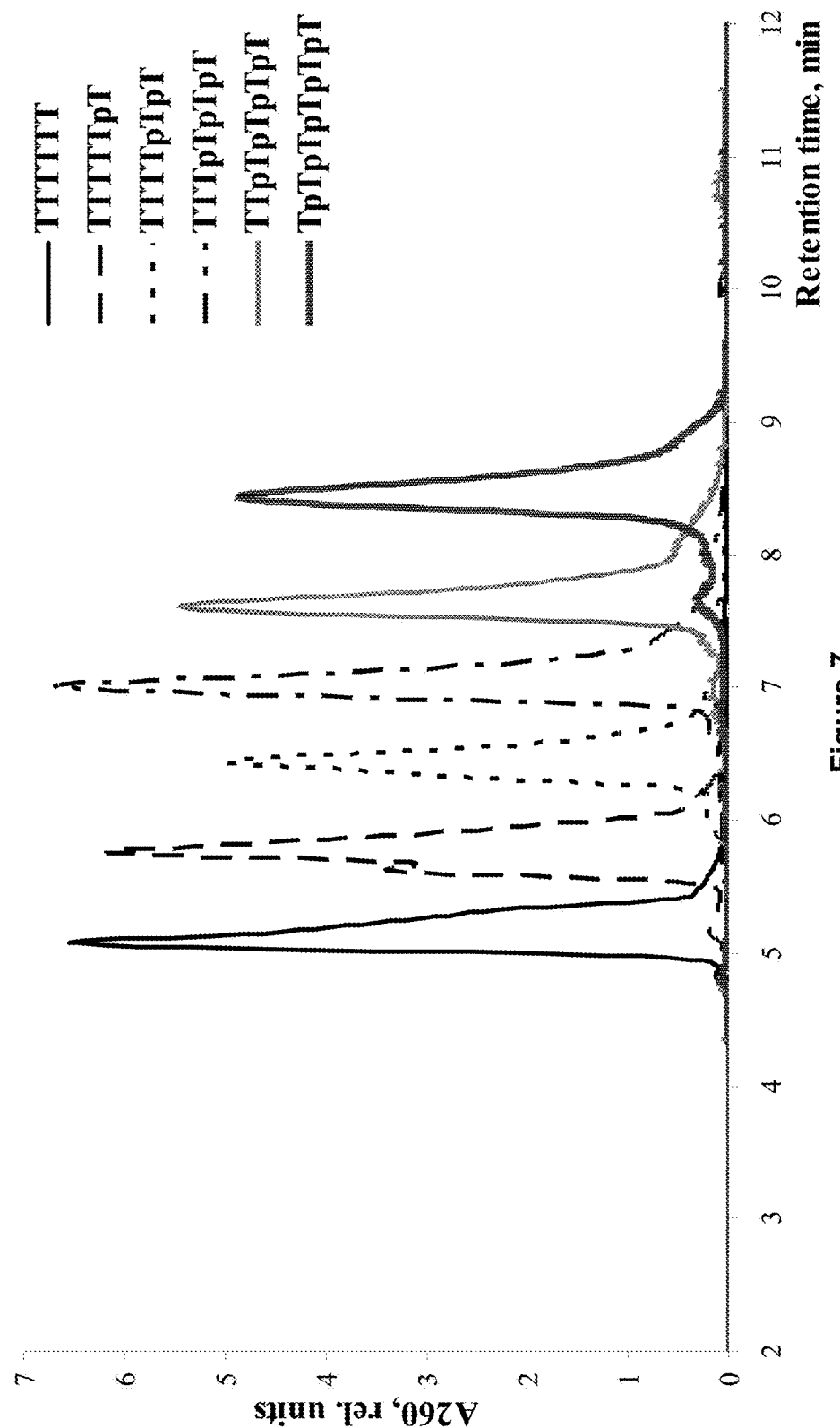

FIG. 7. RP-HPLC of oligonucleotides 5'-d(TTTTTpT), 5'-d(TTTTpTpT), 5'-d(TTTpTpTpT), 5'-d(TTpTpTpTpT) and 5'-d(TpTpTpTpTpT) modified with N,N'-dimethyl-N"-phosphorylimino-2-imidazolidine groups; p marks position of a modifying group.

Figure 8:
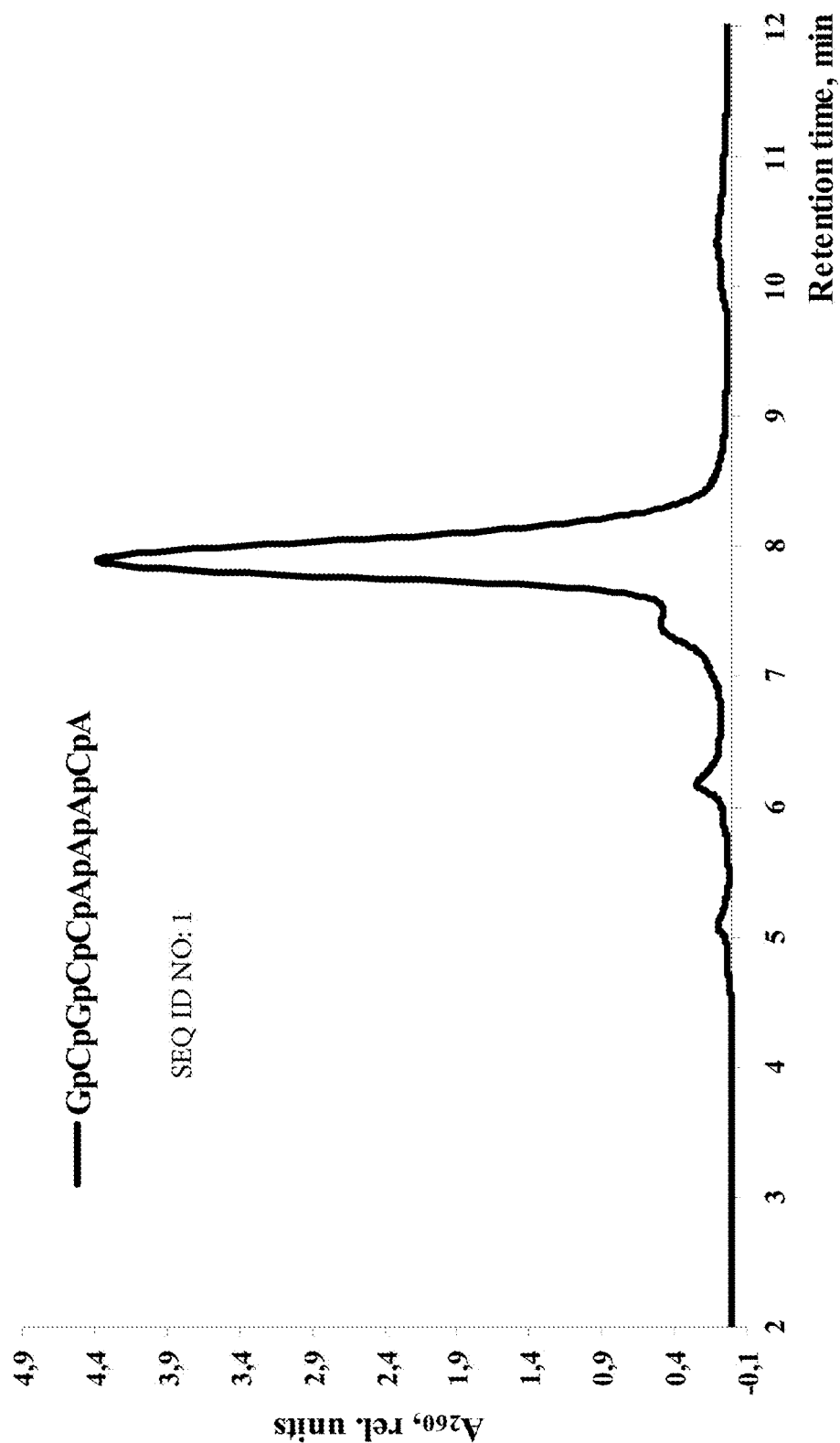

FIG. 8. RP-HPLC of an oligonucleotide 5'-d(GpCpGpCpCpApApApCpA)(SEQ ID NO: 1) fully modified with N,N'-dimethyl-N"-phosphorylimino-2-imidazolidine groups at all internucleoside positions.

ABBREVIATIONS AND NOTATION p—indicates the position of a modified phosphate group as described
t—indicates the position of an LNA-T nucleotide
a—indicates the position of an LNA-A nucleotide
c—indicates the position of an LNA-5-Me-C nucleotide
g—indicates the position of an LNA-G nucleotide
F—2-hydroxymethyl-3-hydroxytetrahydrofurane (apurinic/apyrimidinic site) phosphate
BHQ—BlackHole Quencher™
DD—1,12-dodecanediol phosphate
Flu—5(6)-carboxyfluorescein label
$N_s$—indicates the phosphorothioate residue of nucleotide "N"
BSA—N,O-bis(trimethylsilyl)acetamide
BSTFA—N,O-bis(trimethylsilyl)trifluoroacetamide
DIEA—N,N-diisopropylethylamine
NMI—N-methylimidazole
DMAP—4-dimethylaminopyridine
DBU—1,8-diazabicyclo[5.4.0]undec-7-ene
TMG—1,1,3,3-tetramethylguanidine

DETAILED DESCRIPTION

Phosphoryl guanidines are represented in Nature by such compounds as creatine phosphate and phosphoarginine. Synthetic low molecular weight phosphoryl guanidines have been known since at least 1960s [52]. Small molecule phosphoryl guanidines have found limited use as pesticides [53], flame retardants [54] and therapeutics [55]. Phosphoryl guanidine diesters form complexes with metal ions through guanidine nitrogen [56]. X-ray analysis of O,O'-diisopropyl phosphoryl guanidine has confirmed the presence of only the tautomer with the phosphorylimino group >P(=O)—N=C< in the crystal structure.

However, no nucleoside or oligonucleotide derivatives have been described until now, and their properties remained unknown. The present inventors have prepared first oligonucleoside phosphoryl guanidines by iodine oxidation of dithymidine β-cyanoethyl phosphite in the presence of N,N,N',N'-tetramethylguanidine (TMG) in pyridine using methodology similar to that previously described in relation to primary amines [57].

The present inventors have studied oxidation of CPG-bound 3',5'-dithymidine β-cyanoethyl phosphite, which is a common intermediate in solid-phase DNA synthesis according to the β-cyanoethyl phosphoramidite method [58]. As described herein, oxidation of the above phosphite by 0.1 M solution of iodine in dry pyridine in the presence of 1 M TMG and 20% N,O-bis(trimethylsilyl)acetamide produced 3',5'-dithymidine-N,N,N',N'-tetramethyl phosphoryl guanidine as a major product. The oligonucleotide 5'-d(TTTTTpT), where p indicates position of the modified phosphate group, was isolated after concentrated aqueous ammonia treatment for 1 h at ambient temperature as a mixture of two diastereomers (Example 1.1). The only byproduct that was isolated was $dT_6$, which is the likely result of concurrent hydrolysis of a reactive iodophosphonium intermediate by traces of moisture. The inventors have concluded that the phosphoryl guanidine group is stable during solid-phase oligonucleotide synthesis and ammonia deprotection at pH 11.

The integrity of the oligothymidine monophosphoryl guanidine was confirmed by MALDI-TOF MS. Its mobility during gel electrophoresis in 20% polyacrylamide gel was lower than for dT6, suggesting charge neutral character of the tetramethyl phosphoryl guanidine group at pH 7.4, which corresponds to the literature data for low molecular weight phosphoryl guanidines [59].

Through synthesis of 20-mer oligothymidylates with one tetramethyl phosphoryl guanidine group, the inventors have noted that the yields progressively worsen with increased from the support in a row 5'-d($T_{18}$TpT)>5'-d($T_{10}$Tp$T_9$)>5'-d(TTp$T_{18}$). The oligothymidylates obtained were used to ascertain the influence of the single tetramethyl phosphoryl guanidine group on thermal stability of the complementary duplex with oligonucleotide 5'-d($C_2A_{20}C_2$) as compared to unmodified $dT_{20}$.

The inventors have also successfully obtained oligonucleotides with unsubstituted phosphoryl guanidine group. Oxidation of CPG-bound 3',5'-dithymidine β-cyanoethyl phosphite by 0.1 M iodine solution in pyridine in the presence of 0.5 M guanidine hydrochloride, 0.5 M 1,8-diazabicyclo [5.4.0]undec-7-ene (DBU) and 20% BSA followed by oligonucleotide synthesis produced a hexathymidylate with phosphoryl guanidine group as a major product together with the $dT_6$ hydrolysis product (Example 5).

Analogously, iodine oxidation of the dithymidine phosphite in the presence of formamidine hydrochloride, DBU and BSA in pyridine followed by oligonucleotide synthesis resulted in the formation of hexathymidine phosphoryl formamidine, which is a representative of another class of phosphorylimino compounds: phosphoryl amidines (Example 39).

Oxidation of CPG-bound 3',5'-dithymidine β-cyanoethyl phosphite by 0.1 M iodine solution in pyridine in the presence of 0.5 M O-methylisourea hydrogen sulfate, 1 M DBU and 20% BSA followed by oligonucleotide synthesis and deprotection by concentrated aqueous ammonia for 1 h at ambient temperature has resulted in a mixture of products containing $dT_6$, oligonucleoside O-methyl phosphoryl isourea and phosphoryl guanidine according to MALDI-TOF MS (Example 7). The latter is likely formed through substitution of the methoxy group of phosphoryl isourea by ammonia. Additional ammonia treatment at 55° C. for 16 h resulted in the increase of the amount of phosphoryl guanidine and the decrease of the amount of O-methyl phosphoryl isourea. Likewise, treatment of the mixture with ethylenediamine in ethanol (1:1 v/v) at 55° C. for 16 h resulted in disappearance of O-methyl phosphoryl isourea and afforded N-β-aminoethyl phosphoryl guanidine as the major product (Example 8). This opens the way to substituting positively charged groups for negatively charged phosphates in oligonucleotide sequences as the N-β-aminoethyl phosphoryl guanidine group should be positively charged at physiological pH. Cationic oligonucleoside phosphoryl guanidines may potentially exhibit improved cell uptake and in vivo delivery in the absence of external transfection agents.

As described herein, the present inventors have obtained 20-mer oligothymidylates with a single unsubstituted phosphoryl guanidine group (FIG. 2). The yields decreased with the length of oligonucleotide in a row $d(T_{18}TpT) > d(T_{10}TpT_9) > d(TTpT_{18})$. Oligonucleotides with two and three phosphoryl guanidine groups were also prepared; however, the reactions resulted in mixtures of products that were difficult to separate, leading the inventors to conclude that iodine oxidation chemistry is most effective for the preparation of monosubstituted oligonucleotides.

H-Phosphonate chemistry can be used to prepare oligonucleotides with two and three modifications [63], as described herein. CPG-supported 3',5'-dithymidine-H-phosphonate can be oxidised into N,N,N',N'-tetramethyl phosphoryl guanidine either by 0.1 M iodine and 20% vol. TMG in pyridine with or without BSA (Examples 1.2 and 1.3) or by $CCl_4$ or $CCl_3Br$ and 20% vol. TMG in pyridine (Examples 1.4 and 1.5) [64]. The conversion in the case of iodine (70-75%) was higher than in the case of $CCl_4$ or $CCl_3Br$ (10-20%). In the presence of BSA the conversion increased to 80-85%. After solid-phase synthesis using the phosphoramidite method, a hexathymidylate 5'-d(TTTTTpT) with tetramethyl phosphoryl guanidine group was obtained in good yield together with byproducts $dT_5$ and $dT_6$ (Example 1.3). The inventors have successfully obtained di- and trisubstituted phosphoryl guanidines 5'-d(TTTTpTpT) (Example 3.1) and 5'-d(TTTpTpTpT) (Example 4.1) via iodine/TMG/BSA oxidation, but in the latter case the yield was lower.

To increase the yield of oligonucleoside phosphoryl guanidines, the inventors explored a novel reaction between CPG-bound dinucleoside β-cyanoethyl phosphite and tetraalkyl azidocarbenium salts in N,N-dimethylformamide or acetonitrile with or without BSA. The reaction may occur at ambient temperature or at 40-45° C. Addition of 5% triethylamine as well as BSA increases yield. The method proved to be effective for the preparation of oligonucleotides with multiple tetraalkyl phosphoryl guanidino groups (FIG. 1). An automated version of the method on a DNA synthesiser was used to produce fully modified oligonucleoside phosphoryl guanidines (Example 47).

Along with charge neutral or cationic phosphoryl guanidines, the inventors have also prepared oligonucleotides containing an ionisable N-cyanoimino phosphate group. In that case, a CPG-bound dinucleoside phosphite was reacted with 0.25 M solution of cyanogen azide in acetonitrile at ambient temperature. The results suggest that the yield of the oligonucleotide depends on the deprotection method used. Good results were obtained when a mixture of ethylenediamine and ethanol (1:1 v/v) [65] was substituted for aqueous ammonia and used to deprotect the oligonucleotide with N-cyanoimino phosphate group for 1 h at 70° C. (Examples 40 and 41).

Electrophoretic mobility of the obtained N-cyanoimino hexathymidylates 5'-d(TTTTTpT) and 5'-d(TpTTTTT) was very similar to $dT_6$, which suggests that N-cyanoimino group has negative charge at physiological pH. The oligonucleotides were only slightly hydrophobic than the unmodified hexathymidylate. Two diastereomers were observed on RP-HPLC trace (FIG. 5).

A range of modified oligonucleotides were found to be compatible with phosphoryl guanidine modifications, in particular ribonucleotide derivatives such as oligo-2'-O-methylribonucleotides (FIG. 4), LNA (FIG. 3) and RNA itself (Example 46). Phosphorothioate groups can be successfully incorporated into oligonucleotides together with phosphoryl guanidine groups (Examples 32-35). A range of other modifications such as fluorescein, abasic site, non-nucleosidic insert or BlackHole quencher were tolerated. Mononucleotides with either 3'- or 5'-phosphoryl guanidine groups were also prepared (Examples 42 and 44, FIG. 6).

Definitions

The term "nucleotide" refers to a compound containing a nucleoside or a modified nucleoside and at least one phosphate group or a modified phosphate group linked to it by a covalent bond. Exemplary covalent bonds include, without limitation, an ester bond between the 3', 2' or 5' hydroxyl group of a nucleoside and a phosphate group.

The term "oligonucleotide" refers to a compound containing two or more nucleotides joined together in a polymeric chain. Oligonucleotides may be deoxyribonucleic acids or ribonucleic acids. Oligonucleotides may be single stranded or double stranded. In the case of double stranded oligonucleotides one or both strands may contain a modified phosphate according to the present invention.

An oligonucleotide may be a polymer of two or more nucleotides, but may have any length. For example, an oligonucleotide may have a minimum length of one of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides. Optionally it may have a maximum length of one of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 nucleotides, although longer oligonucleotides are also provided in some embodiments. Purely, by way of example an oligonucleotide having one of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides is provided.

In oligonucleotides of the present invention one, several (e.g. 2, 3, 4, 5, 6, 7, 8, 9, 10 or more) or each nucleotide may contain a modified phosphate according to the present invention.

The nucleotides and oligonucleotides of the present invention may include chemical modifications as described herein such as a chemical substitution at a sugar position, a phosphate position, and/or a base position of the nucleic acid including, for example, incorporation of a modified nucleotide, incorporation of a capping moiety (e.g. 3' capping), conjugation to a high molecular weight, non-immunogenic compound (e.g. polyethylene glycol (PEG)), conjugation to a low molecular weight compound (e.g. cholesterol), conjugation to a peptide (e.g. a cell-penetrating peptide), substitutions in the phosphate group (e.g. phosphorothioate). Base modifications may include 5-position pyrimidine modifications, modifications at exocyclic amines, substitution of 4-thiouridine, substitution of 5-bromo- or 5-iodouracil, backbone modifications. Sugar modifications may include 2'-amino nucleotides (2'-NH$_2$), 2'-fluoro nucleotides (2'-F), 2'-O-methyl (2'-OMe) nucleotides, 2'-O-allyl nucleotides, 2'-O-β-methoxyethyl nucleotides, "locked" nucleotides (e.g. LNA) or tricyclo-DNA nucleotides. The bonds between the central phosphorus atom of a phosphate and the or each nucleoside are suitably via oxygen, that is, the 3' and or 5' end of the nucleoside is an alcohol. However, nucleoside analogues in which the 3' and or 5' end of the nucleoside is not an alcohol, but rather a suitable analogue, are also envisaged. For example, the 3' and/or 5' end of a nucleoside may be a thiol, a selenol, or an amine.

Nucleotides and oligonucleotides according to the present invention may be provided in isolated or purified form.

The term "nucleoside" refers to a compound containing a sugar part and a nucleobase. Exemplary sugars include, without limitation, ribose, 2-deoxyribose, arabinose and the like. Exemplary nucleobases include, without limitation, thymine, uracil, cytosine, adenine, guanine, purine, hypoxanthine, xanthine, 2-aminopurine, 2,6-diaminopurine, 5-methylcytosine, 4-fluorouracil, 5-chlorouracil, 5-bromouracil, 5-iodouracil, 5-trifluoromethyluracil, 5-fluorocytosine, 5-chlorocytosine, 5-bromocytosine, 5-iodocytosine, 5-propynyluracil, 5-propynylcytosine, 7-deazaadenine, 7-deazaguanine, 7-deaza-8-azaadenine, 7-deaza-8-azaguanine, isocytosine, isoguanine and the like.

The term "nucleoside analogues" as used herein refers to a modified nucleoside in which the sugar part is replaced with any other cyclic or acyclic structure. Exemplary nucleoside analogues in which the sugar part is replaced with another cyclic structure include, without limitation, monomeric units of morpholinos (PMO) and tricyclo-DNA. Exemplary nucleoside analogues in which the sugar part is replaced with an acyclic structure include, without limitation, monomeric units of peptide nucleic acids (PNA) and glycerol nucleic acids (GNA).

The term "nucleoside analogue" additionally refers to a nucleoside any part of which is replaced by a chemical group of any nature. Exemplary such nucleosides analogues include, without limitation, 2'-substituted nucleosides such as 2'-fluoro, 2-deoxy, 2'-O-methyl, 2'-O-β-methoxyethyl, 2'-O-allylriboribonucleosides, 2'-amino, locked nucleic acid (LNA) monomers and the like.

Suitably, nucleoside analogues may include nucleoside analogues in which the sugar part is replaced by a morpholine ring as depicted below.

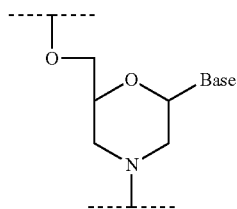

In structures of this type, it will be appreciated that the labels 3' and 5', as applied to conventional sugar chemistry, apply by analogy. That is, in the structure depicted, the hydroxylmethyl substituent on the ring is considered the 5' end, while the third nitrogen valency is considered the 3' end.

The term "oligonucleotide analogue" as used herein refers to a modified oligonucleotide, which is chemically modified at either its phosphate groups or has its nucleosides replaced by nucleoside analogues. Exemplary oligonucleotide analogues include, without limitation, phosphorothioate oligonucleotides (PS), phosphorodiamidate morpholino oligonucleotides (morpholinos, PMO), tricyclo-DNA and peptide nucleic acids (PNA).

The term "peptide nucleic acid" relates usually to oligonucleotide analogues that substitute peptide bond for phosphate group. However, as used herein, it includes compounds that may incorporate modified phosphate groups according to the present invention. It is understood that those compounds would also be covered by the present application.

The term "phosphate group" as used herein refers to phosphoric acid $H_3PO_4$ wherein any hydrogen atoms are replaced by one, two or three organic radicals to give a phosphoester, phosphodiester, or phosphotriester, respectively.

The term "modified phosphate group" refers to a phosphate group wherein any oxygens connected to the phosphorus atom are replaced by a chemical group of any nature. Suitable replacements may include sulfur, selenium, imino (NR) and borane (—BH$_3^-$). For example, the group may be a phosphorothioate group, a phosphoroselenoate or boranophosphate group. Preferably, the "modified phosphate group" is a phosphorothioate group.

It will be appreciated that, depending on their substitution, the phosphates and modified phosphates described herein may be chiral. Where stereochemistry is not indicated, the structure encompasses both Rp and Sp configurations, each in isolation and as mixtures thereof (for example, a racemic mixture). For example, and not by way of limitation, the structure:

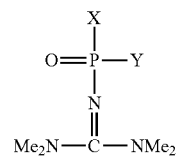

as depicted encompasses

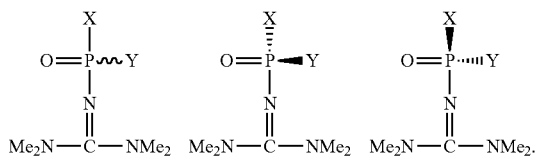

It will be appreciated that compounds described herein may contain more than one chiral centre. Except where indicated otherwise, it is intended that all enantiomers and diastereomers are encompassed.

The term "protected oligonucleotide" as used herein refers to an oligonucleotide, which incorporates one or more protecting groups.

The term "deprotected oligonucleotide" as used herein refers to an oligonucleotide from which one or more protecting groups have been removed.

It will be understood that references to nucleosides, nucleotides, and oligonucleotides include protected forms thereof.

The term "protecting group" refers to a chemical group that is used to block temporarily a reactive site in a compound. A protecting group is removed under specific conditions. Exemplary protecting groups include, without limitation, acetyl (Ac), benzoyl (Bz), isobutyryl (Ibu), tert-butylphenoxyacetyl (Tac), levulinyl (Lev), methyl (Me), 2-cyanoethyl (CE), allyl (All), 2-chlorophenyl (o-ClPh), 4,4'-dimethoxytrityl (DMTr), 4-methoxytrityl (MMTr), tert-butyldimethylsilyl (TBDMS), triisopropylsilyloxymethyl (TOM) and the like.

The term "linker" as used herein encompasses a chemical group that connects a compound to a solid support and is cleavable under specific conditions releasing said compound from said solid support. Exemplary linkers used in solid-phase oligonucleotide synthesis include, without limitation, succinyl, diglycolyl, oxalyl, hydroquinone-O,O'-diacetyl (Q-linker), phthaloyl, 4,5-dichlorophthaloyl, malonyl, glutaryl, diisopropylsilyl, 1,1,3,3-tetraisopropyldisiloxane-1,3-diyl and the like.

Other linkers may include non-nucleotide chemical groups inserted into an oligonucleotide or modified oligonucleotide ("internucleoside/internucleotide linkers"), or non-nucleotide chemical groups forming a link between a nucleotide and another chemical moiety, for example a label or quencher. Suitable linkers are known in the art and include 1,12-dodecanediol phosphate (DD).

The term "solid support" refers to a polymeric support used in solid-phase oligonucleotide synthesis. Exemplary solid supports include, without limitation, controlled pore glass (CPG), polystyrene resin, TentaGel® resin, TSK Gel® Toyopearl® resin, poly(vinyl alcohol) resin and the like. The term "solid support" as used herein also refers to non-resin types of solid supports used, for example, in multiple oligonucleotide synthesis including, without limitation, filter discs, multipin systems, multiwell plates and the like.

The term "organic radical" as used herein refers to a chemical group, which contains one or more carbon atoms connected to any other atoms, with a free valency at carbon. Examples of other atoms include, without limitation, hydrogen, nitrogen, oxygen, fluorine, silicon, phosphorus, sulphur, chlorine, bromine and iodine.

The term alkyl as used herein refers to both straight and branched chain cyclic and acyclic forms. The term "alkyl" includes monovalent, straight or branched, saturated, acyclic hydrocarbyl groups. $C_{1-4}$alkyl groups include, without limitation, methyl, ethyl, n-propyl, i-propyl or t-butyl groups.

The term "alkenyl" includes monovalent, straight or branched, unsaturated, acyclic hydrocarbyl groups having at least one carbon-carbon double bond and, in some embodiments, no carbon-carbon triple bonds. In some embodiments alkenyl is $C_{2-10}$alkenyl, in some embodiments $C_{2-6}$alkenyl, in some embodiments $C_{2-4}$alkenyl.

The term "alkynyl" includes monovalent, straight or branched, unsaturated, acyclic hydrocarbyl groups having at least one carbon-carbon triple bond and, in some embodiments, no carbon-carbon double bonds. In some embodiments, alkynyl is $C_{2-10}$alkynyl, in some embodiments $C_{2-6}$alkynyl, in some embodiments $C_{2-4}$alkynyl.

The term "heterocyclic compound" refers to a compound comprising a heterocyclic group. The term "heterocyclic group" refers to group a saturated, partially unsaturated or unsaturated (e.g. aromatic) monocyclic or bicyclic group containing one or more (for example 1, 2, 3, 4 or 5) ring heteroatoms selected from O, $S(O)_t$ (wherein t is 0, 1, or 2) or N and includes unsubstituted groups and groups substituted with one or more substituents (for example 1, 2, 3, 4 or 5 substituents), optionally wherein the one or more substituents are taken together to form a further ring system. Unless stated otherwise herein, where a heterocyclic group is bonded to another group, the heterocyclic group may be C-linked or N-linked, i.e. it may be linked to the remainder of the molecule through a ring carbon atom or through a ring nitrogen atom (i.e. an endocyclic nitrogen atom). The term heterocyclic group thus includes optionally substituted heterocycloalkyl, heterocycloalkenyl and heteroaryl groups as defined herein.

The term "aryl" includes monovalent, aromatic, cyclic hydrocarbyl groups, such as phenyl or naphthyl (e.g. 1-naphthyl or 2-naphthyl). In general, the aryl groups may be monocyclic or polycyclic fused ring aromatic groups.

The term "heteroaryl" includes aryl groups in which one or more carbon atoms are each replaced by heteroatoms independently selected from O, S, N and $NR^N$, where $R^N$ is defined herein.

The term "halogen" refers to —F, —Cl, —Br, and —I. In some embodiments, the halogen is —F, —Cl, or —Br. In some embodiments, the halogen is —F or —Cl, for example, Cl.

In general, the heteroaryl groups may be monocyclic or polycyclic (e.g. bicyclic) fused ring heteroaromatic groups. Typically, heteroaryl groups contain 5-10 members wherein 1, 2, 3 or 4 ring members are independently selected from O, S, N and $NR^N$.

As used herein, the term "optionally substituted" refers to a substituent that may be substituted with one or more (up to the maximum number of free valencies on that substituent) substituents. The substituents may be selected from:

$C_{1-4}$alkyl,
—F, —Cl, —Br, —I
—$CF_3$, —$OCF_3$, —$SCF_3$,
—OH, -L-OH, —O-L-OH, —NH-L-OH, —$NR^{30}$-L-OH, —$NR^{30}$-L-O
—SH,
—CN,
—$NH_2$, —$NHC_{1-4}$alkyl, —$N(C_{1-4}$alkyl$)_2$,
-L-$NH_2$, -L-$NHC_{1-4}$alkyl,
—OC(O)$C_{1-4}$alkyl,
—C(O)OH, —C(O)O$C_{1-4}$alkyl,
—C(O)$C_{1-4}$alkyl,
—C(O)$NH_2$, —C(O)NH$C_{1-4}$alkyl, —C(O)N($C_{1-4}$alkyl$)_2$, —NHC(O)$C_{1-4}$alkyl, —N($C_{1-4}$alkyl)C(O) $C_{1-4}$alkyl; and =O;

wherein each -L- is a bond or a $C_{1-4}$ alkylene and $R^{30}$ is —$C_{1-10}$ alkyl, —$C_{2-10}$alkenyl, —$C_{2-10}$alkynyl, —$C_{6-10}$aryl, or —$O_{5-10}$heteroaryl.

In some embodiments, these optional substituents are selected from —$C_{1-4}$alkyl, —F, —Cl, —$CF_3$, —OH, —$OC_{1-4}$alkyl, —$NH_2$, —$NHC_{1-4}$alkyl, and —N($C_{1-4}$alkyl)$_2$.

The term "ambient temperature" as used herein refers to temperatures in the range of 15-29° C., preferably in the range of 20-25° C.

Reactions

As described herein, a particular advantage of the modified phosphate moieties of the present invention is the convenient incorporation of these moieties as demonstrated by the present inventors. For example, a modified phosphate moiety of Formula VI can be readily incorporated into an oligonucleotide during sequential oligonucleotide synthesis based on H-phosphonate or phosphoramidite chemistry. Accordingly, the present invention provides methods of synthesising the compounds of the present invention. These methods may use solid-supported reagents, and may be performed in a DNA synthesizer.

It will be appreciated that phosphoryl isoureas, phosphoryl isothioureas, phosphoryl imidates and phosphoryl imidothioates are, inter alia, reactive intermediates, which upon reaction with primary or secondary amines can be converted into phosphoryl guanidines or phosphoryl amidines as described herein (see, for example, Examples 7 and 8). Accordingly, the present invention also provides a method of synthesizing a compound as described herein having a phosphoryl guanidine or phosphoryl amidine group, the method comprising reactioning a compound as described herein having a phosphoryl isourea, phosphoryl isothiourea, phosphoryl imidate or phosphoryl imidothioate group with a primary or secondary amine.

H-Phosphonate Chemistry

H-Phosphonate chemistry is a convenient and established method of chemical oligonucleotide synthesis. Suitably, a 5'-DMT-protected nucleotide affixed via a linker to a solid support undergoes sequential deprotection then coupling reaction with an H-phosphonate monoester to form an H-phosphonate diester. Further nucleoside units may be added in sequence, following the steps of detritylation then coupling, with oxidation of the internucleosidic H-phosphonate diester linkages to phosphodiester linkages occurring at the end of the assembly with an oxidant, typically iodine.

The present inventors have shown, as described herein, that the modified phosphate groups of the invention can be readily incorporated into oligonucleotides assembled using H-phosphonate chemistry. To incorporate a modified phosphate, as described herein, the oxidation may be performed in the presence of a suitable guanidine, amidine, isourea, isothiourea, imidate or imidothioate which may be present as a free base or in its salt form, for example, as a hydrochloride or other salt, with a suitable oxidant. Suitable oxidants include iodine $I_2$, bromine $Br_2$, chlorine $Cl_2$, iodine chloride ICl, N-bromosuccinimide, N-chlorosuccinimide, N-iodosuccinimide, carbon tetrachloride $CCl_4$, bromotrichloromethane $CCl_3Br$, tetrabromomethane $CBr_4$, tetraiodomethane $CI_4$, iodoform $CHI_3$, hexachloroethane $C_2Cl_6$, and hexachloroacetone $(CCl_3)_2CO$. A preferred oxidant is iodine.

Of course, it will be appreciated that after oxidation to incorporate one or more modified phosphate groups, the cycle of detritylation followed by coupling can resume, with further oxidation steps performed at appropriate points during chain assembly. In this way, modified phosphate groups according to the invention can be incorporated at appropriate points during the chain assembly.

A variety of solvents known in the art may be used including pyridine, 2-picoline, 3-picoline, 4-picoline, quinoline, tetrahydrofuran (THF), 1,4-dioxane, 1,2-dimethoxyethane (DME), acetonitrile. Pyridine is a preferred solvent.

It may be preferable to include a base during the oxidation step. Suitably, the base is an amine base, for example, triethylamine, N,N-diisopropylethylamine (DIEA), N-methylmorpholine, N-ethylmorpholine, tributylamine, 1,4-diazabicyclo[2.2.2]octane (DABCO), N-methylimidazole (NMI), pyridine, 2,6-lutidine, 2,4,6-collidine, 4-dimethylaminopyridine (DMAP), 1,8-bis(dimethylamino)naphthalene ("proton sponge"), 1,8-diazabicyclo[5.4.0]undec-7-ene (DBU), 1,5-diazabicyclo[4.3.0]non-5-ene (DBN), 7-methyl-1,5,7-triazabicyclo[4.4.0]dec-5-ene (MTBD), 2-tert-butyl-1, 1,3,3-tetramethylguanidine, 2,8,9-trimethyl-2,5,8,9-tetraaza-1-phosphabicyclo[3.3.3]undecane or phosphazene base. For example, the base may be triethylamine or DBU.

The present inventors have found that addition of a silylating reagent during the oxidation step incorporating the modified phosphate motif(s) may be desirable. Accordingly, N,O-bis(trimethylsilyl)acetamide (BSA), N,O-bis(trimethylsilyl)trifluoroacetamide (BSTFA), chlorotrimethylsilane, bromotrimethylsilane, iodotrimethylsilane, triethylsilyl chloride, triphenylsilyl chloride, hexamethyldisilazane, trimethylsilyl trifluoromethanesulfonate (TMSOTf), dimethylisopropylsilyl chloride, diethylisopropylsilyl chloride, tert-butyldimethylsilyl chloride, tert-butyldiphenylsilyl chloride, triisopropylsilyl chloride, dimethyldichlorosilane, diphenyldichlorosilane or similar may be added. A preferred silylating reagent is N,O-bis(trimethylsilyl)acetamide (BSA).

Phosphoramidite Chemistry

Phosphoramidite chemistry is also an attractive method of chemical oligonucleotide synthesis. The cycle associated with phosphoramidite chemistry-based oligonucleotide chemistry is known in the art. In brief, a solid supported nucleotide is detritylated, then coupled with a suitably activated nucleoside phosphoramidite to form a phosphite triester linkage. Capping may then occur, followed by oxidation of the phosphite triester with an oxidant, typically iodine. The cycle is then repeated to assemble the chain.

The present inventors have found, as described herein, that performing such an oxidation step in the presence of a suitable guanidine, amidine, isourea or isothiourea, which may be present in its salt form, for example, as a hydrochloride salt, can be used to produce the desired modified phosphate group(s). Removal of the β-cyanoethyl phosphite protecting group completes the synthesis. As described above for the oxidation step in the H-phosphonate method, the inclusion of bases and/or silylating agents may be desirable.

Use of Organic Azides

Also described herein is a novel reaction to obtain modified phosphate groups of the invention though reaction of a dinucleoside β-cyanoethyl phosphite and a suitable organic azide, optionally in the presence of a silylating agent such as BSA. A base, for example an amine base, for example triethylamine, may be included.

The present inventors have shown that this method is effective for the preparation of oligonucleotides with various phosphoryl guanidine substitution pattern such as having unsubstituted, mono-, di-, tri-, and tetra-substituted phosphoryl guanidine groups, and for oligonucleotides having multiple modified phosphate groups of this type.

Suitably, the organic azide can be an azide of formula $R^1—C^+(N_3)—R^2$ such as a bis(disubstituted amino)-1-azidocarbenium salt, a 1-(disubstituted amino)-1-azidocarbamidinium salt and the like, or a 1-(disubstituted amino)-1-azido-ethene, an N-substituted-1-azidocarbamidine; or an azide of formula is $(N_3)_2C=NR^2$, $(N_3)_2C=N^+R^{1A}R^{1B}$, or cyanogen azide $N_3—CN$. The organic azide may be prepared using methods known in the art. For example, tetraalkyl ureas can be converted to azidobis(dialkylamino)carbenium salts [60], dialkyl amides can be converted to N,N-dialkyl-azidocarbamidinium salts [61] whilst trialkyl ureas or monoalkyl amides can afford neutral azides [62].

Suitably, the organic azide may be selected from:

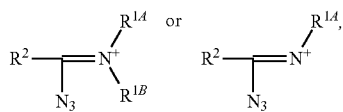

wherein $R^1$, $R^2$, $R^{1B}$, $R^{2A}$, and $R^{2B}$ are as defined herein. In some embodiments, $R^2$ may additionally be —$N_3$.

For example, the azide may be selected from:

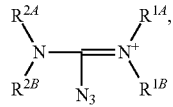

wherein each $R^{1A}$, $R^{1B}$, $R^{2A}$, $R^{2B}$ is independently —H or optionally substituted $C_{1-10}$ alkyl, —$C_{2-10}$alkenyl, —$C_{2-10}$alkynyl, —$C_{6-10}$aryl, or —$C_{5-10}$heteroaryl; and/or optionally wherein $R^{1A}$ and $R^{2A}$ together form an alkylene or heteroalkylene chain of 2-4 atoms in length; optionally wherein $R^{1A}$ and $R^{2A}$ together form —$CH_2$—$CH_2$— and $R^{1B}$ and $R^{2B}$ are each independently selected from —H and methyl.

optionally wherein $R^{1A}$ and $R^{1B}$, together with the atom to which they are bound, form a 5-8 membered heterocycle; or optionally wherein $R^{2A}$ and $R^{2B}$, together with the atom to which they are bound, form a 5-8 membered heterocycle, optionally a pyrrolidine;

or

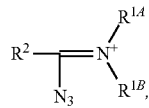

wherein each $R^{1A}$ and $R^{1B}$ is independently —H or optionally substituted $C_{1-10}$ alkyl, —$C_{2-10}$alkenyl, —$C_{2-10}$alkynyl, —$C_{6-10}$aryl, or —$C_{6-10}$heteroaryl; or $R^{1A}$ and $R^{1B}$, together with the atom to which they are bound, form a 5-8 membered heterocycle, and $R^2$ is selected from —H, —F, —OPG, —Cl, —Br, —I, —CN, —$N_3$, —SPG, and —S—$C_{1-10}$alkyl, wherein PG is a protecting group.

In some preferred reactions, the organic azide is:

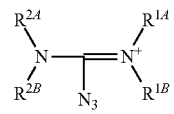

with a suitable counterion, for example, chloride.

Suitable counterions include, without limitation, chloride $Cl^-$, bromide $Br^-$, iodide $I^-$, triflate (trifluoromethanesulfonate) $CF_3SO_3^-$, p-toluenesulphonate $C_7H_7SO_3^-$, dichlorophosphate $PO_2Cl_2^-$, perchlorate $ClO_4^-$, tetrafluoroborate $BF_4^-$, tetraphenylborate $BPh_4^-$, hexafluorophosphate $PF_6^-$ and the like.

In some embodiments, each of $R^{1A}$, $R^{1B}$, $R^{2A}$, and $R^{2B}$ is independently —H or optionally substituted $C_{1-10}$alkyl, for example, H or optionally substituted $C_{1-4}$alkyl, for example, —H or methyl. In some embodiments, each of $R^{1A}$, $R^{1B}$, $R^{2A}$ and $R^{2B}$ is methyl; that is, the resultant phosphate is modified with a tetramethyl guanidine.

In some embodiments, $R^{1A}$ and $R^{2A}$ together form an alkylene or heteroalkylene chain of 2-4 atoms in length and $R^{1B}$ and $R^{2B}$ are each independently selected from —H and —$C_{1-4}$alkyl. In some embodiments, $R^{1A}$ and $R^{2A}$ together form —$CH_2$—$CH_2$—. In some embodiments, $R^{1A}$ and $R^{2A}$ together form —$CH_2$—$CH_2$— and $R^{1B}$ and $R^{2B}$ are —H or methyl.

In some embodiments, $R^{1A}$ and $R^{1B}$, together with the atom to which they are bound, form a 5-8 membered heterocycle, preferably pyrrolidine, piperidine, piperazine or morpholine. For example they may, together with the atom to which they are bound, form a 5-membered heterocycle, preferably a pyrrolidine.

In some embodiments, $R^{2A}$ and $R^{2B}$, together with the atom to which they are bound, form a 5-8 membered heterocycle, preferably pyrrolidine, piperidine, piperazine or morpholine. For example they may, together with the atom to which they are bound, form a 5-membered heterocycle, preferably a pyrrolidine.

Procedure a and Procedure B

The compounds described herein may be synthesized using Procedure A or Procedure B, as described herein. These Procedures may be used in automated oligonucleotide synthesis as described herein and illustrated in the appended examples.

Procedure A comprises:

(i) immersing a solid support to which a protected oligonucleotide or a protected modified oligonucleotide containing said phosphorous acid derivative is attached, in a mixture containing said oxidant, an imino derivative, and, optionally, a silylating reagent, a base and a solvent;

(ii) keeping the solid support immersed whilst maintaining the temperature within the required range for a period of time sufficient to ensure the conversion of said phosphorous acid derivative into a modified phosphate group, thereby producing a modified oligonucleotide of Formula (I) with a modified phosphate group;

(iii) continuing solid-phase oligonucleotide synthesis according to desired protocol until the next desired position of modification, then repeating steps (i) and (ii), or until the end of the oligonucleotide sequence;

(iv) performing desired deprotection and/or cleavage from solid support, thereby producing a deprotected modified oligonucleotide of Formula (I) with one or more modified phosphate groups.

Procedure B Comprises:

(i) immersing a solid support to which a protected oligonucleotide or protected modified oligonucleotide containing said phosphorous acid derivative is attached, in a mixture containing said organic azide, a solvent, and, optionally, a silylating reagent and a base;

(ii) repeating steps (ii) to (iv) of Procedure A;

The modified oligonucleotide is recovered at the end of the method.

The methods may be performed at a temperature of −20-150° C., preferably at 0-100° C., and more preferably at 15-80° C.

Preferably, Procedure A is performed at ambient temperature.

The concentration of an imino derivative in Procedure A is suitably 0.005-3 M, more preferably 0.1-1.5 M.

The concentration of azide in Procedure B is suitably 0.005-3 M, and preferably 0.1-1.5 M.

Optionally, a silylating reagent may be added. Suitable silylating agents include N,O-bis(trimethylsilyl)acetamide (BSA), N,O-bis(trimethylsilyl)trifluoroacetamide (BSTFA), chlorotrimethylsilane, bromotrimethylsilane, iodotrimethylsilane, triethylsilyl chloride, triphenylsilyl chloride, hexamethyldisilazane, trimethylsilyl trifluoromethanesulfonate (TMSOTf), dimethylisopropylsilyl chloride, diethylisopropylsilyl chloride, tert-butyldimethylsilyl chloride, tert-butyldiphenylsilyl chloride, triisopropylsilyl chloride, dimethyldichlorosilane, diphenyldichlorosilane and the like. In some preferred embodiments, N,O-bis(trimethylsilyl)acetamide (BSA) is used as a silylating agent.

Optionally, a base may be added. Suitable bases are amine bases, for example, triethylamine, N,N-diisopropylethylamine (DIEA), N-methylmorpholine, N-ethylmorpholine, tributylamine, 1,4-diazabicyclo[2.2.2]octane (DABCO), N-methylimidazole (NMI), pyridine, 2,6-lutidine, 2,4,6-collidine, 4-dimethylaminopyridine (DMAP), 1,8-bis(dimethylamino)naphthalene ("proton sponge"), 1,8-diazabicyclo[5.4.0]undec-7-ene (DBU), 1,5-diazabicyclo[4.3.0]non-5-ene (DBN), 1,5,7-triazabicyclo[4.4.0]dec-5-ene (TBD), 7-methyl-1,5,7-triazabicyclo[4.4.0]dec-5-ene (MTBD), 1,1,3,3-tetramethylguanidine (TMG), 2-tert-butyl-1,1,3,3-tetramethylguanidine, 2,8,9-trimethyl-2,5,8,9-tetraaza-1-phosphabicyclo[3.3.3]undecane, phosphazene base and the like.

A preferred base is triethylamine.

Suitable solvents for Procedure A include pyridine, 2-picoline, 3-picoline, 4-picoline, quinoline, tetrahydrofuran (THF), 1,4-dioxane, 1,2-dimethoxyethane (DME), diethylene glycol dimethyl ether (diglym), diethyl ether, acetonitrile and the like.

A preferred solvent for Procedure A is pyridine.

Suitable solvents for Procedure B include acetonitrile, N,N-dimethylformamide (DMF), N,N-dimethylacetamide (DMA), N-methylpyrrolidone (NMP), tetramethyl urea, 1,3-dimethylimidazolidin-2-one, sulfolane, hexamethyl phosphortriamide (HMPT), 1,4-dioxane, tetrahydrofuran (THF), acetone, ethyl acetate and the like.

Preferred solvents for Procedure B include N,N-dimethylformamide; N-methylpyrrolidone and acetonitrile.

Oligonucleotide Applications

Oligonucleotides according to the present invention may be used in a wide range of applications. For example, they may be used in vitro, e.g. as research or diagnostic agents, or in vivo, e.g. as therapeutic, diagnostic or research agents.

Accordingly, in one aspect of the present invention a method is provided, the method comprising contacting, in vitro or in vivo, an oligonucleotide according to the present invention (preferably single stranded) with an oligonucleotide having a high degree of sequence identity (preferably single stranded) and allowing the oligonucleotides to hybridise, (e.g. to form a double stranded oligonucleotide). The method may optionally further comprise the step of detecting and/or quantifying the hybridised oligonucleotides. The method may be a method of detecting a specific oligonucleotide, e.g. mutant, variant, or Single Nucleotide Polymorphism (SNP) containing oligonucleotide. The method may be a method of diagnosing the presence of a disease in a patient, e.g. involving detection of an oligonucleotide in a sample of tissue or bodily fluid collected from a patient.

Oligonucleotides according to the present invention may be designed and synthesised to serve as primers in a method of amplification of nucleic acids, such as in Polymerase Chain Reaction (PCR) methods.

Oligonucleotides according to the present invention may be designed and manufactured as oligonucleotide microarrays ("DNA chips") to be used in methods, where the use of oligonucleotide microarrays is necessary.

Oligonucleotides according to the present invention may also be used to design and synthesise therapeutic nucleic acids, such as siRNA (Angell & Baulcombe (1997) The EMBO Journal 16, 12:3675-3684; and Voinnet & Baulcombe (1997) Nature 389: pg 553); Fire A. et al., Nature, Vol 391, (1998); Fire (1999) *Trends Genet.* 15: 358-363, Sharp (2001) *Genes Dev.* 15: 485-490, Hammond et al. (2001) *Nature Rev. Genes* 2: 1110-1119 and Tuschl (2001) *Chem. Biochem.* 2: 239-245), ribozymes, aptamers (Systematic evolution of ligands by exponential enrichment: RNA ligands to bacteriophage T4 DNA polymerase. Science. 1990 Aug. 3; 249(4968):505-10); WO91/19813), DNAzymes, antisense, PMO, PNA, LNA, or gapmers. Oligonucleotide based therapies are well known in the art to treat a variety of diseases, e.g. including in the treatment of viral infection or viral mediated disease, cancer, disorders of the eye, such as age-related macular degeneration, prevention of unwanted neovascularisation, exon-splicing deficiency disorders, such as Duchenne muscular dystrophy, and as anti-cholesterol agents. The design of oligonucleotide agents known or proposed for such treatments may be modified to incorporate the modified phosphate(s) described herein. Optionally, therapeutic nucleic acids may be conjugated to a delivery agent such as a cell penetrating peptide (e.g. as described in WO2009/147368).

Accordingly, in one aspect an oligonucleotide according to the present invention is provided for use in a method of medical treatment, or for use in therapy. In another aspect the use of an oligonucleotide according to the present invention in the manufacture of a medicament or pharmaceutical composition for use in the treatment of a disease is provided. In another aspect a method of treatment of a disease is provided, the method comprising administering an oligonucleotide according to the present invention to a patient in need thereof, thereby treating said disease.

Oligonucleotides according to the present invention may be formulated as a medicament or pharmaceutical composition. A medicament or pharmaceutical composition may comprise an oligonucleotide of the present invention, e.g. in purified or isolated form, and a pharmaceutically acceptable carrier, diluent, excipient or adjuvant.

Medicaments and pharmaceutical compositions according to aspects of the present invention may be formulated for administration by a number of routes, including but not limited to, parenteral, intravenous, intra-arterial, intramuscular, oral and nasal. The medicaments and compositions may be formulated in fluid or solid form. Fluid formulations may be formulated for administration by injection to a selected region of the human or animal body.

Administration is preferably in a "therapeutically effective amount", this being sufficient to show benefit to the individual. The actual amount administered, and rate and time-course of administration, will depend on the nature and severity of the disease being treated. Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

Methods according to the present invention may be performed in vitro or in vivo. The term "in vitro" is intended to encompass experiments with materials, biological substances, cells and/or tissues in laboratory conditions or in culture whereas the term "in vivo" is intended to encompass experiments and procedures with intact multi-cellular organisms.

A subject to be treated may be any animal or human. The subject is preferably mammalian, more preferably human. The subject may be a non-human mammal, but is more preferably human. The subject may be male or female. The subject may be a patient.

---oOo---

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

While the present invention has been described with reference to the specific embodiments thereof, it should be understood by those skilled in the art that various changes may be made and equivalents substituted without departing from the true spirit and scope of the invention.

In addition, many modifications may be made to adapt a particular situation, material, composition of matter, process, process step or steps, to the objective spirit and scope of the present invention. All such modifications are intended to be within the scope of the claims appended hereto.

The invention will now be illustrated by the following non-limiting examples, with reference to the corresponding Figures.

EXAMPLES

The following examples are provided by way of illustration and are not intended to limit the invention.

General Methods

Modified oligonucleotides were synthesized on a Biosset automated DNA synthesizer ASM-800 using either β-cyanoethyl phosphoramidite chemistry [58] or H-phosphonate chemistry [66] on 0.2 µmol scale using standard 12 µl columns.

All reactions were carried out in 1.5 ml polypropylene tubes with screw caps and rubber O-rings. After solid-phase synthesis, polymer support from the column was transferred to a plastic tube and treated with 200 µl deblocking solution per 5 mg of support. Either conc (ca. 33%) aq ammonia solution (Soln A) or 1:1 vol. mixture of ethylenediamine and abs. ethanol (Soln B) was used as a deblocking solution. After deblocking the supernatant was evaporated in vacuo using a SpeedVac concentrator and 400 µl of 20 mM triethylammonium acetate, pH 7 was added, and support removed by centrifugation.

Modified oligonucleotides were purified by reverse-phased (RP) HPLC either in DMTr OFF or in DMTR ON mode on an Agilent 1200 series chromatograph using a gradient of acetonitrile from 0 to 40% in 0.02 M triethylammonium acetate, pH 7 for 30 min, flow rate 2 cm$^3$ min$^{-1}$ on a Zorbax SB-C18 (5 µm) column (4.6×150 mm). 5'-Terminal DMTr group was removed by 15 min treatment with 100 µl 80% acetic acid followed by neutralisation with 400 µl 20 mM triethylammonium acetate, pH 7.0 and evaporation on a SpeedVac concentrator. Then oligonucleotides were precipitated by adding 1 ml 1 M LiClO$_4$ in acetone, the pellet washed by acetone and dried on air for 20 min. Denaturing gel-electrophoresis in 20% polyacrylamide gel (PAGE) was used to check purity of oligonucleotides with bands visualized by staining with Stains-All. Structures of modified oligonucleotides were confirmed by matrix-assisted laser desorption ionization—time of flight (MALDI-TOF) mass spectra recorded in either negative or positive ion mode on a Bruker Reflex III Autoflex Speed mass spectrometer using 3-hydroxypicolinic acid as a matrix.

Preparation of 0.5 M Solution of Bis(Dimethylamino) Azidocarbenium Dichlorophosphate.

To a solution of bis(dimethylamino)chlorocarbenium dichlorophosphate (1.105 g, 4.1 mmol) [67] in dry MeCN (10 ml) powdered and dried NaN$_3$ (1.1 equiv, 288 mg, 4.4 mmol) was added. The suspension was stirred for 2 h at ambient temperature, filtered, washed with dry MeCN, evaporated and dried in vacuo, yielding 1.08 g (95%) of oily product. Sixty nine milligrams of the product were dissolved in 1 ml of DMF-Et$_3$N 95:5 (v/v), vigorously shaken for 2 min and the precipitate separated by centrifugation for 3 min at 14,500 rpm to give 0.5 M solution, which can be stored at ambient temperature for up to a week.

Preparation of 1 M solution of 2-azido-1,3-dimethylimidazolinium hexafluorophosphate.

2-Chloro-1,3-dimethylimidazolinium hexafluorophosphate (139 mg) and NaN$_3$ (1.1 equiv, 36 mg) were weighed into a 1.5 ml plastic tube, dry acetonitrile (0.5 ml) was added, and the suspension was shaken for 2 h at 30° C., then the precipitate was separated by centrifugation for 5 min at 14,500 rpm. The solution was stored at −18° C.

Preparation of 1 M solution of azidodipyrrolidinocarbenium hexafluorophosphate.

Chlorodipyrrolidinocarbenium hexafluorophosphate (166 mg) and NaN$_3$ (1.1 equiv, 36 mg) were weighed into a 1.5 ml plastic tube, dry acetonitrile (0.5 ml) was added, and the suspension was shaken for 2 h at 30° C., then the precipitate was separated by centrifugation for 5 min at 14,500 rpm. The solution was stored at −18° C.

Example 1. Preparation of a Modified Oligonucleotide 5'-d(TTTTTpT) with the N,N,N',N'-Tetramethyl Phosphoryl Guanidine Group (FVIII); p Here and in the Following Examples Indicates Position of the Modified Phosphate Group

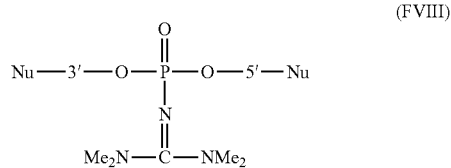

(FVIII)

1.1. Procedure (a) with β-Cyanoethyl Phosphite and Iodine.

A column containing 5 mg of High Load 5'-DMTr-dT CPG support (110 μmol g$^{-1}$) was placed into a DNA synthesizer, and automated β-cyanoethyl phosphoramidite solid-phase DNA synthesis was started on 0.2 μmol scale. Synthesis was interrupted after 5'-detritylation, phosphoramidite coupling and capping but before oxidation. The column was detached from synthesiser, drained on a water pump, rinsed with MeCN, and the support with attached phosphite was transferred into a plastic tube.

Soln 1 was prepared by dissolving iodine crystals in dry pyridine to 0.2 M concentration (51 mg per ml). Soln 2 was prepared by mixing 124 μl N,N,N',N'-tetramethylguanidine (TMG), 50 μl N,O-bis(trimethylsilyl)acetamide (BSA) and 325 μl dry pyridine, and adding 3 Å molecular sieves to ca. ¼ vol. Aliquots of 20 μl of Soln 1 and 2 were mixed in a plastic tube, 10 μl of BSA were added, and after 1 min wait the content was transferred to the tube with polymer. The tube was vortexed for 30 s, centrifugated at 14,500 rpm for 15 s and shaken for 5 min at ambient temperature. Supernatant was discarded, the support was rinsed with 2×200 μl MeCN, transferred into a synthesiser column, and β-cyanoethyl phosphoramidite solid-phase synthesis was resumed until the end of the sequence.

The oligonucleotide was detached from support and protecting groups removed by Soln A for 1 h at ambient temperature.

Molecular mass: calc. [M] 1860.39, exp. [M+H] 1860.93, [M−H] 1859.14.

1.2. Procedure (a) with H-phosphonate and Iodine.

A column containing 5 mg of 5'-DMTr-dT CPG support (40 μmol g$^{-1}$) was placed into a DNA synthesizer, and automated solid-phase DNA synthesis by H-phosphonate method was started on 0.2 μmol scale. Synthesis was interrupted after 5'-detritylation and H-phosphonate coupling, and the column was detached from synthesiser, drained on a water pump, rinsed with MeCN, and the support with attached dinucleoside H-phosphonate was transferred into a plastic tube.

Soln 1 was prepared by dissolving iodine crystals in dry pyridine to 0.2 M concentration (51 mg per ml). Soln 2 was prepared by mixing 100 μl TMG and 400 μl dry pyridine (20% vol), and adding 3 Å molecular sieves to ca. ¼ vol. Aliquots of 20 μl of Soln 1 and 2 were added to the tube with support, vortexed for 30 s, centrifugated at 14,500 rpm for 15 s and shaken for 30 min at ambient temperature. Supernatant was discarded, the support was rinsed with 2×200 μl MeCN, transferred into a synthesiser column, and β-cyanoethyl phosphoramidite solid-phase synthesis was resumed until the end of the sequence.

The oligonucleotide was detached from support and protecting groups removed by Soln A for 1 h at ambient temperature.

Molecular mass: calc. [M] 1860.39, exp. [M+H] 1861.17, [M−H] 1857.96.

1.3. Procedure (a) with H-phosphonate, BSA and Iodine.

A column containing 5 mg of 5'-DMTr-dT CPG support (40 μmol g$^{-1}$) was placed into a DNA synthesizer, and automated solid-phase DNA synthesis by H-phosphonate method was started on 0.2 μmol scale. Synthesis was interrupted after 5'-detritylation and H-phosphonate coupling, and the column was detached from synthesiser, drained on a water pump, rinsed with MeCN, and the support with attached dinucleoside H-phosphonate was transferred into a plastic tube.

Soln 1 was prepared by dissolving iodine crystals in dry pyridine to 0.2 M concentration (51 mg per ml). Soln 2 was prepared by mixing 125 μl TMG (2 M), 50 μl BSA (1 M) and 325 μl dry pyridine (20% vol), and adding 3 Å molecular sieves to ca. ¼ vol. Aliquots of 20 μl of Soln 1 and 2 were added to the tube with support, 10 μl BSA were added, and the tube was vortexed for 30 s, centrifugated at 14,500 rpm for 15 s and shaken for 5 min at ambient temperature. Supernatant was discarded, the support was rinsed with 2×200 μl MeCN, transferred into a synthesiser column, and β-cyanoethyl phosphoramidite solid-phase synthesis was resumed until the end of the sequence.

The oligonucleotide was detached from support and protecting groups removed by Soln A for 1 h at ambient temperature.

Molecular mass: calc. [M] 1860.39, exp. [M+H] 1861.17, [M−H] 1857.96.

1.4. Procedure (a) with H-phosphonate and CCl$_4$.

A column containing 5 mg of 5'-DMTr-dT CPG support (40 μmol g$^{-1}$) was placed into a DNA synthesizer, and automated solid-phase DNA synthesis by H-phosphonate method was started on 0.2 μmol scale. Synthesis was interrupted after 5'-detritylation and H-phosphonate coupling, and the column was detached from synthesiser, drained on a water pump, rinsed with MeCN, and the support with attached dinucleoside H-phosphonate was transferred into a plastic tube.

Soln 1 was prepared by keeping CCl$_4$ over 3 Å molecular sieves for 16 h. Soln 2 was prepared by mixing 100 μl TMG and 400 μl dry pyridine (20% vol), and adding 3 Å molecular sieves to ca. ¼ vol. Aliquots of 20 μl of Soln 1 and 2 were added to the tube with support, vortexed for 30 s, centrifugated at 14,500 rpm for 15 s and shaken for 30 min at ambient temperature. Supernatant was discarded, the support was rinsed with 2×200 µl MeCN, transferred into a synthesiser column, and β-cyanoethyl phosphoramidite solid-phase synthesis was resumed until the end of the sequence.

The oligonucleotide was detached from support and protecting groups removed by Soln A for 1 h at ambient temperature.

Molecular mass: calc. [M] 1860.39, exp. [M+H] 1860.78, [M−H] 1858.67.

1.5. Procedure (a) with H-Phosphonate and CCl$_3$Br.

A column containing 5 mg of 5'-DMTr-dT CPG support (40 µmol g$^{-1}$) was placed into a DNA synthesizer, and automated solid-phase DNA synthesis by H-phosphonate method was started on 0.2 µmol scale. Synthesis was interrupted after 5'-detritylation and H-phosphonate coupling, and the column was detached from synthesiser, drained on a water pump, rinsed with MeCN, and the support with attached dinucleoside H-phosphonate was transferred into a plastic tube.

Soln 1 was prepared by keeping CCl$_3$Br over 3 Å molecular sieves for 16 h. Soln 2 was prepared by mixing 100 µl TMG and 400 µl dry pyridine (20% vol), and adding 3 Å molecular sieves to ca. ¼ vol. Aliquots of 20 µl of Soln 1 and 2 were added to the tube with support, vortexed for 30 s, centrifugated at 14,500 rpm for 15 s and shaken for 1 h at ambient temperature. Supernatant was discarded, the support was rinsed with 2×200 µl MeCN, transferred into a synthesiser column, and β-cyanoethyl phosphoramidite solid-phase synthesis was resumed until the end of the sequence.

The oligonucleotide was detached from support and protecting groups removed by Soln A for 1 h at ambient temperature.

Molecular mass: calc. [M] 1860.39, exp. [M+H] 1861.13, [M−H] 1859.25.

1.6. Procedure (b) with β-Cyanoethyl Phosphite and Bis(Dimethylamino)-1-Azidocarbenium Dichlorophosphate.

A column containing 5 mg of High Load 5'-DMTr-dT CPG support (110 µmol g$^{-1}$) was placed into a DNA synthesizer, and automated β-cyanoethyl phosphoramidite solid-phase DNA synthesis was started on 0.2 µmol scale. Synthesis was interrupted after 5'-detritylation, phosphoramidite coupling and capping but before oxidation. The column was detached from synthesiser, drained on a water pump, rinsed with MeCN, and the support with attached phosphite was transferred into a plastic tube.

An aliquot of 40 µl 0.5 M bis(dimethylamino)-1-azidocarbenium dichlorophosphate was transferred into a plastic tube, 10 µul BSA was added and the tube was vortexed for 1 min, centrifugated at 14,500 rpm for 1 min and left for 30 min at ambient temperature. The content was transferred into the tube with support, vortexed for 30 s, centrifugated at 14,500 rpm for 30 s and shaken for 30 min at ambient temperature. Supernatant was discarded, the support was rinsed with 2×200 µl MeCN, transferred into a synthesiser column, and β-cyanoethyl phosphoramidite solid-phase synthesis was resumed until the end of the sequence.

The oligonucleotide was detached from support and protecting groups removed by Soln A for 1 h at ambient temperature.

Molecular mass: calc. [M] 1860.39, exp. [M+H] 1860.35, [M−H] 1857.54.

Example 2. Preparation of a Modified Oligonucleotide 5'-d(TpTTTT) with the N,N,N',N'-Tetramethyl Phosphoryl Guanidine Group (FVIII)

A column containing 5 mg of High Load 5'-DMTr-dT CPG support (110 µmol g$^{-1}$) was placed into a DNA synthesizer, and automated β-cyanoethyl phosphoramidite solid-phase DNA synthesis was started on 0.2 µmol scale. Synthesis was interrupted after four dT incorporations followed by 5'-detritylation, phosphoramidite coupling and capping but before oxidation. The column was detached from synthesiser, drained on a water pump, rinsed with MeCN, and the support with attached phosphite was transferred into a plastic tube.

An aliquot of 40 µl 0.5 M bis(dimethylamino)-1-azidocarbenium dichlorophosphate was transferred into a plastic tube, 10 µl BSA was added and the tube was vortexed for 1 min, centrifugated at 14,500 rpm for 1 min and left for 30 min at ambient temperature. The content was transferred into the tube with support, vortexed for 30 s, centrifugated at 14,500 rpm for 30 s and shaken for 30 min at ambient temperature. Supernatant was discarded, the support was rinsed with 2×200 µl MeCN, transferred into a synthesiser column, and the synthesis was completed by 5'-detritylation.

The oligonucleotide was detached from support and protecting groups removed by Soln A for 1 h at ambient temperature.

Molecular mass: calc. [M] 1860.39, exp. [M+H] 1860.34, [M−H] 1858.63.

Example 3. Preparation of a Modified Oligonucleotide 5'-d(TTTTpTpT) with the N,N,N',N'-tetramethyl Phosphoryl Guanidine Group (FVIII)

3.1. Procedure (a) with H-Phosphonate, BSA and Iodine.

A column containing 5 mg of 5'-DMTr-dT CPG support (40 µmol g$^{-1}$) was placed into a DNA synthesizer, and automated solid-phase DNA synthesis by H-phosphonate method was started on 0.2 µmol scale. Synthesis was interrupted after two dT H-phosphonate incorporations, and the column was detached from synthesiser, drained on a water pump, rinsed with MeCN, and the support with attached trinucleoside bis-H-phosphonate was transferred into a plastic tube.

Soln 1 was prepared by dissolving iodine crystals in dry pyridine to 0.2 M concentration (51 mg per ml). Soln 2 was prepared by mixing 125 µl TMG (2 M), 50 µl BSA (1 M) and 325 µl dry pyridine (20% vol), and adding 3 Å molecular sieves to ca. ¼ vol. Aliquots of 20 µl of Soln 1 and 2 were added to the tube with support, 10 µl BSA were added, and the tube was vortexed for 30 s, centrifugated at 14,500 rpm for 15 s and shaken for 10 min at ambient temperature. Supernatant was discarded, the support was rinsed with 2×200 µl MeCN, transferred into a synthesiser column, and β-cyanoethyl phosphoramidite solid-phase synthesis was resumed until the end of the sequence.

The oligonucleotide was detached from support and protecting groups removed by Soln A for 1 h at ambient temperature.

Molecular mass: calc. [M] 1957.55, exp. [M+H] 1958.28, [M−H] 1956.34.

3.2. Procedure (b) with β-cyanoethyl Phosphite and bis(dimethylamino)-1-Azidocarbenium Dichlorophosphate.

A column containing 5 mg of High Load 5'-DMTr-dT CPG support (110 µmol g$^{-1}$) was placed into a DNA synthesizer, and automated β-cyanoethyl phosphoramidite solid-phase DNA synthesis was started on 0.2 umol scale. Synthesis was interrupted after 5'-detritylation, phosphoramidite coupling and capping but before oxidation. The column was detached from synthesiser, drained on a water pump, rinsed with MeCN, and the support with attached phosphite was transferred into a plastic tube.

An aliquot of 80 µl 0.5 M bis(dimethylamino)-1-azidocarbenium dichlorophosphate was transferred into a plastic tube, 20 µl BSA was added and the tube was vortexed for 1 min, centrifugated at 14,500 rpm for 1 min and left for 30 min at ambient temperature. An aliquot of 50 µl was transferred into the tube with support, vortexed for 30 s, centrifugated at 14,500 rpm for 30 s and shaken for 30 min at ambient temperature. Supernatant was discarded, the support was rinsed with 2×200 µl MeCN, transferred into a synthesiser column, another dT phosphoramidite was coupled and the synthesis was interrupted before oxidation. The column was detached from synthesiser, drained on a water pump, rinsed with MeCN, and the support with attached phosphite was transferred into a plastic tube.

An aliquot of 50 µl was transferred into the tube with support, vortexed for 30 s, centrifugated at 14,500 rpm for 30 s and shaken for 30 min at ambient temperature. Supernatant was discarded, the support was rinsed with 2×200 µl MeCN, transferred into a synthesiser column, and the synthesis was resumed until the end of the sequence.

The oligonucleotide was detached from support and protecting groups removed by Soln A for 1 h at ambient temperature.

Molecular mass: calc. [M] 1957.55, exp. [M+H] 1958.32, [M–H] 1955.44.

Example 4. Preparation of a Modified Oligonucleotide 5'-d(TTTpTpTpT) with the N,N,N',N'-tetramethyl Phosphoryl Guanidine Group (FVIII)

4.1. Procedure (a) with H-phosphonate, BSA and Iodine.

A column containing 5 mg of 5'-DMTr-dT CPG support (40 µmol g$^{-1}$) was placed into a DNA synthesizer, and automated solid-phase DNA synthesis by H-phosphonate method was started on 0.2 µmol scale. Synthesis was interrupted after three dT H-phosphonate incorporations, and the column was detached from synthesiser, drained on a water pump, rinsed with MeCN, and the support with attached tetranucleoside tris-H-phosphonate was transferred into a plastic tube.

Soln 1 was prepared by dissolving iodine crystals in dry pyridine to 0.2 M concentration (51 mg per ml). Soln 2 was prepared by mixing 125 µl TMG (2 M), 50 µl BSA (1 M) and 325 µl dry pyridine (20% vol), and adding 3 Å molecular sieves to ca. ¼ vol. Aliquots of 20 µl of Soln 1 and 2 were added to the tube with support, 10 µl BSA were added, and the tube was vortexed for 30 s, centrifugated at 14,500 rpm for 15 s and shaken for 10 min at ambient temperature. Supernatant was discarded, the support was rinsed with 2×200 µl MeCN, transferred into a synthesiser column, and β-cyanoethyl phosphoramidite solid-phase synthesis was resumed until the end of the sequence.

The oligonucleotide was detached from support and protecting groups removed by Soln A for 1 h at ambient temperature.

Molecular mass: calc. [M] 2054.72, exp. [M+H] 2055.49.

4.2. Procedure (b) with β-cyanoethyl Phosphite and bis(dimethylamino)-1-Azidocarbenium Dichlorophosphate.

A column containing 5 mg of High Load 5'-DMTr-dT CPG support (110 µmol g$^{-1}$) was placed into a DNA synthesizer, and automated β-cyanoethyl phosphoramidite solid-phase DNA synthesis was started on 0.2 µmol scale. Synthesis was interrupted after 5'-detritylation, phosphoramidite coupling and capping but before oxidation. The column was detached from synthesiser, drained on a water pump, rinsed with MeCN, and the support with attached phosphite was transferred into a plastic tube.

An aliquot of 120 µl 0.5 M bis(dimethylamino)-1-azidocarbenium dichlorophosphate was transferred into a plastic tube, 30 µl BSA was added and the tube was vortexed for 1 min, centrifugated at 14,500 rpm for 1 min and left for 30 min at ambient temperature. An aliquot of 50 µl was transferred into the tube with support, vortexed for 30 s, centrifugated at 14,500 rpm for 30 s and shaken for 30 min at ambient temperature. Supernatant was discarded, the support was rinsed with 2×200 µl MeCN, transferred into a synthesiser column, another dT phosphoramidite was coupled and the synthesis was interrupted before oxidation. The column was detached from synthesiser, drained on a water pump, rinsed with MeCN, and the support with attached phosphite was transferred into a plastic tube.

Second aliquot of 50 µl was transferred into the tube with support, vortexed for 30 s, centrifugated at 14,500 rpm for 30 s and shaken for 30 min at ambient temperature. Supernatant was discarded, the support was rinsed with 2×200 µl MeCN, transferred into a synthesiser column, another dT phosphoramidite was coupled and the synthesis was interrupted before oxidation. The column was detached from synthesiser, drained on a water pump, rinsed with MeCN, and the support with attached phosphite was transferred into a plastic tube.

Third aliquot of 50 µl was transferred into the tube with support, vortexed for 30 s, centrifugated at 14,500 rpm for 30 s and shaken for 30 min at ambient temperature. Supernatant was discarded, the support was rinsed with 2×200 µl MeCN, transferred into a synthesiser column, and the synthesis was resumed until the end of the sequence.

The oligonucleotide was detached from support and protecting groups removed by Soln A for 1 h at ambient temperature.

Molecular mass: calc. [M] 2054.72, exp. [M+H] 2054.49.

Example 5. Preparation of a Modified Oligonucleotide 5'-d(TTTTTpT) with the Phosphoryl Guanidine Group (FIX)

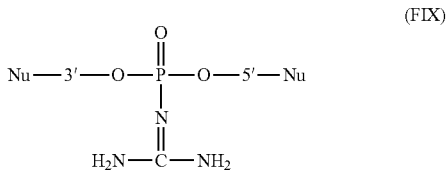

A column containing 5 mg of High Load 5'-DMTr-dT CPG support (110 µmol g$^{-1}$) was placed into a DNA synthesizer, and automated β-cyanoethyl phosphoramidite solid-phase DNA synthesis was started on 0.2 umol scale. Synthesis was interrupted after 5'-detritylation, phosphoramidite coupling and capping but before oxidation. The column was detached from synthesiser, drained on a water pump, rinsed with MeCN, and the support with attached phosphite was transferred into a plastic tube.

Soln 1 was prepared by dissolving iodine crystals in dry pyridine to 0.2 M concentration (51 mg per ml). Soln 2 was prepared by weighing 9.6 mg of dried guanidine hydrochloride into a plastic tube, adding 85 µl dry pyridine, 15 µl 1,8-diazabicyclo[5.4.0]undec-7-ene (DBU), 10 µl BSA, and the tube was vortexed for 5 min and sonicated until clear (ca. 5 min). Aliquots of 20 µl of Soln 1 and 2 were mixed in a plastic tube, 10 µl of BSA were added, and after 1 min wait the content was transferred to the tube with polymer. The tube was vortexed for 30 s, centrifugated at 14,500 rpm for 15 s and shaken for 5 min at ambient temperature. Supernatant was discarded, the support was rinsed with 2×200 µl MeCN, transferred into a synthesiser column, and β-cyanoethyl phosphoramidite solid-phase synthesis was resumed until the end of the sequence.

The oligonucleotide was detached from support and protecting groups removed by Soln A for 1 h at ambient temperature.

Molecular mass: calc. [M] 1804.28, exp. [M+H] 1804.62, [M−H] 1803.25.

Example 6. Preparation of a Modified Oligonucleotide 5'-d(TpTTTTT) with the Phosphoryl Guanidine Group (FIX)

A column containing 5 mg of High Load 5'-DMTr-dT CPG support (110 µmol g$^{-1}$) was placed into a DNA synthesizer, and automated β-cyanoethyl phosphoramidite solid-phase DNA synthesis was started on 0.2 umol scale. Synthesis was interrupted after four dT incorporations followed by 5'-detritylation, phosphoramidite coupling and capping but before oxidation. The column was detached from synthesiser, drained on a water pump, rinsed with MeCN, and the support with attached phosphite was transferred into a plastic tube.

Soln 1 was prepared by dissolving iodine crystals in dry pyridine to 0.2 M concentration (51 mg per ml). Soln 2 was prepared by weighing 9.6 mg of dried guanidine hydrochloride into a plastic tube, adding 85 µl dry pyridine, 15 µl DBU, 10 µl BSA, and the tube was vortexed for 5 min and sonicated until clear (ca. 5 min). Aliquots of 20 µl of Soln 1 and 2 were mixed in a plastic tube, 10 µl of BSA were added, and after 1 min wait the content was transferred to the tube with polymer. The tube was vortexed for 30 s, centrifugated at 14,500 rpm for 15 s and shaken for 5 min at ambient temperature. Supernatant was discarded, the support was rinsed with 2×200 µl MeCN, transferred into a synthesiser column, and the synthesis was completed by 5'-detritylation.

The oligonucleotide was detached from support and protecting groups removed by Soln A for 1 h at ambient temperature.

Molecular mass: calc. [M] 1804.28, exp. [M+H] 1804.76, [M−H] 1803.06.

Example 7. Preparation of a Modified Oligonucleotide 5'-d(TTTTTpT) with the O-methyl Phosphoryl Isourea Group (FX)

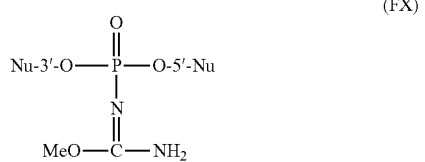

(FX)

A column containing 5 mg of High Load 5'-DMTr-dT CPG support (110 µmol g$^{-1}$) was placed into a DNA synthesizer, and automated β-cyanoethyl phosphoramidite solid-phase DNA synthesis was started on 0.2 µmol scale. Synthesis was interrupted after 5'-detritylation, phosphoramidite coupling and capping but before oxidation. The column was detached from synthesiser, drained on a water pump, rinsed with MeCN, and the support with attached phosphite was transferred into a plastic tube.

Soln 1 was prepared by dissolving iodine crystals in dry pyridine to 0.2 M concentration (51 mg per ml). Soln 2 was prepared by weighing 8.6 mg of dried O-methylisourea hydrogen sulfate into a plastic tube, adding 35 µl dry pyridine, 15 µl 1,8-diazabicyclo[5.4.0]undec-7-ene (DBU), 5 µl BSA, and the tube was vortexed for 5 min and sonicated until clear (ca. 10 min) followed by centrifugation at 14,500 rpm for 2 min. Aliquots of 20 µl of Soln 1 and 2 were mixed in a plastic tube, 10 µl of BSA were added, and after 1 min wait the content was transferred to the tube with polymer. The tube was vortexed for 30 s, centrifugated at 14,500 rpm for 15 s and shaken for 5 min at ambient temperature. Supernatant was discarded, the support was rinsed with 2×200 µl MeCN, transferred into a synthesiser column, and the synthesis was resumed until the end of the sequence.

The oligonucleotide was detached from support and protecting groups removed by Soln
A for 16 h at 55° C.

Molecular mass: calc. [M] 1819.29, exp. [M+H] 1819.59, [M−H] 1818.26.

Example 8. Preparation of a Modified Oligonucleotide 5'-d(TTTTTpT) with the N-β-aminoethyl Phosphoryl Guanidine Group (FXI)

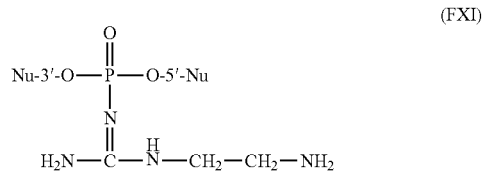

(FXI)

A column containing 5 mg of High Load 5'-DMTr-dT CPG support (110 µmol g$^{-1}$) was placed into a DNA synthesizer, and automated β-cyanoethyl phosphoramidite solid-phase DNA synthesis was started on 0.2 umol scale. Synthesis was interrupted after 5'-detritylation, phosphoramidite coupling and capping but before oxidation. The column was detached from synthesiser, drained on a water pump, rinsed with MeCN, and the support with attached phosphite was transferred into a plastic tube.

Soln 1 was prepared by dissolving iodine crystals in dry pyridine to 0.2 M concentration (51 mg per ml). Soln 2 was prepared by weighing 8.6 mg of dried O-methylisourea hydrogen sulfate into a plastic tube, adding 35 µl dry pyridine, 15 µl 1,8-diazabicyclo[5.4.0]undec-7-ene (DBU), 5 µl BSA, and the tube was vortexed for 5 min and sonicated until clear (ca. 10 min) followed by centrifugation at 14,500 rpm for 2 min. Aliquots of 20 µl of Soln 1 and 2 were mixed in a plastic tube, 10 µl of BSA were added, and after 1 min wait the content was transferred to the tube with polymer. The tube was vortexed for 30 s, centrifugated at 14,500 rpm for 15 s and shaken for 5 min at ambient temperature. Supernatant was discarded, the support was rinsed with 2×200 µl MeCN, transferred into a synthesiser column, and the synthesis was resumed until the end of the sequence.

The oligonucleotide was detached from support and protecting groups removed by Soln B for 16 h at 55° C.

Molecular mass: calc. [M] 1847.35, exp. [M+H] 1847.16, [M−H] 1844.76.

Example 9. Preparation of a Modified Oligonucleotide 5'-d(TCpA) with the N,N,N',N'-tetramethyl Phosphoryl Guanidine Group (FVIII)

A column containing 5 mg of 5'-DMTr-dA(Bz) CPG support (110 µmol g$^{-1}$) was placed into a DNA synthesiser, and automated β-cyanoethyl phosphoramidite solid-phase DNA synthesis was started on 0.2 µmol scale. Synthesis was interrupted after 5'-detritylation, dC phosphoramidite coupling and capping but before oxidation. The column was detached from synthesiser, drained on a water pump, rinsed with MeCN, and the support with attached phosphite was transferred into a plastic tube.

An aliquot of 40 µl 0.5 M bis(dimethylamino)-1-azidocarbenium dichlorophosphate was transferred into a plastic tube, 10 µl BSA was added and the tube was vortexed for 1 min, centrifugated at 14,500 rpm for 1 min and left for 30 min at ambient temperature. The content was transferred into the tube with support, vortexed for 30 s, centrifugated at 14,500 rpm for 30 s and shaken for 30 min at ambient temperature. Supernatant was discarded, the support was rinsed with 2×200 µl MeCN, transferred into a synthesiser column, and the synthesis was resumed until the end of the sequence.

The oligonucleotide was detached from support and protecting groups removed by Soln A for 16 h at ambient temperature.

Molecular mass: calc. [M] 941.80, exp. [M+H] 942.17, [M−H] 938.97.

$^{31}$P NMR (D$_2$O, δ, ppm): "fast" diastereomer 0.37, "slow" diastereomer 0.21.

Example 10. Preparation of a Modified Oligonucleotide 5'-d(GCGCCAAACpA) (SEQ ID NO: 11) with the N,N,N',N'-tetramethyl Phosphoryl Guanidine Group (FVIII)

A column containing 5 mg of 5'-DMTr-dA(Bz) CPG support (110 µmol g$^{-1}$) was placed into a DNA synthesiser, and automated β-cyanoethyl phosphoramidite solid-phase DNA synthesis was started on 0.2 µmol scale. Synthesis was interrupted after 5'-detritylation, dC phosphoramidite coupling and capping but before oxidation. The column was detached from synthesiser, drained on a water pump, rinsed with MeCN, and the support with attached phosphite was transferred into a plastic tube.

An aliquot of 40 µl 0.5 M bis(dimethylamino)-1-azidocarbenium dichlorophosphate was transferred into a plastic tube, 10 µl BSA was added and the tube was vortexed for 1 min, centrifugated at 14,500 rpm for 1 min and left for 30 min at ambient temperature. The content was transferred into the tube with support, vortexed for 30 s, centrifugated at 14,500 rpm for 30 s and shaken for 30 min at ambient temperature. Supernatant was discarded, the support was rinsed with 2×200 µl MeCN, transferred into a synthesiser column, and the synthesis was resumed until the end of the sequence.

The oligonucleotide was detached from support and protecting groups removed by Soln A for 12 h at 55° C. An HPLC trace of the oligonucleotide is given in FIG. 1.

Molecular mass: calc. [M] 3103.21, exp. [M+H] 3102.12, [M−H] 3100.61.

Example 11. Preparation of a Modified Oligonucleotide 5'-d(GCGCCAAApCpA) (SEQ ID NO: 7) with the N,N,N',N'-tetramethyl Phosphoryl Guanidine Group (FVIII)

A column containing 5 mg of 5'-DMTr-dA(Bz) CPG support (110 µmol g$^{-1}$) was placed into a DNA synthesiser, and automated β-cyanoethyl phosphoramidite solid-phase DNA synthesis was started on 0.2 µmol scale. Synthesis was interrupted after 5'-detritylation, dC phosphoramidite coupling and capping but before oxidation. The column was detached from synthesiser, drained on a water pump, rinsed with MeCN, and the support with attached phosphite was transferred into a plastic tube.

An aliquot of 80 µl 0.5 M bis(dimethylamino)-1-azidocarbenium dichlorophosphate was transferred into a plastic tube, 20 µl BSA was added and the tube was vortexed for 1 min, centrifugated at 14,500 rpm for 1 min and left for 30 min at ambient temperature. An aliquot of 50 µl was transferred into the tube with support, vortexed for 30 s, centrifugated at 14,500 rpm for 30 s and shaken for 30 min at ambient temperature. Supernatant was discarded, the support was rinsed with 2×200 µl MeCN, transferred into a synthesiser column, a dA phosphoramidite was coupled and the synthesis was interrupted before oxidation. The column was detached from synthesiser, drained on a water pump, rinsed with MeCN, and the support with attached phosphite was transferred into a plastic tube.

Second aliquot of 50 µl was transferred into the tube with support, vortexed for 30 s, centrifugated at 14,500 rpm for 30 s and shaken for 30 min at ambient temperature. Supernatant was discarded, the support was rinsed with 2×200 µl MeCN, transferred into a synthesiser column, and the synthesis was resumed until the end of the sequence.

The oligonucleotide was detached from support and protecting groups removed by Soln A for 12 h at 55° C. An HPLC trace of the oligonucleotide is given in FIG. 1.

Molecular mass: calc. [M] 3200.38, exp. [M+H] 3199.90, [M−H] 3199.00.

Example 12. Preparation of a Modified Oligonucleotide 5'-d(GCGCCAApACpA) (SEQ ID NO: 14) with the N,N,N',N'-tetramethyl Phosphoryl Guanidine Group (FVIII)

A column containing 5 mg of 5'-DMTr-dA(Bz) CPG support (110 µmol g$^{-1}$) was placed into a DNA synthesiser, and automated β-cyanoethyl phosphoramidite solid-phase DNA synthesis was started on 0.2 µmol scale. Synthesis was interrupted after 5'-detritylation, dC phosphoramidite coupling and capping but before oxidation. The column was detached from synthesiser, drained on a water pump, rinsed with MeCN, and the support with attached phosphite was transferred into a plastic tube.

An aliquot of 80 µl 0.5 M bis(dimethylamino)-1-azidocarbenium dichlorophosphate was transferred into a plastic tube, 20 µl BSA was added and the tube was vortexed for 1 min, centrifugated at 14,500 rpm for 1 min and left for 30 min at ambient temperature. An aliquot of 50 µl was transferred into the tube with support, vortexed for 30 s, centrifugated at 14,500 rpm for 30 s and shaken for 30 min at ambient temperature. Supernatant was discarded, the support was rinsed with 2×200 µl MeCN, transferred into a synthesiser column, then a dA phosphoramidite was coupled followed by another dA, and the synthesis was interrupted before the last oxidation step. The column was detached from synthesiser, drained on a water pump, rinsed with MeCN, and the support with attached phosphite was transferred into a plastic tube.

Second aliquot of 50 µl was transferred into the tube with support, vortexed for 30 s, centrifugated at 14,500 rpm for 30 s and shaken for 30 min at ambient temperature. Supernatant was discarded, the support was rinsed with 2×200 µl MeCN, transferred into a synthesiser column, and the synthesis was resumed until the end of the sequence.

The oligonucleotide was detached from support and protecting groups removed by Soln A for 12 h at 55° C.

Molecular mass: calc. [M] 3200.38, exp. [M−H] 3199.51.

Example 13. Preparation of a Modified Oligonucleotide 5'-d(GCGCCApAACpA) (SEQ ID NO: 15) with the N,N,N',N'-tetramethyl Phosphoryl Guanidine Group (FVIII)

A column containing 5 mg of 5'-DMTr-dA(Bz) CPG support (110 μmol g$^{-1}$) was placed into a DNA synthesiser, and automated β-cyanoethyl phosphoramidite solid-phase DNA synthesis was started on 0.2 μmol scale. Synthesis was interrupted after 5'-detritylation, dC phosphoramidite coupling and capping but before oxidation. The column was detached from synthesiser, drained on a water pump, rinsed with MeCN, and the support with attached phosphite was transferred into a plastic tube.

An aliquot of 80 μl 0.5 M bis(dimethylamino)-1-azidocarbenium dichlorophosphate was transferred into a plastic tube, 20 μl BSA was added and the tube was vortexed for 1 min, centrifuged at 14,500 rpm for 1 min and left for 30 min at ambient temperature. An aliquot of 50 μl was transferred into the tube with support, vortexed for 30 s, centrifuged at 14,500 rpm for 30 s and shaken for 30 min at ambient temperature. Supernatant was discarded, the support was rinsed with 2×200 μl MeCN, transferred into a synthesiser column, then two dA phosphoramidites were coupled followed by another dA, and the synthesis was interrupted before the last oxidation step. The column was detached from synthesiser, drained on a water pump, rinsed with MeCN, and the support with attached phosphite was transferred into a plastic tube.

Second aliquot of 50 μl was transferred into the tube with support, vortexed for 30 s, centrifuged at 14,500 rpm for 30 s and shaken for 30 min at ambient temperature. Supernatant was discarded, the support was rinsed with 2×200 μl MeCN, transferred into a synthesiser column, and the synthesis was resumed until the end of the sequence.

The oligonucleotide was detached from support and protecting groups removed by Soln A for 12 h at 55° C.

Molecular mass: calc. [M] 3200.38, exp. [M−H] 3199.15.

Example 14. Preparation of a Modified Oligonucleotide 5'-d(GCGCCAApApCpA) (SEQ ID NO: 12) with the N,N,N',N'-tetramethyl Phosphoryl Guanidine Group (FVIII)

A column containing 5 mg of 5'-DMTr-dA(Bz) CPG support (110 μmol g$^{-1}$) was placed into a DNA synthesiser, and automated β-cyanoethyl phosphoramidite solid-phase DNA synthesis was started on 0.2 μmol scale. Synthesis was interrupted after 5'-detritylation, dC phosphoramidite coupling and capping but before oxidation. The column was detached from synthesiser, drained on a water pump, rinsed with MeCN, and the support with attached phosphite was transferred into a plastic tube.

An aliquot of 120 μl 0.5 M bis(dimethylamino)-1-azidocarbenium dichlorophosphate was transferred into a plastic tube, 30 μl BSA was added and the tube was vortexed for 1 min, centrifuged at 14,500 rpm for 1 min and left for 30 min at ambient temperature. An aliquot of 50 μl was transferred into the tube with support, vortexed for 30 s, centrifuged at 14,500 rpm for 30 s and shaken for 30 min at ambient temperature. Supernatant was discarded, the support was rinsed with 2×200 μl MeCN, transferred into a synthesiser column, a dA phosphoramidite was coupled and the synthesis was interrupted before oxidation. The column was detached from synthesiser, drained on a water pump, rinsed with MeCN, and the support with attached phosphite was transferred into a plastic tube.

Second aliquot of 50 μl was transferred into the tube with support, vortexed for 30 s, centrifuged at 14,500 rpm for 30 s and shaken for 30 min at ambient temperature. Supernatant was discarded, the support was rinsed with 2×200 μl MeCN, transferred into a synthesiser column, a dA phosphoramidite was coupled and the synthesis was interrupted before oxidation. The column was detached from synthesiser, drained on a water pump, rinsed with MeCN, and the support with attached phosphite was transferred into a plastic tube.

Third aliquot of 50 μl was transferred into the tube with support, vortexed for 30 s, centrifuged at 14,500 rpm for 30 s and shaken for 30 min at ambient temperature. Supernatant was discarded, the support was rinsed with 2×200 μl MeCN, transferred into a synthesiser column, and the synthesis was resumed until the end of the sequence.

The oligonucleotide was detached from support and protecting groups removed by Soln A for 12 h at 55° C. An HPLC trace of the oligonucleotide is given in FIG. 1.

Molecular mass: calc. [M] 3297.54, exp. [M−H] 3296.80.

Example 15. Preparation of a Modified Oligonucleotide 5'-d(GGAAGGGGAGAGpA) (SEQ ID NO: 3) with the N,N,N',N'-tetramethyl Phosphoryl Guanidine Group (FVIII)

A column containing 5 mg of 5'-DMTr-dA(Bz) CPG support (110 μmol g$^{-1}$) was placed into a DNA synthesiser, and automated β-cyanoethyl phosphoramidite solid-phase DNA synthesis was started on 0.2 μmol scale. Synthesis was interrupted after 5'-detritylation, dG phosphoramidite coupling and capping but before oxidation. The column was detached from synthesiser, drained on a water pump, rinsed with MeCN, and the support with attached phosphite was transferred into a plastic tube.

An aliquot of 40 μl 0.5 M bis(dimethylamino)-1-azidocarbenium dichlorophosphate was transferred into a plastic tube, 10 μl BSA was added and the tube was vortexed for 1 min, centrifuged at 14,500 rpm for 1 min and left for 30 min at ambient temperature. The content was transferred into the tube with support, vortexed for 30 s, centrifuged at 14,500 rpm for 30 s and shaken for 30 min at ambient temperature. Supernatant was discarded, the support was rinsed with 2×200 μl MeCN, transferred into a synthesiser column, and the synthesis was resumed until the end of the sequence.

The oligonucleotide was detached from support and protecting groups removed by Soln A for 16 h at 55° C.

Molecular mass: calc. [M] 4234.94, exp. [M−H] 4233.84.

Example 16. Preparation of a Modified Oligonucleotide 5'-d(TTTTTTTTTTTTTTTTTTTpT) (SEQ ID NO: 16) with the N,N,N',N'-tetramethyl Phosphoryl Guanidine Group (FVIII)

A column containing 5 mg of High Load 5'-DMTr-dT CPG support (110 μmol g$^{-1}$) was placed into a DNA synthesizer, and automated β-cyanoethyl phosphoramidite solid-phase DNA synthesis was started on 0.2 umol scale. Synthesis was interrupted after 5'-detritylation, phosphoramidite coupling and capping but before oxidation. The column was detached from synthesiser, drained on a water pump, rinsed with MeCN, and the support with attached phosphite was transferred into a plastic tube.

Soln 1 was prepared by dissolving iodine crystals in dry pyridine to 0.2 M concentration (51 mg per ml). Soln 2 was prepared by mixing 124 µl TMG, 50 µl BSA and 325 µl dry pyridine, and adding 3 Å molecular sieves to ca. ¼ vol. Aliquots of 20 µl of Soln 1 and 2 were mixed in a plastic tube, 10 µl of BSA were added, and after 1 min wait the content was transferred to the tube with polymer. The tube was vortexed for 30 s, centrifugated at 14,500 rpm for 15 s and shaken for 5 min at ambient temperature. Supernatant was discarded, the support was rinsed with 2×200 µl MeCN, transferred into a synthesiser column, and β-cyanoethyl phosphoramidite solid-phase synthesis was resumed until the end of the sequence.

The oligonucleotide was detached from support and protecting groups removed by Soln A for 2 h at ambient temperature.

Molecular mass: calc. [M] 6119.16, exp. [M+H] 6121.13, [M−H] 6113.80.

Example 17. Preparation of a Modified Oligonucleotide 5'-d(TTTTTTTTTTpTTTTTTTTT) (SEQ ID NO: 17) with the N,N,N',N'-tetramethyl Phosphoryl Guanidine Group (FVIII)

A column containing 5 mg of High Load 5'-DMTr-dT CPG support (110 µmol g$^{-1}$) was placed into a DNA synthesizer, and automated β-cyanoethyl phosphoramidite solid-phase DNA synthesis was started on 0.2 umol scale. Synthesis was interrupted after eight cycles of dT incorporation followed by 5'-detritylation, another dT phosphoramidite coupling and capping but before oxidation. The column was detached from synthesiser, drained on a water pump, rinsed with MeCN, and the support with attached phosphite was transferred into a plastic tube.

Soln 1 was prepared by dissolving iodine crystals in dry pyridine to 0.2 M concentration (51 mg per ml). Soln 2 was prepared by mixing 124 µl TMG, 50 µl BSA and 325 µl dry pyridine, and adding 3 Å molecular sieves to ca. ¼ vol. Aliquots of 20 µl of Soln 1 and 2 were mixed in a plastic tube, 10 µl of BSA were added, and after 1 min wait the content was transferred to the tube with polymer. The tube was vortexed for 30 s, centrifugated at 14,500 rpm for 15 s and shaken for 5 min at ambient temperature. Supernatant was discarded, the support was rinsed with 2×200 µl MeCN, transferred into a synthesiser column, and β-cyanoethyl phosphoramidite solid-phase synthesis was resumed until the end of the sequence.

The oligonucleotide was detached from support and protecting groups removed by Soln A for 2 h at ambient temperature.

Molecular mass: calc. [M] 6119.16, exp. [M+H] 6121.54.

Example 18. Preparation of a Modified Oligonucleotide 5'-d(TTpTTTTTTTTTTTTTTTTT) (SEQ ID NO: 18) with the N,N,N',N'-tetramethyl Phosphoryl Guanidine Group (FVIII)

A column containing 5 mg of High Load 5'-DMTr-dT CPG support (110 µmol g$^{-1}$) was placed into a DNA synthesizer, and automated β-cyanoethyl phosphoramidite solid-phase DNA synthesis was started on 0.2 µmol scale. Synthesis was interrupted after 17 cycles of dT incorporation followed by 5'-detritylation, another dT phosphoramidite coupling and capping but before oxidation. The column was detached from synthesiser, drained on a water pump, rinsed with MeCN, and the support with attached phosphite was transferred into a plastic tube.

Soln 1 was prepared by dissolving iodine crystals in dry pyridine to 0.2 M concentration (51 mg per ml). Soln 2 was prepared by mixing 124 µl TMG, 50 µl BSA and 325 µl dry pyridine, and adding 3 Å molecular sieves to ca. ¼ vol. Aliquots of 20 µl of Soln 1 and 2 were mixed in a plastic tube, 10 µl of BSA were added, and after 1 min wait the content was transferred to the tube with polymer. The tube was vortexed for 30 s, centrifugated at 14,500 rpm for 15 s and shaken for 5 min at ambient temperature. Supernatant was discarded, the support was rinsed with 2×200 µl MeCN, transferred into a synthesiser column, and β-cyanoethyl phosphoramidite solid-phase synthesis was resumed until the end of the sequence.

The oligonucleotide was detached from support and protecting groups removed by Soln A for 2 h at ambient temperature.

Molecular mass: calc. [M] 6119.16, exp. [M+H] 6120.01, [M−H] 6114.19.

Example 19. Preparation of a Modified Oligonucleotide 5'-d(TTpTTTTTTTTTTTTTTTpT) (SEQ ID NO: 19) with the N,N,N',N'-tetramethyl Phosphoryl Guanidine Group (FVIII)

A column containing 5 mg of High Load 5'-DMTr-dT CPG support (110 µmol g$^{-1}$) was placed into a DNA synthesizer, and automated β-cyanoethyl phosphoramidite solid-phase DNA synthesis was started on 0.2 umol scale. Synthesis was interrupted after 5'-detritylation, dT phosphoramidite coupling and capping but before oxidation. The column was detached from synthesiser, drained on a water pump, rinsed with MeCN, and the support with attached phosphite was transferred into a plastic tube.

An aliquot of 80 µl 0.5 M bis(dimethylamino)-1-azidocarbenium dichlorophosphate was transferred into a plastic tube, 20 µl BSA was added and the tube was vortexed for 1 min, centrifugated at 14,500 rpm for 1 min and left for 30 min at ambient temperature. An aliquot of 50 µl was transferred into the tube with support, vortexed for 30 s, centrifugated at 14,500 rpm for 30 s and shaken for 30 min at ambient temperature. Supernatant was discarded, the support was rinsed with 2×200 µl MeCN, transferred into a synthesiser column, the synthesis was resumed by incorporating 17 dT nucleotides and stopped after another dT coupling and capping but before oxidation. The column was detached from synthesiser, drained on a water pump, rinsed with MeCN, and the support with attached phosphite was transferred into a plastic tube.

Second aliquot of 50 µl was transferred into the tube with support, vortexed for 30 s, centrifugated at 14,500 rpm for 30 s and shaken for 30 min at ambient temperature. Supernatant was discarded, the support was rinsed with 2×200 µl MeCN, transferred into a synthesiser column, and the synthesis was resumed until the end of the sequence.

The oligonucleotide was detached from support and protecting groups removed by Soln A for 2 h at ambient temperature.

Molecular mass: calc. [M] 6216.33, exp. [M−H] 6221.11.

Example 20. Preparation of a Modified Oligonucleotide 5'-d(TTpTTTTTTTTpTTTTTTTpT) (SEQ ID NO: 20) with the N,N,N',N'-tetramethyl Phosphoryl Guanidine Group (FVIII)

A column containing 5 mg of High Load 5'-DMTr-dT CPG support (110 µmol g$^{-1}$) was placed into a DNA synthesiser, and automated β-cyanoethyl phosphoramidite solid-phase DNA synthesis was started on 0.2 µmol scale. Synthesis was interrupted after 5'-detritylation, dT phosphoramidite coupling and capping but before oxidation. The column was detached from synthesiser, drained on a water pump, rinsed with MeCN, and the support with attached phosphite was transferred into a plastic tube.

An aliquot of 120 µl 0.5 M bis(dimethylamino)-1-azido-carbenium dichlorophosphate was transferred into a plastic tube, 30 µl BSA was added and the tube was vortexed for 1 min, centrifugated at 14,500 rpm for 1 min and left for 30 min at ambient temperature. An aliquot of 50 µl was transferred into the tube with support, vortexed for 30 s, centrifugated at 14,500 rpm for 30 s and shaken for 30 min at ambient temperature. Supernatant was discarded, the support was rinsed with 2×200 µl MeCN, transferred into a synthesiser column, eight dT nucleotides were incorporated and the synthesis was interrupted on the last dT before oxidation. The column was detached from synthesiser, drained on a water pump, rinsed with MeCN, and the support with attached phosphite was transferred into a plastic tube.

Second aliquot of 50 µl was transferred into the tube with support, vortexed for 30 s, centrifugated at 14,500 rpm for 30 s and shaken for 30 min at ambient temperature. Supernatant was discarded, the support was rinsed with 2×200 µl MeCN, transferred into a synthesiser column, nine dT nucleotides were incorporated and the synthesis was interrupted on the last dT before oxidation. The column was detached from synthesiser, drained on a water pump, rinsed with MeCN, and the support with attached phosphite was transferred into a plastic tube.

Third aliquot of 50 µl was transferred into the tube with support, vortexed for 30 s, centrifugated at 14,500 rpm for 30 s and shaken for 30 min at ambient temperature. Supernatant was discarded, the support was rinsed with 2×200 µl MeCN, transferred into a synthesiser column, and the synthesis was resumed for the last dT nucleotide incorporation.

The oligonucleotide was detached from support and protecting groups removed by Soln A for 2 h at ambient temperature.

Molecular mass: calc. [M] 6313.49, exp. [M−H] 6310.71.

Example 21. Preparation of a Modified Oligonucleotide 5'-d(TTTTTTTTTTTTTTTTTTTpT) (SEQ ID NO: 21) with the Phosphoryl Guanidine Group (FIX)

A column containing 5 mg of High Load 5'-DMTr-dT CPG support (110 µmol g$^{-1}$) was placed into a DNA synthesizer, and automated β-cyanoethyl phosphoramidite solid-phase DNA synthesis was started on 0.2 µmol scale. Synthesis was interrupted after four dT incorporations followed by 5'-detritylation, phosphoramidite coupling and capping but before oxidation. The column was detached from synthesiser, drained on a water pump, rinsed with MeCN, and the support with attached phosphite was transferred into a plastic tube.

Soln 1 was prepared by dissolving iodine crystals in dry pyridine to 0.2 M concentration (51 mg per ml). Soln 2 was prepared by weighing 9.6 mg of dried guanidine hydrochloride into a plastic tube, adding 85 µl dry pyridine, 15 µl DBU, 10 µl BSA, and the tube was vortexed for 5 min and sonicated until clear (ca. 5 min). Aliquots of 20 µl of Soln 1 and 2 were mixed in a plastic tube, 10 µl of BSA were added, and after 1 min wait the content was transferred to the tube with polymer. The tube was vortexed for 30 s, centrifugated at 14,500 rpm for 15 s and shaken for 5 min at ambient temperature. Supernatant was discarded, the support was rinsed with 2×200 µl MeCN, transferred into a synthesiser column, and the synthesis was resumed until the end of the sequence.

The oligonucleotide was detached from support and protecting groups removed by Soln A for 1 h at ambient temperature.

Molecular mass: calc. [M] 6063.05, exp. [M+H] 6065.02, [M−H] 6058.30.

Example 22. Preparation of a Modified Oligodeoxyribonucleotide 5'-d(TTTT)tpdT with the N,N,N',N'-tetramethyl Phosphoryl Guanidine Group (FVIII); t Here and in the Following Example Indicates Position of LNA-T Nucleotide A column containing 5 mg of High Load 5'-DMTr-dT CPG support (110 µmol g$^{-1}$) was placed into a DNA synthesizer, and automated β-cyanoethyl phosphoramidite solid-phase DNA synthesis was started on 0.2 µmol scale. The coupling step for LNA-T incorporation was extended to 6 min. Synthesis was interrupted after 5'-detritylation, LNA-T phosphoramidite coupling and capping but before oxidation. The column was detached from synthesiser, drained on a water pump, rinsed with MeCN, and the support with attached phosphite was transferred into a plastic tube.

An aliquot of 40 µl 0.5 M bis(dimethylamino)-1-azido-carbenium dichlorophosphate was transferred into a plastic tube, 10 µl BSA was added and the tube was vortexed for 1 min, centrifugated at 14,500 rpm for 1 min and left for 30 min at ambient temperature. Then the content was transferred into the tube with support, vortexed for 30 s, centrifugated at 14,500 rpm for 30 s and shaken for 1 h at 40° C. Supernatant was discarded, the support was rinsed with 2×200 µl MeCN, transferred into a synthesiser column, and the synthesis was resumed until the end of the sequence.

The oligonucleotide was detached from support and protecting groups removed by Soln A for 1 h at ambient temperature. An RP-HPLC trace of the oligonucleotide is shown in FIG. 3.

Molecular mass: calc. [M] 1888.40, exp. [M+H] 1888.15, [M−H] 1886.86.

Example 23. Preparation of a Modified Oligodeoxyribonucleotide 5'-tpd(TTTTT) with the N,N,N',N'-tetramethyl Phosphoryl Guanidine Group (FVIII); p Indicates Position of Modified Phosphate Group; t Indicates Position of LNA-T Nucleotide A column containing 5 mg of High Load 5'-DMTr-dT CPG support (110 µmol g$^{-1}$) was placed into a DNA synthesizer, and automated β-cyanoethyl phosphoramidite solid-phase DNA synthesis was started on 0.2 µmol scale. The coupling step for LNA-T incorporation was extended to 6 min. Synthesis was interrupted after four cycles of dT incorporation, 5'-detritylation, LNA-T phosphoramidite coupling and capping but before oxidation. The column was detached from synthesiser, drained on a water pump, rinsed with MeCN, and the support with attached phosphite was transferred into a plastic tube.

An aliquot of 40 µl 0.5 M bis(dimethylamino)-1-azido-carbenium dichlorophosphate was transferred into a plastic tube, 10 µl BSA was added and the tube was vortexed for 1 min, centrifugated at 14,500 rpm for 1 min and left for 30 min at ambient temperature. The content was transferred into the tube with support, vortexed for 30 s, centrifugated at 14,500 rpm for 30 s and shaken for 1 h at 40° C. Supernatant was discarded, the support was rinsed with 2×200 µl MeCN, transferred into a synthesiser column, and the synthesis was completed by 5'-detritylation.

The oligonucleotide was detached from support and protecting groups removed by Soln A for 1 h at ambient temperature. An RP-HPLC trace of the oligonucleotide is shown in FIG. 3.

Molecular mass: calc. [M] 1888.40, exp. [M+H] 1888.27, [M–H] 1887.44.

Example 24. Preparation of a Modified Oligonucleotide 5'-d(AACGTCAGGGTCTTCCp)BHQ (SEQ ID NO: 4) with the N,N,N',N'-tetramethyl Phosphoryl Guanidine Group (Formula XIV). Here and in the Following Example, BHQ is BlackHole Quencher™ (FXII)

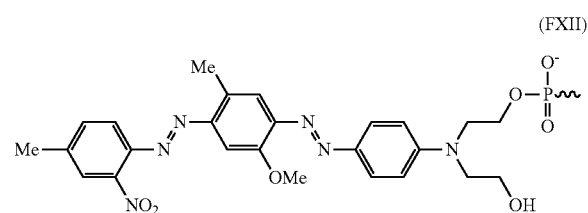

(FXII)

A column containing 5 mg of BHQ CPG support (42 µmol g⁻¹) was placed into a DNA synthesizer, and automated β-cyanoethyl phosphoramidite solid-phase DNA synthesis was started on 0.2 µmol scale. Synthesis was interrupted after 5'-detritylation, dC phosphoramidite coupling and capping but before oxidation. The column was detached from synthesiser, drained on a water pump, rinsed with MeCN, and the support with attached phosphite was transferred into a plastic tube.

An aliquot of 40 µl 0.5 M bis(dimethylamino)-1-azidocarbenium dichlorophosphate was transferred into a plastic tube, 10 µl BSA was added and the tube was vortexed for 1 min, centrifugated at 14,500 rpm for 1 min and left for 30 min at ambient temperature. Then the content was transferred into the tube with support, vortexed for 30 s, centrifugated at 14,500 rpm for 30 s and shaken for 30 min at ambient temperature. Supernatant was discarded, the support was rinsed with 2×200 µl MeCN, transferred into a synthesiser column, and the synthesis was resumed until the end of the sequence.

The oligonucleotide was detached from support and protecting groups removed by Soln A for 12 h at 55° C.

Molecular mass: calc. [M] 5510.92, exp. [M–H] 5509.50.

Example 25. Preparation of a Modified Oligonucleotide 5'-Flu d(GGAAG DD CCCTGACGTTp) BHQ (SEQ ID NO: 5) with the N,N,N',N'-tetramethyl Phosphoryl Guanidine Group (FVIII). DD is 1,12-Dodecanediol Phosphate (FXIII), Flu is 5(6)-Carboxyfluorescein Label (FXIV)

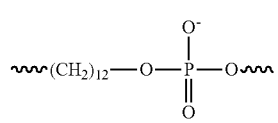

(FXIII)

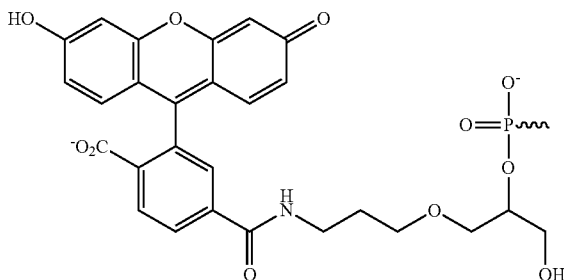

(FXIV)

A column containing 5 mg of BHQ CPG support (42 µmol g⁻¹) was placed into a DNA synthesizer, and automated β-cyanoethyl phosphoramidite solid-phase DNA synthesis was started on 0.2 µmol scale. Synthesis was interrupted after 5'-detritylation, dT phosphoramidite coupling and capping but before oxidation. The column was detached from synthesiser, drained on a water pump, rinsed with MeCN, and the support with attached phosphite was transferred into a plastic tube.

An aliquot of 40 µl 0.5 M bis(dimethylamino)-1-azidocarbenium dichlorophosphate was transferred into a plastic tube, 10 µl BSA was added and the tube was vortexed for 1 min, centrifugated at 14,500 rpm for 1 min and left for 30 min at ambient temperature. Then the content was transferred into the tube with support, vortexed for 30 s, centrifugated at 14,500 rpm for 30 s and shaken for 30 min at ambient temperature. Supernatant was discarded, the support was rinsed with 2×200 µl MeCN, transferred into a synthesiser column, and the synthesis was resumed until the end of the sequence using the corresponding 1,12-dodecanediol and fluorescein phosphoramidites as modifiers.

The oligonucleotide was detached from support and protecting groups removed by Soln A for 12 h at 55° C.

Molecular mass: calc. [M] 6078.50, exp. [M+H] 6084.38.

Example 26. Preparation of a Modified Oligonucleotide 5'-d(TCTCTCpFCCTTCpC) (SEQ ID NO: 6) with the N,N,N',N'-tetramethyl Phosphoryl Guanidine Group (Formula XIV). F Here and in the Next Example is 2-hydroxymethyl-3-hydroxytetrahydrofurane (Apurinic/Apyrimidinic Site) Phosphate (FXV)

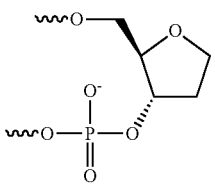

(FXV)

A column containing 5 mg of 5'-DMTr-dC(Bz) CPG support (110 µmol g⁻¹) was placed into a DNA synthesiser, and automated β-cyanoethyl phosphoramidite solid-phase DNA synthesis was started on 0.2 µmol scale. Synthesis was interrupted after 5'-detritylation, dC phosphoramidite coupling and capping but before oxidation. The column was detached from synthesiser, drained on a water pump, rinsed with MeCN, and the support with attached phosphite was transferred into a plastic tube.

An aliquot of 80 μl 0.5 M bis(dimethylamino)-1-azidocarbenium dichlorophosphate was transferred into a plastic tube, 20 μl BSA was added and the tube was vortexed for 1 min, centrifuged at 14,500 rpm for 1 min and left for 30 min at ambient temperature. An aliquot of 50 μl was transferred into the tube with support, vortexed for 30 s, centrifuged at 14,500 rpm for 30 s and shaken for 30 min at ambient temperature. Supernatant was discarded, the support was rinsed with 2×200 μl MeCN, transferred into a synthesiser column, five nucleotides ere incorporated including the dF unit until the next dC nucleotide, where the synthesis was interrupted before the oxidation step. The column was detached from synthesiser, drained on a water pump, rinsed with MeCN, and the support with attached phosphite was transferred into a plastic tube.

Second aliquot of 50 μl was transferred into the tube with support, vortexed for 30 s, centrifuged at 14,500 rpm for 30 s and shaken for 30 min at ambient temperature. Supernatant was discarded, the support was rinsed with 2×200 μl MeCN, transferred into a synthesiser column, and the synthesis was resumed until the end of the sequence.

The oligonucleotide was detached from support and protecting groups removed by Soln A for 16 h at ambient temperature.

Molecular mass: calc. [M] 3857.76, exp. [M−H] 3856.74.

Example 27. Preparation of a Modified Oligonucleotide 5'-d(GCGCCAAACpA) (SEQ ID NO: 22) with the 1,3-dimethyl-2-(phosphorylimino)imidazolidine Group (FXVI)

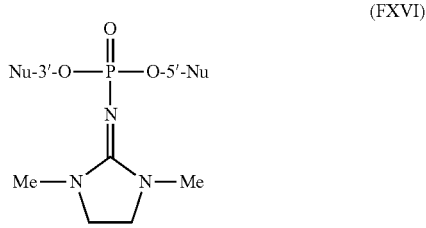

(FXVI)

A column containing 5 mg of 5'-DMTr-dA(Bz) CPG support (110 μmol g$^{-1}$) was placed into a DNA synthesiser, and automated β-cyanoethyl phosphoramidite solid-phase DNA synthesis was started on 0.2 μmol scale. Synthesis was interrupted after 5'-detritylation, dC phosphoramidite coupling and capping but before oxidation. The column was detached from synthesiser, drained on a water pump, rinsed with MeCN, and the support with attached phosphite was transferred into a plastic tube.

To 100 μl 1 M 2-azido-4,5-dihydro-1,3-dimethyl-1H-imidazolium hexafluorophosphate 25 μl BSA and 5 μl triethylamine were added, and the tube was vortexed for 1 min, centrifuged at 14,500 rpm for 30 s and shaken for 1 h at ambient temperature. Supernatant was discarded, the support was rinsed with 2×200 μl MeCN, transferred into a synthesiser column, and the synthesis was resumed until the end of the sequence.

The oligonucleotide was detached from support and protecting groups removed by Soln A for 12 h at 55° C.

Molecular mass: calc. [M] 3101.20, exp. [M−H] 3101.55.

Example 28. Preparation of a Modified Oligonucleotide 5'-d(GCGCCAAACpA) (SEQ ID NO: 23) with the N,N'-bis(tetramethylene)-N"-phosphoryl Guanidine Group (FXVII)

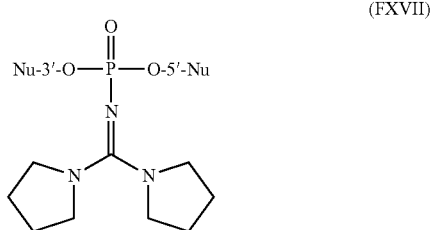

(FXVII)

A column containing 5 mg of 5'-DMTr-dA(Bz) CPG support (110 μmol g$^{-1}$) was placed into a DNA synthesiser, and automated β-cyanoethyl phosphoramidite solid-phase DNA synthesis was started on 0.2 μmol scale. Synthesis was interrupted after 5'-detritylation, dC phosphoramidite coupling and capping but before oxidation. The column was detached from synthesiser, drained on a water pump, rinsed with MeCN, and the support with attached phosphite was transferred into a plastic tube.

To 100 μl 1 M azidodipyrrolidinocarbenium hexafluorophosphate 25 μl BSA and 5 μl triethylamine were added, and the tube was vortexed for 1 min, centrifuged at 14,500 rpm for 1 min and left for 30 min at ambient temperature. The content was transferred into the tube with support, vortexed for 30 s, centrifuged at 14,500 rpm for 30 s and shaken for 1 h at ambient temperature. Supernatant was discarded, the support was rinsed with 2×200 μl MeCN, transferred into a synthesiser column, and the synthesis was resumed until the end of the sequence.

The oligonucleotide was detached from support and protecting groups removed by Soln A for 12 h at 55° C.

Molecular mass: calc. [M] 3155.29, exp. [M−H] 3153.75.

Example 29. Preparation of a Modified oligo-2'-O-Methylribonucleotide 5'-AUCGpU with the N,N,N',N'-tetramethyl Phosphoryl Guanidine Group (FVIII)

A column containing 5 mg of 5'-DMTr-2'-OMe-rU CPG support (40 μmol g$^{-1}$) was placed into a DNA synthesiser, and automated β-cyanoethyl phosphoramidite solid-phase oligo-2'-O-methylribonucleotide synthesis was started on 0.2 μmol scale. Synthesis was interrupted after 5'-detritylation, 2'-OMe-rG phosphoramidite coupling and capping but before oxidation. The column was detached from synthesiser, drained on a water pump, rinsed with MeCN, and the support with attached phosphite was transferred into a plastic tube.

An aliquot of 40 μl 0.5 M bis(dimethylamino)-1-azidocarbenium dichlorophosphate was transferred into a plastic tube, 10 μl BSA was added and the tube was vortexed for 1 min, centrifuged at 14,500 rpm for 1 min and left for 30 min at ambient temperature. The content was transferred into the tube with support, vortexed for 30 s, centrifuged at 14,500 rpm for 30 s and shaken for 30 min at ambient temperature. Supernatant was discarded, the support was rinsed with 2×200 μl MeCN, transferred into a synthesiser column, and the synthesis was resumed until the end of the sequence.

The oligonucleotide was detached from support and protecting groups removed by Soln A for 16 h at 55° C.

Molecular mass: calc. [M] 1697.28, exp. [M+H] 1697.59, [M−H] 1694.77.

Example 30. Preparation of a Modified oligo-2'-O-methylribonucleotide 5'-GCGCCAAACpA (SEQ ID NO: 11) with the N,N,N',N'-tetramethyl Phosphoryl Guanidine Group (FVIII)

A column containing 5 mg of 5'-DMTr-2'-OMe-rA(Bz) CPG support (60 µmol g$^{-1}$) was placed into a DNA synthesiser, and automated β-cyanoethyl phosphoramidite solid-phase oligo-2'-O-methylribonucleotide synthesis was started on 0.2 µmol scale. Synthesis was interrupted after 5'-detritylation, 2'-OMe-rC phosphoramidite coupling and capping but before oxidation. The column was detached from synthesiser, drained on a water pump, rinsed with MeCN, and the support with attached phosphite was transferred into a plastic tube.

An aliquot of 40 µl 0.5 M bis(dimethylamino)-1-azido-carbenium dichlorophosphate was transferred into a plastic tube, 10 µl BSA was added and the tube was vortexed for 1 min, centrifugated at 14,500 rpm for 1 min and left for 30 min at ambient temperature. The content was transferred into the tube with support, vortexed for 30 s, centrifugated at 14,500 rpm for 30 s and shaken for 1 h at 40° C. Supernatant was discarded, the support was rinsed with 2×200 µl MeCN, transferred into a synthesiser column, and the synthesis was resumed until the end of the sequence.

The oligonucleotide was detached from support and protecting groups removed by Soln A for 12 h at 55° C.

Molecular mass: calc. [M] 3403.48, exp. [M−H] 3402.55.

Example 31. Preparation of a Modified oligo-2'-O-methylribonucleotide 5'-GCGCCAAApCpA (SEQ ID NO: 24) with the N,N,N',N'-tetramethyl Phosphoryl Guanidine Group (FVIII)

A column containing 5 mg of 5'-DMTr-2'-OMe-rA(Bz) CPG support (60 µmol g$^{-1}$) was placed into a DNA synthesiser, and automated β-cyanoethyl phosphoramidite solid-phase oligo-2'-O-methylribonucleotide synthesis was started on 0.2 µmol scale. Synthesis was interrupted after 5'-detritylation, 2'-OMe-rC phosphoramidite coupling and capping but before oxidation. The column was detached from synthesiser, drained on a water pump, rinsed with MeCN, and the support with attached phosphite was transferred into a plastic tube.

An aliquot of 80 µl 0.5 M bis(dimethylamino)-1-azido-carbenium dichlorophosphate was transferred into a plastic tube, 20 µl BSA was added and the tube was vortexed for 1 min, centrifugated at 14,500 rpm for 1 min and left for 30 min at ambient temperature. An aliquot of 50 µl was transferred into the tube with support, vortexed for 30 s, centrifugated at 14,500 rpm for 30 s and shaken for 1 h at 40° C. Supernatant was discarded, the support was rinsed with 2×200 µl MeCN, transferred into a synthesiser column, a 2'-OMe-rU phosphoramidite was coupled and the synthesis was interrupted before oxidation. The column was detached from synthesiser, drained on a water pump, rinsed with MeCN, and the support with attached phosphite was transferred into a plastic tube.

Second aliquot of 50 µl was transferred into the tube with support, vortexed for 30 s, centrifugated at 14,500 rpm for 30 s and shaken for 1 h at 40° C. Supernatant was discarded, the support was rinsed with 2×200 µl MeCN, transferred into a synthesiser column, and the synthesis was resumed until the end of the sequence.

The oligonucleotide was detached from support and protecting groups removed by Soln A for 12 h at 55° C.

Molecular mass: calc. [M] 3500.64, exp. [M+H] 3199.90, [M−H] 3499.75.

Example 32. Preparation of a modified oligo-2'-O-methylribonucleotide Phosphorothioate 5'-G$_s$A$_s$C$_s$A$_s$U$_s$C$_s$C$_s$A$_s$U$_s$U$_s$C$_s$A$_s$A$_s$A$_s$A$_s$U$_s$G$_s$G$_s$U$_s$UpUpG (SEQ ID NO: 8) with N,N,N',N'-tetramethyl Phosphoryl Guanidine Group (Formula XIV); $_s$ Here and in the Following Examples Indicates Phosphorothioate Residue (FXVIII)

(FXVIII)

A column containing 5 mg of 5'-DMTr-2'-OMe-rG(Tac) CPG support (60 µmol g$^{-1}$) was placed into a DNA synthesiser, and automated β-cyanoethyl phosphoramidite solid-phase oligo-2'-O-methylribonucleotide synthesis was started on 0.2 µmol scale. Synthesis was interrupted after 5'-detritylation, 2'-OMe-rU phosphoramidite coupling and capping but before oxidation. The column was detached from synthesiser, drained on a water pump, rinsed with MeCN, and the support with attached phosphite was transferred into a plastic tube.

An aliquot of 80 µl 0.5 M bis(dimethylamino)-1-azido-carbenium dichlorophosphate was transferred into a plastic tube, 20 µl BSA was added and the tube was vortexed for 1 min, centrifugated at 14,500 rpm for 1 min and left for 30 min at ambient temperature. An aliquot of 50 µl was transferred into the tube with support, vortexed for 30 s, centrifugated at 14,500 rpm for 30 s and shaken for 1 h at 40° C. Supernatant was discarded, the support was rinsed with 2×200 µl MeCN, transferred into a synthesiser column, a 2'-OMe-rA phosphoramidite was coupled and the synthesis was interrupted before oxidation. The column was detached from synthesiser, drained on a water pump, rinsed with MeCN, and the support with attached phosphite was transferred into a plastic tube.

Second aliquot of 50 µl was transferred into the tube with support, vortexed for 30 s, centrifugated at 14,500 rpm for 30 s and shaken for 1 h at 40° C. Supernatant was discarded, the support was rinsed with 2×200 µl MeCN, transferred into a synthesiser column, and the synthesis was resumed substituting sulfurisation with 0.1 M 3-[(dimethylaminomethylene)imino]-3H-1,2,4-dithiazole-3-thione in dry pyridine for iodine oxidation until the end of the sequence.

The oligonucleotide was detached from support and protecting groups removed by Soln A for 3 h at 70° C.

Molecular mass: calc. [M] 7436.14, exp. [M−H] 7433.89.

Example 33. Preparation of a modified oligo-2'-O-methylribonucleotide Phosphorothioate 5'-Flu G$_s$A$_s$C$_s$A$_s$U$_s$C$_s$C$_s$A$_s$U$_s$U$_s$C$_s$A$_s$A$_s$A$_s$U$_s$G$_s$G$_s$U$_s$Up-UpG (SEQ ID NO: 8) with N,N,N',N'-tetramethyl Phosphoryl Guanidine Group (FVIII); Flu Indicates 5'-Fluorescein Label (FXIXV); $_s$ Indicates Phosphorothioate Residue (FXVIII)

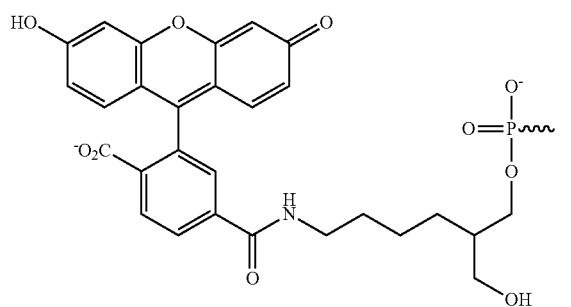

(FXIX)

A column containing 5 mg of 5'-DMTr-2'-OMe-rG(Tac) CPG support (60 μmol g$^{-1}$) was placed into a DNA synthesiser, and automated β-cyanoethyl phosphoramidite solid-phase oligo-2'-O-methylribonucleotide synthesis was started on 0.2 μmol scale. Synthesis was interrupted after 5'-detritylation, 2'-OMe-rU phosphoramidite coupling and capping but before oxidation. The column was detached from synthesiser, drained on a water pump, rinsed with MeCN, and the support with attached phosphite was transferred into a plastic tube.

An aliquot of 80 μl 0.5 M bis(dimethylamino)-1-azidocarbenium dichlorophosphate was transferred into a plastic tube, 20 μl BSA was added and the tube was vortexed for 1 min, centrifugated at 14,500 rpm for 1 min and left for 30 min at ambient temperature. An aliquot of 50 μl was transferred into the tube with support, vortexed for 30 s, centrifugated at 14,500 rpm for 30 s and shaken for 1 h at 40° C. Supernatant was discarded, the support was rinsed with 2×200 μl MeCN, transferred into a synthesiser column, a 2'-OMe-rA phosphoramidite was coupled and the synthesis was interrupted before oxidation. The column was detached from synthesiser, drained on a water pump, rinsed with MeCN, and the support with attached phosphite was transferred into a plastic tube.

Second aliquot of 50 μl was transferred into the tube with support, vortexed for 30 s, centrifugated at 14,500 rpm for 30 s and shaken for 1 h at 40° C. Supernatant was discarded, the support was rinsed with 2×200 μl MeCN, transferred into a synthesiser column, and the synthesis was resumed substituting sulfurisation with 0.1 M 3-[(dimethylaminomethylene)imino]-3H-1,2,4-dithiazole-3-thione in dry pyridine for iodine oxidation until the end of the sequence. The synthesis was completed by the incorporation of the corresponding fluorescein phosphoramidite in DMTr ON mode.

The oligonucleotide was detached from support and protecting groups removed by Soln A for 3 h at 70° C.

Molecular mass: calc. [M] 8003.63, exp. [M−H] 8001.25.

Example 34. Preparation of a Modified oligo-2'-O-methylribonucleotide Phosphorothioate 5'-Flu G$_s$G$_s$C$_s$C$_s$A$_s$A$_s$A$_s$C$_s$C$_s$U$_s$C$_s$C$_s$G$_s$C$_s$UpUpACpCpU (SEQ ID NO: 9) with N,N,N',N'-tetramethyl Phosphoryl Guanidine Group (FVIII); Flu Indicates 5'-Fluorescein Label (FXIX); $_s$ Indicates Phosphorothioate Residue (FXVIII)

A column containing 5 mg of 5'-DMTr-2'-OMe-rU CPG support (40 μmol g$^{-1}$) was placed into a DNA synthesiser, and automated β-cyanoethyl phosphoramidite solid-phase oligo-2'-O-methylribonucleotide synthesis was started on 0.2 μmol scale. Synthesis was interrupted after 5'-detritylation, 2'-OMe-rC phosphoramidite coupling and capping but before oxidation. The column was detached from synthesiser, drained on a water pump, rinsed with MeCN, and the support with attached phosphite was transferred into a plastic tube.

An aliquot of 160 μl 0.5 M bis(dimethylamino)-1-azidocarbenium dichlorophosphate was transferred into a plastic tube, 40 μl BSA was added and the tube was vortexed for 1 min, centrifugated at 14,500 rpm for 1 min and left for 30 min at ambient temperature. An aliquot of 50 μl was transferred into the tube with support, vortexed for 30 s, centrifugated at 14,500 rpm for 30 s and shaken for 1 h at 40° C. Supernatant was discarded, the support was rinsed with 2×200 μl MeCN, transferred into a synthesiser column, a 2'-OMe-rC phosphoramidite was coupled and the synthesis was interrupted before oxidation. The column was detached from synthesiser, drained on a water pump, rinsed with MeCN, and the support with attached phosphite was transferred into a plastic tube.

Second aliquot of 50 μl was transferred into the tube with support, vortexed for 30 s, centrifugated at 14,500 rpm for 30 s and shaken for 1 h at 40° C. Supernatant was discarded, the support was rinsed with 2×200 μl MeCN, transferred into a synthesiser column, a 2'-OMe-rA phosphoramidite was coupled followed by 2'-OMe-rU and the synthesis was interrupted before the last oxidation step. The column was detached from synthesiser, drained on a water pump, rinsed with MeCN, and the support with attached phosphite was transferred into a plastic tube.

Third aliquot of 50 μl was transferred into the tube with support, vortexed for 30 s, centrifugated at 14,500 rpm for 30 s and shaken for 1.5 h at 45° C. Supernatant was discarded, the support was rinsed with 2×200 μl MeCN, transferred into a synthesiser column, a 2'-OMe-rU phosphoramidite was coupled and the synthesis was interrupted before oxidation. The column was detached from synthesiser, drained on a water pump, rinsed with MeCN, and the support with attached phosphite was transferred into a plastic tube.

Fourth aliquot of 50 μl was transferred into the tube with support, vortexed for 30 s, centrifugated at 14,500 rpm for 30 s and shaken for 1.5 h at 45° C. Supernatant was discarded, the support was rinsed with 2×200 μl MeCN, transferred into a synthesiser column, and the synthesis was resumed substituting sulfurisation with 0.1 M 3-[(dimethylaminomethylene)imino]-3H-1,2,4-dithiazole-3-thione in dry pyridine for iodine oxidation until the end of the sequence. The synthesis was completed by the incorporation of the corresponding fluorescein phosphoramidite in DMTr ON mode.

The oligonucleotide was detached from support and protecting groups removed by Soln A for 3 h at 70° C.

Molecular mass: calc. [M] 7763.48, exp. [M−H] 7759.37.

Example 35. Preparation of a mixed LNA-oligo-2'-O-methylribonucleotide Phosphorothioate 5'-Flu G$_s$g$_s$C$_s$g$_s$A$_s$a$_s$A$_s$C$_s$c$_s$U$_s$C$_s$C$_s$c$_s$C$_s$UpUpaCpCpU (SEQ ID NO: 10) with N,N,N',N'-tetramethyl Phosphoryl Guanidine Group (FVIII); Flu Indicates 5'-Fluorescein Label (FXIX); $_s$ Indicates Phosphorothioate Residue (FXVIII). LNA Nucleotides A, 5-Me-C and G are Shown by Lowercase Letters a, c and g, Respectively A column containing 5 mg of 5'-DMTr-2'-OMe-rU CPG support (40 µmol g$^{-1}$) was placed into a DNA synthesiser, and automated β-cyanoethyl phosphoramidite solid-phase oligo-2'-O-methylribonucleotide synthesis was started on 0.2 µmol scale. Synthesis was interrupted after 5'-detritylation, 2'-OMe-rC phosphoramidite coupling and capping but before oxidation. The column was detached from synthesiser, drained on a water pump, rinsed with MeCN, and the support with attached phosphite was transferred into a plastic tube.

An aliquot of 160 µl 0.5 M bis(dimethylamino)-1-azidocarbenium dichlorophosphate was transferred into a plastic tube, 40 µl BSA was added and the tube was vortexed for 1 min, centrifuged at 14,500 rpm for 1 min and left for 30 min at ambient temperature. An aliquot of 50 µl was transferred into the tube with support, vortexed for 30 s, centrifuged at 14,500 rpm for 30 s and shaken for 1 h at 40° C. Supernatant was discarded, the support was rinsed with 2×200 µl MeCN, transferred into a synthesiser column, a 2'-OMe-rC phosphoramidite was coupled and the synthesis was interrupted before oxidation. The column was detached from synthesiser, drained on a water pump, rinsed with MeCN, and the support with attached phosphite was transferred into a plastic tube.

Second aliquot of 50 µl was transferred into the tube with support, vortexed for 30 s, centrifuged at 14,500 rpm for 30 s and shaken for 1 h at 40° C. Supernatant was discarded, the support was rinsed with 2×200 µl MeCN, transferred into a synthesiser column, an LNA-A phosphoramidite was coupled followed by 2'-OMe-rU and the synthesis was interrupted before the last oxidation step. The column was detached from synthesiser, drained on a water pump, rinsed with MeCN, and the support with attached phosphite was transferred into a plastic tube.

Third aliquot of 50 µl was transferred into the tube with support, vortexed for 30 s, centrifuged at 14,500 rpm for 30 s and shaken for 1.5 h at 45° C. Supernatant was discarded, the support was rinsed with 2×200 µl MeCN, transferred into a synthesiser column, a 2'-OMe-rU phosphoramidite was coupled and the synthesis was interrupted before oxidation. The column was detached from synthesiser, drained on a water pump, rinsed with MeCN, and the support with attached phosphite was transferred into a plastic tube.

Fourth aliquot of 50 µl was transferred into the tube with support, vortexed for 30 s, centrifuged at 14,500 rpm for 30 s and shaken for 1.5 h at 45° C. Supernatant was discarded, the support was rinsed with 2×200 µl MeCN, transferred into a synthesiser column, and the synthesis was resumed substituting sulfurisation with 0.1 M 3-[(dimethylaminomethylene)imino]-3H-1,2,4-dithiazole-3-thione in dry pyridine for iodine oxidation and using LNA and 2'-OMe phosphoramidites until the end of the sequence. The synthesis was completed by the incorporation of the corresponding fluorescein phosphoramidite in DMTr ON mode.

The oligonucleotide was detached from support and protecting groups removed by Soln A for 3 h at 70° C.

Molecular mass: calc. [M] 7793.47, exp. [M−H] 7792.92.

Example 36. Preparation of a Modified oligo-2'-O-methylribonucleotide 5'-UUUUUpU with the 1,3-dimethyl-2-(phosphorylimino)imidazolidine Group (FXVI)

A column containing 5 mg of 5'-DMTr-2'-OMe-rU CPG support (40 µmol g$^{-1}$) was placed into a DNA synthesiser, and automated β-cyanoethyl phosphoramidite solid-phase oligo-2'-O-methylribonucleotide synthesis was started on 0.2 µmol scale. Synthesis was interrupted after 5'-detritylation, 2'-OMe-rU phosphoramidite coupling and capping but before oxidation. The column was detached from synthesiser, drained on a water pump, rinsed with MeCN, and the support with attached phosphite was transferred into a plastic tube.

To 100 µl 1 M 2-azido-4,5-dihydro-1,3-dimethyl-1H-imidazolium hexafluorophosphate 25 µl BSA and 5 µl triethylamine were added, and the tube was vortexed for 1 min, centrifuged at 14,500 rpm for 1 min and left for 30 min at ambient temperature. The content was transferred into the tube with support, vortexed for 30 s, centrifuged at 14,500 rpm for 30 s and shaken for 1 h at ambient temperature. Supernatant was discarded, the support was rinsed with 2×200 µl MeCN, transferred into a synthesiser column, and the synthesis was resumed until the end of the sequence.

The oligonucleotide was detached from support and protecting groups removed by Soln A for 1 h at ambient temperature. An RP-HPLC trace of the oligonucleotide is shown in FIG. 4.

Molecular mass: calc. [M] 1954.37, exp. [M−H] 1953.37.

Example 37. Preparation of a Modified oligo-2'-O-methylribonucleotide 5'-UUUUUpU with the N,N'-bis(tetramethylene)-N''-phosphoryl Guanidine Group (FXVII)

A column containing 5 mg of 5'-DMTr-2'-OMe-rU CPG support (40 µmol g$^{-1}$) was placed into a DNA synthesiser, and automated β-cyanoethyl phosphoramidite solid-phase oligo-2'-O-methylribonucleotide synthesis was started on 0.2 µmol scale. Synthesis was interrupted after 5'-detritylation, 2'-OMe-rU phosphoramidite coupling and capping but before oxidation. The column was detached from synthesiser, drained on a water pump, rinsed with MeCN, and the support with attached phosphite was transferred into a plastic tube.

To 100 µl 1 M azidodipyrrolidinocarbenium hexafluorophosphate 25 µl BSA and 5 µl triethylamine were added, and the tube was vortexed for 1 min, centrifuged at 14,500 rpm for 1 min and left for 30 min at ambient temperature. The content was transferred into the tube with support, vortexed for 30 s, centrifuged at 14,500 rpm for 30 s and shaken for 1 h at ambient temperature. Supernatant was discarded, the support was rinsed with 2×200 µl MeCN, transferred into a synthesiser column, and the synthesis was resumed until the end of the sequence.

The oligonucleotide was detached from support and protecting groups removed by Soln A for 1 h at ambient temperature. An RP-HPLC trace of the oligonucleotide is shown in FIG. 4.

Molecular mass: calc. [M] 2008.46, exp. [M−H] 2007.57.

Example 38. Preparation of a Modified Oligonucleotide 5'-d(TTTTTpT) with the N,N-dimethyl Phosphoryl Guanidine Group (FXX)

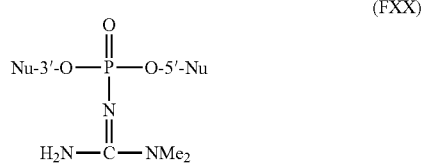

A column containing 5 mg of High Load 5'-DMTr-dT CPG support (110 µmol g$^{-1}$) was placed into a DNA synthesizer, and automated β-cyanoethyl phosphoramidite solid-phase DNA synthesis was started on 0.2 µmol scale. Synthesis was interrupted after 5'-detritylation, phosphoramidite coupling and capping but before oxidation. The column was detached from synthesiser, drained on a water pump, rinsed with MeCN, and the support with attached phosphite was transferred into a plastic tube.

To 12 mg of (chloromethylene)dimethyliminium chloride and 4 mg (1.1 equiv) NaN$_3$ in a plastic tube, 100 µl dry MeCN were added and the tube was shaken for 2 h at 30° C., centrifugated at 14,500 rpm for 5 min, 25 µl BSA were added, the tube vortexed for 1 min, centrifugated at 14,500 rpm for 1 min and the supernatant was transferred into the tube with support, vortexed for 30 s, centrifugated at 14,500 rpm for 30 s and shaken for 30 min at ambient temperature. Supernatant was discarded, the support was rinsed with 2×200 µl MeCN, transferred into a synthesiser column, and β-cyanoethyl phosphoramidite solid-phase synthesis was resumed until the end of the sequence.

The oligonucleotide was detached from support and protecting groups removed by Soln A for 18 h at 55° C.

Molecular mass: calc. [M] 1832.22, exp. [M−H] 1831.57.

Example 39. Preparation of a Modified Oligonucleotide 5'-d(TTTTTpT) with the N-phosphoryl Formamidine Group (FXXI)

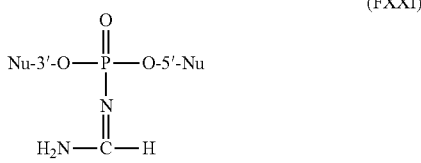

A column containing 5 mg of High Load 5'-DMTr-dT CPG support (110 µmol g$^{-1}$) was placed into a DNA synthesizer, and automated β-cyanoethyl phosphoramidite solid-phase DNA synthesis was started on 0.2 µmol scale. Synthesis was interrupted after 5'-detritylation, phosphoramidite coupling and capping but before oxidation. The column was detached from synthesiser, drained on a water pump, rinsed with MeCN, and the support with attached phosphite was transferred into a plastic tube.

Soln 1 was prepared by dissolving iodine crystals in dry pyridine to 0.2 M concentration (51 mg per ml). Soln 2 was prepared by weighing 40 mg of dried formamidine hydrochloride into a plastic tube, adding 375 µl dry pyridine, 75 µl DBU and 50 µl BSA, and the tube was vortexed for 3-4 min and sonicated until clear (ca. 3-4 min). Aliquots of 20 µl of Soln 1 and 2 were mixed in a plastic tube, 10 µl of BSA were added, and after 1 min wait the content was transferred to the tube with polymer. The tube was vortexed for 30 s, centrifugated at 14,500 rpm for 15 s and shaken for 5 min at ambient temperature. Supernatant was discarded, the support was rinsed with 2×200 µl MeCN, transferred into a synthesiser column, and β-cyanoethyl phosphoramidite solid-phase synthesis was resumed until the end of the sequence.

The oligonucleotide was detached from support and protecting groups removed by Soln A for 1 h at ambient temperature.

Molecular mass: calc. [M] 1789.27, exp. [M−H] 1788.60.

Example 40. Preparation of a Modified Oligonucleotide 5'-d(TTTTTpT) with the N-cyanoimino Phosphate Group (FXXII)

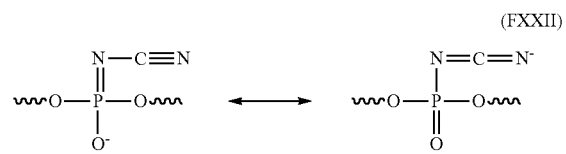

A column containing 5 mg of High Load 5'-DMTr-dT CPG support (110 µmol g$^{-1}$) was placed into a DNA synthesizer, and automated β-cyanoethyl phosphoramidite solid-phase DNA synthesis was started on 0.2 umol scale. Synthesis was interrupted after 5'-detritylation, phosphoramidite coupling and capping but before oxidation. The column was detached from synthesiser, drained on a water pump, rinsed with MeCN, and the support with attached phosphite was transferred into a plastic tube.

To 20 µl 0.25 M solution of cyanogen azide in dry MeCN prepared as described by McMurry [51] 5 µl BSA were added and the tube was kept for 15 min at ambient temperature, the content was transferred into the tube with support, vortexed for 30 s, centrifugated at 14,500 rpm for 15 s and shaken for 5 min at ambient temperature. Supernatant was discarded, the support was rinsed with 2×200 µl MeCN, transferred into a synthesiser column, and β-cyanoethyl phosphoramidite solid-phase synthesis was resumed until the end of the sequence.

The oligonucleotide was detached from support and protecting groups removed by Soln B for 1 h at 70° C.

Molecular mass: calc. [M] 1787.25, exp. [M+H] 1787.27, [M−H] 1785.19.

Example 41. Preparation of a Modified Oligonucleotide 5'-d(TpTTTTT) with the N-cyanoimino Phosphate Group (FXXII)

A column containing 5 mg of High Load 5'-DMTr-dT CPG support (110 µmol g$^{-1}$) was placed into a DNA synthesizer, and automated β-cyanoethyl phosphoramidite solid-phase DNA synthesis was started on 0.2 µmol scale. Synthesis was interrupted after four cycles of dT incorporation, 5'-detritylation, dT phosphoramidite coupling and capping but before oxidation. The column was detached from synthesiser, drained on a water pump, rinsed with MeCN, and the support with attached phosphite was transferred into a plastic tube.

To 20 μl 0.25 M solution of cyanogen azide in dry MeCN prepared as described by McMurry [51] 5 μl BSA were added and the tube was kept for 15 min at ambient temperature, the content was transferred into the tube with support, vortexed for 30 s, centrifugated at 14,500 rpm for 15 s and shaken for 5 min at ambient temperature. Supernatant was discarded, the support was rinsed with 2×200 μl MeCN, transferred into a synthesiser column, and β-cyanoethyl phosphoramidite solid-phase synthesis was resumed until the end of the sequence.

The oligonucleotide was detached from support and protecting groups removed by Soln B for 1 h at 70° C. An RP-HPLC of the oligonucleotide is shown in FIG. 5.

Molecular mass: calc. [M] 1787.25, exp. [M+H] 1787.19, [M−H] 1785.11.

Example 42. Preparation of a Modified Nucleoside dTp with the 3'-N,N'-bis(tetramethylene)-N''-guanidinophosphate Group (FXXIII)

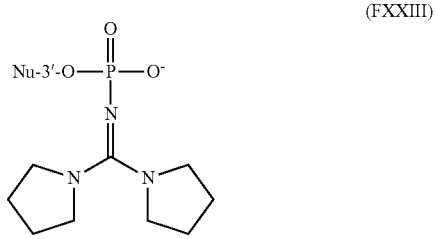

(FXXIII)

A column containing 5 mg of 3'-phosphate CPG support (30-40 μmol g$^{-1}$) was placed into a DNA synthesizer, and automated β-cyanoethyl phosphoramidite solid-phase DNA synthesis was started on 0.2 μmol scale. Synthesis was interrupted after 5'-detritylation, dT phosphoramidite coupling and capping but before oxidation. The column was detached from synthesiser, drained on a water pump, rinsed with MeCN, and the support with attached phosphite was transferred into a plastic tube.

To 100 μl 1 M azidodipyrrolidinocarbenium hexafluorophosphate 25 μl BSA and 5 μl triethylamine were added, and the tube was vortexed for 1 min, centrifugated at 14,500 rpm for 1 min and left for 30 min at ambient temperature. The content was transferred into the tube with support, vortexed for 30 s, centrifugated at 14,500 rpm for 30 s and shaken for 1 h at ambient temperature. Supernatant was discarded, the support was rinsed with 2×200 μl MeCN, transferred into a synthesiser column, and the synthesis was completed by 5'-detritylation.

The nucleotide was detached from support by Soln A for 1 h at ambient temperature. Molecular mass: calc. [M] 471.45, exp. [M−H] 471.08.

Example 43. Preparation of a Modified Oligonucleotide 5'-d(TTTTTT)p with the 3'-N,N'-bis(tetramethylene)-N''-guanidinophosphate Group (FXXIII)

A column containing 5 mg of 3'-phosphate CPG support (30-40 μmol g$^{-1}$) was placed into a DNA synthesizer, and automated β-cyanoethyl phosphoramidite solid-phase DNA synthesis was started on 0.2 μmol scale. Synthesis was interrupted after 5'-detritylation, dT phosphoramidite coupling and capping but before oxidation. The column was detached from synthesiser, drained on a water pump, rinsed with MeCN, and the support with attached phosphite was transferred into a plastic tube.

To 100 μl 1 M azidodipyrrolidinocarbenium hexafluorophosphate 25 μl BSA and 5 μl triethylamine were added, and the tube was vortexed for 1 min, centrifugated at 14,500 rpm for 1 min and left for 30 min at ambient temperature. The content was transferred into the tube with support, vortexed for 30 s, centrifugated at 14,500 rpm for 30 s and shaken for 1 h at ambient temperature. Supernatant was discarded, the support was rinsed with 2×200 μl MeCN, transferred into a synthesiser column, and the synthesis was resumed until the end of the sequence.

The nucleotide was detached from support by Soln A for 1 h at ambient temperature. An RP-HPLC of the oligonucleotide is shown in FIG. 6.

Molecular mass: calc. [M] 1992.44, exp. [M−H] 1991.46.

Example 44. Preparation of a Modified Thymidine Nucleoside with the 5'-N,N'-bis(tetramethylene)-N''-phosphorylguanidine Group and a Fluorescein Label (FXXIV)

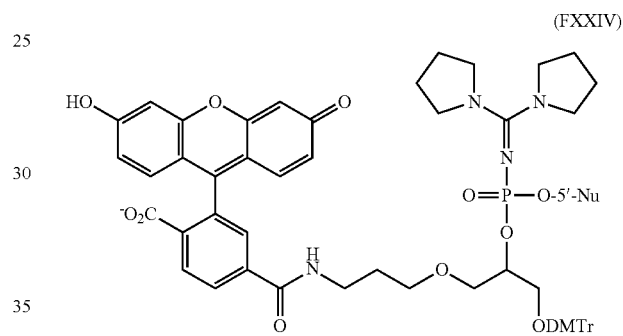

(FXXIV)

A column containing 5 mg of High Load 5'-DMTr-dT CPG support (110 μmol g$^{-1}$) was placed into a DNA synthesizer, and automated β-cyanoethyl phosphoramidite solid-phase DNA synthesis was started on 0.2 μmol using the same fluorescein phosphoramidite as in Example 25. Synthesis was interrupted before oxidation, the column was detached from synthesiser, drained on a water pump, rinsed with MeCN, and the support with attached phosphite was transferred into a plastic tube.

To 100 μl 1 M azidodipyrrolidinocarbenium hexafluorophosphate 25 μl BSA and 5 μl triethylamine were added, and the tube was vortexed for 1 min, centrifugated at 14,500 rpm for 1 min and left for 30 min at ambient temperature. The content was transferred into the tube with support, vortexed for 30 s, centrifugated at 14,500 rpm for 30 s and shaken for 1 h at ambient temperature. Supernatant was discarded, the support was rinsed with 2×200 μl MeCN and dried on air for 5 min.

The nucleotide was detached from support by Soln A for 1 h at ambient temperature. An RP-HPLC of the oligonucleotide is shown in FIG. 6.

Molecular mass: calc. [M] 1263.32, exp. [M−H] 1262.22.

Example 45. Preparation of a Modified Oligonucleotide 5'-Flu pd(TTTTTT) with the 5'-N,N'-bis(tetramethylene)-N''-phosphoryl Guanidine Group and a Fluorescein Label (FXXIV)

A column containing 5 mg of High Load 5'-DMTr-dT CPG support (110 μmol g$^{-1}$) was placed into a DNA synthesizer, and automated β-cyanoethyl phosphoramidite solid-phase DNA synthesis was started on 0.2 µmol. Synthesis was interrupted after incorporation of five dT residues and a fluorescein label Flu' (XXV) but before the last oxidation step. The column was detached from synthesiser, drained on a water pump, rinsed with MeCN, and the support with attached phosphite was transferred into a plastic tube.

To 100 µl 1 M azidodipyrrolidinocarbenium hexafluorophosphate 25 µl BSA and 5 µl triethylamine were added, and the tube was vortexed for 1 min, centrifuged at 14,500 rpm for 1 min and left for 30 min at ambient temperature. The content was transferred into the tube with support, vortexed for 30 s, centrifugated at 14,500 rpm for 30 s and shaken for 1 h at ambient temperature. Supernatant was discarded, the support was rinsed with 2×200 µl MeCN and dried on air for 5 min.

The oligonucleotide was detached from support by Soln A for 1 h at ambient temperature. An RP-HPLC of the oligonucleotide is shown in FIG. 6.

Molecular mass: calc. [M] 2784.31, exp. [M–H] 2782.96.

Example 46. Preparation of a Modified Hybrid DNA-RNA Oligonucleotide 5'-d(TTTT)rUpdT with the 1,3-dimethyl-2-(phosphorylimino)imidazolidine Group (FXVI)

A column containing 5 mg of High Load 5'-DMTr-dT CPG support (110 µmol g$^{-1}$) was placed into a DNA synthesiser, and automated β-cyanoethyl phosphoramidite solid-phase oligonucleotide synthesis was started on 0.2 µmol scale. Synthesis was interrupted after 5'-detritylation, 2'-TOM-rU phosphoramidite coupling and capping but before oxidation. The column was detached from synthesiser, drained on a water pump, rinsed with MeCN, and the support with attached phosphite was transferred into a plastic tube.

To 100 µl 1 M 2-azido-4,5-dihydro-1,3-dimethyl-1H-imidazolium hexafluorophosphate 25 µl BSA and 5 µl triethylamine were added, and the tube was vortexed for 1 min, centrifugated at 14,500 rpm for 1 min and left for 30 min at ambient temperature. The content was transferred into the tube with support, vortexed for 30 s, centrifugated at 14,500 rpm for 30 s and shaken for 1 h at ambient temperature. Supernatant was discarded, the support was rinsed with 2×200 µl MeCN, transferred into a synthesiser column, and the synthesis was resumed until the end of the sequence.

The oligonucleotide was detached from support and protecting groups removed by Soln A for 1 h at ambient temperature. The TOM group was then removed by triethylamine trihydrofluoride-triethylamine-NMP (4:3:6 v/v/v) at 65° C. for 2 h.

Molecular mass: calc. [M] 1860.34, exp. [M–H] 1859.21.

Example 47. A Protocol for Preparation of oligodeoxyribonucleotides 5'-d(TTTTTpT), 5'-d(TTTTpTpT), 5'-d(TTTpTpTpT), 5'-d(TTpTpTpTpT), 5'-d(TpTpTpTpTpT) vi 5'-d(GpCpGpCpCpApApApCpA) (SEQ ID NO: 1) modified with 1,3-dimethyl-N-phosphorylimino-2-imidazolidine Groups (FXVI) Using an Automated DNA Synthesiser A column containing 5 mg of either 5'-DMTr-dT or dA CPG support (35-110 µmol g$^{-1}$) was placed into a DNA synthesizer, and automated β-cyanoethyl phosphoramidite solid-phase DNA synthesis was started on 0.2 µmol scale substituting treatment with 1 M 2-azido-4,5-dihydro-1,3-dimethyl-1H-imidazolium hexafluorophosphate in dry acetonitrile for iodine oxidation for the corresponding positions (p) within the sequence.

Oligonucleotides were detached from support by Soln A for 12 h at 55° C. for oligonucleotide 5'-d(GpCpGpCpCpApApApCpA) (SEQ ID NO: 1) or for 1 h at ambient temperature for oligothymidylates. An RP-HPLC of the oligonucleotides is shown in FIGS. 7 and 8.

Molecular Masses:
5'-d(TTTTTpT)—calc. [M] 1858.37, exp. [M–H] 1857.57;
5'-d(TTTTpTpT)—calc. [M] 1953.32, exp. [M–H] 1952.57;
5'-d(TTTpTpTpT)—calc. [M] 2048.67, exp. [M–H] 2047.77;
5'-d(TTpTpTpTpT)—calc. [M] 2143.82, exp. [M–H] 2142.77;
5'-d(TpTpTpTpTpT)—calc. [M] 2238.96, exp. [M–H] 2237.97;
5'-d(GpCpGpCpCpApApApCpA) (SEQ ID NO: 1)—calc. [M] 3862.38, exp. [M–H] 3860.50.

REFERENCES

A number of publications are cited herein in order more fully to describe and disclose the invention and the state of the art to which the invention pertains. Full citations for these references are provided below. Each of these references is incorporated herein by reference in its entirety into the present disclosure, to the same extent as if each individual reference was specifically and individually indicated to be incorporated by reference.

(1) *Therapeutic Oligonucleotides*, J. Goodchild (ed.), *Methods Mol. Biol.* 764, Humana Press, 2011.
(2) Bell, N. M.; Micklefield, *J. Chem Bio Chem* 2009, 10, 2691.
(3) Mulamba, G. B.; Hu, A.; Azad, R. F.; Anderson, K. P.; Coen, D. M. *Antimicrob. Agents Chemother.* 1998, 42, 971.
(4) Vinores, S. A. *Int. J. Nanomed.* 2006, 1, 263.
(5) Merki, E.: Graham, M. J.; Mullick, A. E. et al. *Circulation* 2008, 118, 743.
(6) Duca, M.; Vekhoff, P.; Oussedik, K.; Halby, L.; Arimondo, P. B. *Nucl. Acids Res.* 2008, 36, 5123.
(7) Nielsen, P. E. *Curr. Opin. Mol. Ther.* 2010, 12, 184.
(8) Zamecnik, P. C.; Stephenson, M. L. *Proc. Natl. Acad. Sci. USA* 1978, 75, 280.
(9) Behlke, M. A. *Oligonucleotides* 2008, 18, 305.
(10) Xu, Z. J.; Yang, L. F.; Sun, L. Q.; Cao, Y. *Chin. Sci. Bull.* 2012, 57, 3404.
(11) Wilson, C.; Keefe, A. D. *Curr. Opin. Chem. Biol.* 2006, 10, 607.
(12) Lee, J. F.; Stovall, G. M.; Ellington, A. D. *Curr. Opin. Chem. Biol.* 2006, 10, 282.
(13) Du, L.; Gatti, R. A. *Curr. Opin. Mol. Ther.* 2009, 11, 116; Pérez, B.; Laura Rodriguez-Pascau, L.; Vilageliu, L.; Grinberg, D.; Ugarte, M.; Desviat, L. R. *J. Inherit Metabol. Disease* 2010, 33, 397.
(14) Ruckman, J.; Green, L. S.; Beeson, J.; Waugh, S.; Gillette, W. L.; Henninger, D. D.; Claesson-Welsh, L.; Janjić, N. *J. Biol. Chem.* 1998, 273, 20556.
(15) Lamond, A. I.; Sproat, B. S. *FEBS Lett.* 1993, 325, 123.
(16) Chi, K. N.; Eisenhauer, E.; Jones, E. C.; Goldenberg, S. L., Powers, J.; Tu, D.; Gleave, M. E. *J. Natl. Cancer Inst.* 2005, 97, 1287.

(17) Kaur, H.; Babu, B. R.; Maiti, S. *Chem. Rev.* 2007, 107, 4672.
(18) Jáger, A.; Engels, *J. Tetrahedron Lett.* 1984, 25, 1437.
(19) Hau, J. F.; Asseline, U.; Thuong, N. T. *Tetrahedron Lett.* 1991, 32, 2497.
(20) Jager, A.; Levy, M. J.; Hecht, S. M. Biochemistry 1988, 27, 7237.
(21) Egholm. M.; Buchardt, O.; Nielsen, P. E.; Berg, R. H. *J. Am. Chem. Soc.* 1992, 114, 1895.
(22) Summerton, J.; Weller, D. *Antisense Nucl. Acid Drug Dev.* 1997, 7, 187.
(23) Stein, C. A.; Subasinghe, C.; Shinozuka, K.; Cohen, J. S. *Nucl. Acids Res.* 1988, 16, 3209.
(24) Pâtureau, B. M.; Hudson, R. H. E.; Damha, M. J. *Bioconjugate Chem.* 2007, 18, 421.
(25) Crooke, S. T. *Methods Enzymol.* 2000, 313, 3.
(26) Behlke, M. A. *Oligonucleotides* 2008, 18, 305.
(27) Xu, Z. J.; Yang, L. F.; Sun, L. Q.; Cao, Y. *Chin. Sci. Bull.* 2012, 57, 3404.
(28) Stec, W. J.; Zon, G.; Egan, W.; Stec, B. *J. Am. Chem. Soc.* 1984, 106, 6077.
(29) Seeberger, P. H.; Caruthers, M. H. *J. Am. Chem. Soc.* 1995, 117, 1472.
(30) Hall, A. H.; Wan, J.; Spesock, A.; Sergueeva, Z.; Shaw, B. R.; Alexander, K. A. *Nucleic Acids Res.* 2006, 34, 2773.
(31) Beaucage, S. L.; Caruthers, M. H. *Tetrahedron Lett.* 1981, 22, 1859.
(32 Sazani, P.; Kang, S.-H.; Maier, M. A.; Wei, C.; Dillman, J.; Summerton, J.; Manoharan, M.; Kole, R. *Nucl. Acids Res.* 2001, 29, 3965.
(33) Froehler, B.; Ng, P.; Matteucci, M. *Nucl. Acids Res.* 1988, 16, 4831.
(34) Dolinnaya, N. G.; Sokolova, N. I.; Gryaznova, O. I.; Shabarova, Z. A. *Nucl. Acids Res.* 1988, 16, 3721.
(35) Mignet, N.; Gryaznov, S. M. *Nucl. Acids Res.* 1998, 26, 431.
(36) Letsinger, R. L.; Singman, C. N.; Histand, G.; Salunkhe, M. *J. Am. Chem. Soc.* 1988, 110, 4470.
(37) Summerton, J.; Weller, D. Antisense *Nucl. Acid Drug Dev.* 1997, 7, 187.
(38) Dellinger et al. *J. Am. Chem. Soc.* 2003, 125, 940.
(39) Yamada et al. *J. Am. Chem. Soc.* 2006, 128, 5251.
(40) Krishna, H.; Caruthers, M. H. *J. Am. Chem. Soc.* 2012, 134, 11618.
(41) WO2007/059816 A1 and WO2008/128686 A1.
(42) Summerton, J.; Weller, D. Antisense *Nucl. Acid Drug Dev.* 1997, 7, 187.
(43) Mendell, J.; Rodino-Klapac, L. R.; Sahenk, Z.; Roush, K.; Bird, L.; Lowes, L. P.; Alfano, L.; Gomez, A. M.; Lewis, A.; Kota, J. et al. *Ann. Neurol.* 2013, 74, 637; www.clinicaltrials.gov/ct2/show/NCT01396239.
(44) mail. pi pelinereview.com/index.php/2014021053402/DNA-RNA-and-Cells/Sarepta-Therapeutics-Announces-Positive-Safety-Results-from-Phase-I-Clinical-Study-of-Marburg-Drug- Candidate.html.
(45) Summerton, J. E. In *Peptide Nucleic Acids, Morpholinos and Related Antisense Biomolecules* (Janson, C. G.; During, M. J., Eds), 2003, Kluwer Academic/Plenum Publishers, Chapter 6.
(46) Summerton, J.; Weller, D. Antisense *Nucl. Acid Drug Dev.* 1997, 7, 187.
(47) Reese, C. B., Ubasawa, A. *Tetrahedron Lett.* 1980, 21, 2265.
(48) Jones, S. S.; Reese, C. B.; Sibanda, S.; Ubasawa, A. *Tetrahedron Lett.* 1981, 22, 4755.
(49) Swenson, D. L.; Warfield, K. L.; Warren, T. K.; Lovejoy, C.; Hassinger, J. N.; Ruthel, G.; Blouch, R. E.; Moulton, H. M.; Weller, D. D.; Iversen, P. L.; Bavari, S. *Antimicrob. Agents Chemother.* 2009, 53, 2089; Mellbye, B. M.; Weller, D. D.; Hassinger, J. N.; Reeves, M. D.; Lovejoy, C. E.; Iversen, P. L.; Geller, B. L. *J. Antimicrob. Chemother.* 2010, 65, 98.
(50) Jearawiriyapaisarn, N.; Moulton, H. M.; Buckley, B.; Roberts, J.; Sazani, P.; Fucharoen, S.; Iversen, P. L.; Kole, R. *Mol. Ther.* 2008, 16, 1624; Wu, B.; Moulton, H. M.; Iversen, P. L.; Juang, J.; Li, J.; Spurney, C. F.; Sali, A.; Guerron, A. D.; Nagaraju, K.; Doran, T. et al. *Proc. Natl. Acad. Sci. USA* 2008, 105, 14814; Yin, H.; Moulton, H. M.; Seow, Y.; Boyd, C.; Boutilier, J.; Iversen, P.; Wood, M. J. A. *Human Mol. Genetics* 2008, 17, 3909.
(51) McMurry, J. E.; Coppolino, A. P. *J. Org. Chem.* 1973, 38, 2821.
(52) Alimov, P. I.; Levkova, L. N. Izv. Akad. Nauk SSSR, Ser. Khim. 1964, 1889; Cates, L. A.; Ferguson, N. M. *J. Pharm. Chem.* 1966, 55, 966.
(53) Rathgeb, P., U.S. Pat. No. 4,154,826 A, priority date 30 Dec. 1976.
(54) Sherif, F. G., U.S. Pat. No. 3,634,555 A, priority date 31 Jul. 1969.
(55) Anatol, J.; Vidalenc, H.; Loiseau, G., U.S. Pat. No. 3,769,406 A, priority date 19 Jun. 1970.
(56) Lin, W. O.; Guimarates, C. N.; De Souza, J. B. N.; Alt, H. G. Phosphorus Sulfur 1994, 92, 1.
(57) Jager, A.; Levy, M. J.; Hecht, S. M. Biochemistry 1988, 27, 7237.
(58) Sinha, N. D.; Biernat, J.; McManus, J.; Köster, H. *Nucleic Acids Res.* 1984, 12, 4539.
(59) Xi, S.-K.; Zhao, Y.-F. Synth. Commun. 1990, 20, 3295.
(60) Kitamura, M.; Yano, M.; Tashiro, N.; Miyagawa, S.; Sando, M.; Okauchi, T. *Eur. J. Org. Chem.* 2011, 458.
(61) Kokel, B.; Viehe, H. G. *Angew. Chem. Int. Ed. Engl.* 1980, 19, 716.
(62) Boyd, G. V.; Lindley, P. F.; Mitchell, J. C.; Nicolaou, G. A. *J. Chem. Soc. Chem. Commun.* 1985, 1522.
(63) Garegg, P. J.; Lindh, I.; Regberg, T.; Stawinski, J.; Strömberg, R. Tetrahedron Lett. 1986, 27, 4051.
(64) Atherton, F. R.; Openshaw, H. T.; Todd, A. R. *J. Chem. Soc.* 1945, 660.
(65) Barnett, R. W.; Letsinger, R. L. Tetrahedron Lett. 1981, 22, 991.
(66) Froehler, B. C.; Ng, P. G.; Matteucci, M. D. *Nucleic Acids Res.* 1986, 14, 5399.
(67) Bezgubenko, L. V.; Pipko, S. E.; Shalimov, A. A.; Sinitsa, A. D. *Heteroatom Chemistry* 2008, 19, 408.

The invention claimed is:

1. A compound of Formula (I)

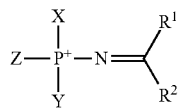

(I)

wherein

Z is selected from —O⁻, —S⁻, —Se⁻, —(N⁻)R$^N$, or a protecting group (PG);

X is selected from the 5'-O— of a nucleoside or oligonucleotide and Y is selected from the 3'-O— of a nucleoside oligonucleotide; —H, —OH, —SH, —NHR$^N$, —O-PG, or —S-PG, wherein PG is a protecting group; a linker, a monophosphate or diphosphate, or a label or quencher;

or

Y is selected from the 3'-O— of a nucleoside or oligonucleotide and X is selected from the 5'-O— of a nucleoside, oligonucleotide, —H, —OH, —SH, —NHR$^N$, —O-PG, or —S-PG, wherein PG is a protecting group; a linker, a monophosphate or diphosphate, or a label or quencher;

$R^1$ is selected from —NR$^{1A}$R$^{1B}$, —OR$^3$, —SR$^3$, —H, —S(O)H, —S(O)R$^3$, —S(O)$_2$H, —S(O)$_2$R$^3$, —S(O)$_2$NH$_2$, —S(O)$_2$NHR$^3$, —S(O)$_2$NR$^3{}_2$, —C$_{1-10}$alkyl, —C$_{2-10}$alkenyl, —C$_{2-10}$alkynyl, or —C$_{6-10}$ aryl;

$R^2$ is selected from —H, —NR$^{2A}$R$^{2B}$, —OR$^3$, —SR$^3$, —CN, —S(O)H, —S(O)R$^3$, —S(O)$_2$H, —S(O)$_2$R$^3$, —S(O)$_2$NH$_2$, —S(O)$_2$NHR$^3$, —S(O)$_2$NR$^3{}_2$, —C$_{1-10}$alkyl, —C$_{2-10}$alkenyl, —C$_{2-10}$alkynyl, or —C$_{6-10}$aryl;

wherein each R$^{1A}$, R$^{1B}$, R$^{2A}$, and R$^{2B}$ is independently selected from —H, —C$_{1-10}$alkyl, —C$_{2-10}$alkenyl, —C$_{2-10}$alkynyl, or —C$_{6-10}$aryl;

optionally, wherein R$^{1A}$ and R$^{2A}$ together form an alkylene chain of 2-4 atoms in length;

optionally, wherein R$^{1A}$ and R$^{1B}$, together with the atom to which they are bound, form a 5-8 membered heterocyclic substituent moiety, selected from the group consisting of N-pyrrolidinyl, N-piperidinyl, N-azepanyl, or N-azocanyl;

optionally, wherein R$^{2A}$ and R$^{2B}$, together with the atom to which they are bound, form a 5-8 membered heterocyclic substituent moiety, selected from the group consisting of N-pyrrolidinyl, N-piperidinyl, N-azepanyl, or N-azocanyl;

$R^3$ is selected from —C$_{1-10}$alkyl, —C$_{2-10}$alkenyl, —C$_{2-10}$alkynyl, or —C$_{6-10}$aryl;

wherein the linker is selected from the group consisting of succinyl, diglycolyl, oxalyl, hydroquinone-O,O'-diacetyl (Q-linker), phthaloyl, 4,5-dichlorophthaloyl, malonyl, glutaryl, diisopropylsilyl and 1,1,3,3-tetraisopropyldisiloxane-1,3-diyl, or dodecane-12-oxy-1-phosphatidyl, the label is fluorescein-derived substituent, the quencher is 2-((2-hydroxy-ethyl)-{4-[2-methoxy-5-methyl-4-(4-methyl-2-nitro-phenylazo)-phenylazo]-phenyl}-amino)-ethanol-derived substituent;

wherein R$^N$ is —H or —C$_{1-4}$alkyl; and when Z is PG, the compound is a salt with anion counterpart selected from the group consisting of I⁻, Br⁻, Cl⁻, N-succinimido ((CH$_2$)$_2$(CO)$_2$N⁻), CCl$_3{}^-$, CBr$_3{}^-$, CI$_3{}^-$, CHI$_2{}^-$, trifluoromethanesulfonate (CF$_3$SO$_3{}^-$), p-toluenesulphonate (C$_7$H$_7$SO$_3{}^-$), dichlorophosphate (PO$_2$Cl$_2{}^-$), perchlorate (ClO$_4{}^-$), tetrafluoroborate (BF$_4{}^-$), tetraphenylborate (BPh$_4{}^-$), or hexafluorophosphate (PF$_6{}^-$).

2. The compound of claim 1, wherein R$^1$ is —NR$^{1A}$R$^{1B}$, —OR$^3$, or —SR$^3$.

3. The compound of claim 1, wherein R$^1$ is NR$^{1A}$R$^{1B}$.

4. The compound of claim 1, wherein R$^2$ is —H, —NR$^{2A}$R$^{2B}$ or —OR$^3$.

5. The compound of claim 1, wherein R$^2$ is —NR$^{2A}$R$^{2B}$.

6. The compound of claim 1, wherein each R$^{1A}$, R$^{1B}$, R$^{2A}$, and R$^{2B}$ is independently selected from —H or —C$_{1-10}$alkyl.

7. The compound of claim 6, wherein each R$^{1A}$, R$^{1B}$, R$^{2A}$, and R$^{2B}$ are each methyl.

8. The compound of claim 1, wherein R$^{1A}$ and R$^{2A}$ together from form an alkylene chain of 2-4 atoms in length and R$^{1B}$ and R$^{2B}$ are each independently selected from —H or —C$_{1-4}$alkyl.

9. The compound of claim 8, wherein $R^{1A}$ and $R^{2A}$ together from —$CH_2$—$CH_2$— and $R^{1B}$ and $R^{2B}$ are each independently selected from —H and methyl.

10. The compound of claim 1, wherein $R^{1A}$ and $R^{1B}$, together with the atom to which they are bound, form a 5-8 membered heterocyclic substituent moiety, selected from the group consisting N pyrrolidinyl, N-piperidinyl, N-azepanyl, or N-azocanyl.

11. The compound of claim 10, wherein $R^{2A}$ and $R^{2B}$, together with the atom to which they are bound, form a 5-8 membered heterocyclic substituent moiety, selected from the group consisting of N-pyrrolidinyl, N-piperidinyl, N-azepanyl, or N-azocanyl.

12. The compound of claim 1, wherein the heterocyclic substituent moiety is a N-pyrrolidinyl.

13. A method of synthesizing the compound according to claim 1, the method comprising reaction of a phosphorous acid derivative of formula

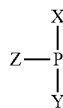

wherein
Z is a protecting group (PG);
X is selected from the 5'-O— of a nucleoside oligonucleotide and Y is selected from the 3'-O— of a nucleoside, oligonucleotide; —H, —OH, —SH, —$NHR^N$, —O-PG, —S-PG, wherein PG is a protecting group; a linker, a monophosphate or diphosphate, or a label or quencher;
or
Y is selected from the 3'-O— of a nucleoside, oligonucleotide and X is selected from the 5'-O— of a nucleoside, oligonucleotide, —H, —OH, —SH, —$NHR^N$, —O-PG, or —S-PG, wherein PG is a protecting group; a linker, a monophosphate or diphosphate, or a label or quencher, with an imino derivative HN=$CR^1R^2$ or an N-silylated derivative $R^{Si}_3SiN$=$CR^1R^2$ in the presence of an oxidant,
wherein
$R^1$ is selected from —$NR^{1A}R^{1B}$, —$OR^3$, —$SR^3$, —H, —S(O)H, —S(O)$R^3$, —S(O)$_2$H, —S(O)$_2R^3$, —S(O)$_2NH_2$, —S(O)$_2NHR^3$, —S(O)$_2NR^3{}_2$, —$C_{1-10}$alkyl, —$C_{2-10}$alkenyl, —$C_{2-10}$alkynyl, or —$C_{6-10}$ aryl;
$R^2$ is selected from —H, —$NR^{2A}R^{2B}$, —$OR^3$, —$SR^3$, CN, —S(O)H, —S(O)$R^3$, —S(O)$_2$H, —S(O)$_2R^3$, —S(O)$_2NH_2$, —S(O)$_2NHR^3$, —S(O)$_2NR^3{}_2$, —$C_{1-10}$alkyl, —$C_{2-10}$alkenyl, —$C_{2-10}$alkynyl, or —$C_{6-10}$ aryl;
wherein each $R^{1A}$, $R^{1B}$, $R^{2A}$, and $R^{2B}$ is independently selected from —H, —$C_{1-10}$alkyl, —$C_{2-10}$alkenyl, —$C_{2-10}$alkynyl, or —$C_{6-10}$aryl;
optionally, wherein $R^{1A}$ and $R^{2A}$ together form an alkylene or heteroalkylene chain of 2-4 atoms in length;
optionally, wherein $R^{1A}$ and $R^{1B}$, together with the atom to which they are bound, form a 5-8 membered heterocyclic substituent moiety, selected from the group consisting of N-pyrrolidinyl, N-piperidinyl, N-azepanyl, or N-azocanyl;
optionally, wherein $R^{2A}$ and $R^{2B}$, together with the atom to which they are bound, form a 5-8 membered heterocyclic substituent moiety, selected from the group consisting of N-pyrrolidinyl, N-piperidinyl, N-azepanyl, or N-azocanyl; and $R^3$ is selected from —$C_{1-10}$alkyl, —$C_{2-10}$alkenyl, —$C_{2-10}$alkynyl, or —$C_{6-10}$aryl,
wherein, $R^{Si}_3$ is an alkyl or aryl group,
wherein the linker is selected from the group consisting of succinyl, diglycolyl, oxalyl, hydroquinone-O,O'-diacetyl (Q-linker), phthaloyl, 4,5-dichlorophthaloyl, malonyl, glutaryl, diisopropylsilyl and 1,1,3,3-tetraisopropyldisiloxane-1,3-diyl, or dodecane-12-oxy-1-phosphatidyl,
the label is fluorescein-derived substituent,
the quencher is 2-((2-hydroxy-ethyl)-{4-[2-methoxy-5-methyl-4-(4-methyl-2-nitro-phenylazo)-phenylazo]-phenyl}-amino)-ethanol-derived substituent; and
wherein $R^N$ is —H, —$C_{1-4}$alkyl.

14. The method of claim 13, wherein the phosphorous acid derivative is a phosphite triester or H-phosphonate diester.

15. The method of claim 13, wherein the oxidant is iodine ($I_2$), bromine ($Br_2$), chlorine ($Cl_2$), iodine chloride (ICl), N-bromosuccinimide, N-chlorosuccinimide, N-iodosuccinimide, carbon tetrachloride ($CCl_4$), bromotrichloromethane ($CCl_3Br$), tetrabromomethane ($CBr_4$), tetraiodomethane ($CI_4$), or iodoform ($CHI_3$).

16. The method of claim 13, wherein the oxidant is iodine ($I_2$).

17. The method of claim 13, further comprising a silylating agent and/or a base.

18. The method of claim 17, wherein the silylating agent is N,O-bis(trimethylsilyl)acetamide (BSA), N,O-bis(trimethylsilyl)trifluoroacetamide (BSTFA), chlorotrimethylsilane, bromotrimethylsilane, iodotrimethylsilane, triethylsilyl chloride, triphenylsilyl chloride, hexamethyldisilazane, trimethylsilyl trifluoromethanesulfonate (TMSOTf), dimethylisopropylsilyl chloride, diethylisopropylsilyl chloride, TERT-butyldimethylsilyl chloride, TERT-butyldiphenylsilyl chloride, triisopropylsilyl chloride, dimethyldichlorosilane or diphenyldichlorosilane.

19. The method of claim 17, wherein the base is triethylamine, N,N-diisopropylethylamine (DIEA), N-methylmorpholine, N-ethylmorpholine, tributylamine, 1,4-diazabicyclo[2.2.2]octane (DABCO), N-methylimidazole (NMI), pyridine, 2,6-lutidine, 2,4,6-collidine, 4-dimethylaminopyridine (DMAP), 1,8-bis(dimethylamino)naphthalene ("proton sponge"), 1,8-diazabicyclo[5.4.0]undec-7-ene (DBU), 1,5-diazabicyclo[4.3.0]non-5-ene (DBN), 1,5,7-triazabicyclo[4.4.0] dec-5-ene (TBD), 7-methyl-1,5,7-triazabicyclo[4.4.0]dec-5-ene (MTBD), 1,1,3,3-tetramethylguanidine (TMG), 2-tert-butyl-1,1,3,3-tetramethylguanidine, 2,8,9-trimethyl-2,5,8,9-tetraaza-1-phosphabicyclo[3.3.3]undecane or a phosphazene base.

20. A method of synthesising a compound of Formula (I), the method comprising reaction of a phosphorous acid derivative of

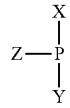

wherein
Z is a protecting group (PG);
X is selected from the 5'-O— of a nucleoside oligonucleotide and Y is selected from the 3'-O— of a nucleoside, oligonucleotide; —H, —OH, —SH, —$NHR^N$, —O-

PG, or —S-PG, wherein PG is a protecting group; a linker, a monophosphate or diphosphate, or a label or quencher;

or

Y is selected from the 3'-O— of a nucleoside, oligonucleotide and X is selected from the 5'-O— of a nucleoside, oligonucleotide, —H, —OH, —SH, —NHR$^N$, —O-PG, or —S-PG, wherein PG is a protecting group; a linker, a monophosphate or diphosphate, or a label or quencher, with an organic azide, wherein the linker is selected from the group consisting of succinyl, diglycolyl, oxalyl, hydroquinone-O,O'-diacetyl (Q-linker), phthaloyl, 4,5-dichlorophthaloyl, malonyl, glutaryl, diisopropylsilyl and 1,1,3,3-tetraisopropyldisiloxane-1,3-diyl, or dodecane-12-oxy-1-phosphatidyl, the label is fluorescein-derived substituent, the quencher is 2-((2-Hydroxy-ethyl)-{4-[2-methoxy-5-methyl-4-(4-methyl-2-nitro-phenylazo)-phenylazo]-phenyl}-amino)-ethanol-derived substituent; and wherein R$^N$ is —H, —C$_{1-4}$alkyl.

21. The method of claim 20, wherein the organic azide comprises of formula:

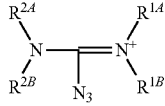

wherein each R$^{1A}$, R$^{1B}$, R$^{2A}$, and R$^{2B}$ is independently —H, —C$_{1-10}$alkyl, —C$_{2-10}$alkenyl, —C$_{2-10}$alkynyl, or —C$_{6-10}$aryl; and/or optionally, wherein R$^{1A}$ and R$^{2B}$ together with the atom to which they are bound, form a 5-8 membered heterocyclic substituent moiety, selected from the group consisting of N-pyrrolidinyl, N-piperidinyl, N-azepanyl, or N-azocanyl; or optionally, wherein R$^{2A}$ and R$^{2B}$, together with the atom to which they are bound, form a 5-8 membered heterocyclic substituent moiety, selected from the group consisting of N-pyrrolidinyl, N-piperidinyl, N-azepanyl, or N-azocanyl;

or

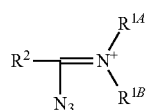

wherein each R$^{1A}$ and R$^{1B}$ is independently —H, —C$_{1-10}$alkyl, —C$_{2-10}$alkenyl, —C$_{2-10}$alkynyl, or —C$_{6-10}$aryl; or R$^{1A}$ and R$^{1B}$, together with the atom to which they are bound, form a 5-8 membered heterocyclic substituent moiety, selected from the group consisting of N-pyrrolidinyl, N-piperidinyl, N-azepanyl, or N-azocanyl, and R$^2$ is selected from —H, —F, —OPG, —Br, —I, —CN, —N$_3$, —O—C$_{1-10}$alkyl, —SPG, and —S—C$_{1-10}$alkyl, wherein PG is a protecting group, wherein the linker is selected from the group consisting of succinyl, diglycolyl, oxalyl, hydroquinone-O,O'-diacetyl (Q-linker), phthaloyl, 4,5-dichlorophthaloyl, malonyl, glutaryl, diisopropylsilyl and 1,1,3,3-tetraisopropyldisiloxane-1,3-diyl, or dodecane-12-oxy-1-phosphatidyl, the label is fluorescein-derived substituent, the quencher is 2-((2-hydroxy-ethyl)-{4-[2-methoxy-5-methyl-4-(4-methyl-2-nitro-phenylazo)-phenylazo]-phenyl}-amino)-ethanol-derived substituent; and wherein R$^N$ is —H, —C$_{1-4}$alkyl.

22. The method of claim 20, further comprising a silylating agent and/or a base.

23. The method of claim 22, wherein the silylating agent is N,O-bis(trimethylsilyl)acetamide (BSA), N,O-bis(trimethylsilyl)trifluoroacetamide (BSTFA), chlorotrimethylsilane, bromotrimethylsilane, iodotrimethylsilane, triethylsilyl chloride, triphenylsilyl chloride, hexamethyldisilazane, trimethylsilyl trifluoromethanesulfonate (TMSOTf), dimethylisopropylsilyl chloride, diethylisopropylsilyl chloride, TERT-butyldimethylsilyl chloride, TERT-butyldiphenylsilyl chloride, triisopropylsilyl chloride, dimethyldichlorosilane or diphenyldichlorosilane.

24. The method of claim 22, wherein the base is triethylamine, N,N-diisopropylethylamine (DIEA), N-methylmorpholine, N-ethylmorpholine, tributylamine, 1,4-diazabicyclo[2.2.2]octane (DABCO), N-methylimidazole (NMI), pyridine, 2,6-lutidine, 2,4,6-collidine, 4-dimethylaminopyridine (DMAP), 1,8-bis(dimethylamino)naphthalene ("proton sponge"), 1,8-diazabicyclo[5.4.0]undec-7-ene (DBU), 1,5-diazabicyclo[4.3.0]non-5-ene (DBN), 1,5,7-triazabicyclo[4.4.0]dec-5-ene (TBD), 7-methyl-1,5,7-triazabicyclo[4.4.0] dec-5-ene (MTBD), 1,1,3,3-tetramethylguanidine (TMG), 2-tert-butyl-1,1,3,3-tetramethylguanidine, 2,8,9-trimethyl-2,5,8,9-tetraaza-1-phosphabicyclo[3.3.3]undecane or a phosphazene base.

25. An oligonucleotide having at least one modified phosphate moiety of formula FVII:

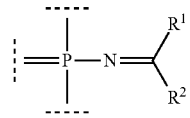

FVII wherein ---- indicates a point of attachment and R$^1$ and R$^2$ are as defined in claim 1.

26. An oligonucleotide wherein a phosphate linking adjacent nucleosides comprises a phosphoryl guanidine, phosphoryl amidine, phosphoryl isourea, phosphoryl isothiourea, phosphoryl imidate, or phosphoryl imidothioate.

* * * * *

UNITED STATES PATENT AND TRADEMARK OFFICE
CERTIFICATE OF CORRECTION

| | |
|---|---|
| PATENT NO. | : 11,208,430 B2 |
| APPLICATION NO. | : 15/329764 |
| DATED | : December 28, 2021 |
| INVENTOR(S) | : Stetsenko et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 134 days.

Signed and Sealed this
Eleventh Day of February, 2025

Coke Morgan Stewart
*Acting Director of the United States Patent and Trademark Office*

SEQUENCE LISTING

<160> NUMBER OF SEQ ID NOS: 24

<210> SEQ ID NO 1
<211> LENGTH: 10
<212> TYPE: DNA

```
<213> ORGANISM: Artificial sequence
<220> FEATURE:
<223> OTHER INFORMATION: Synthetic modified oligonucleotide
<220> FEATURE:
<221> NAME/KEY: misc_feature
<222> LOCATION: (1)..(2)
<223> OTHER INFORMATION: In an embodiment, N,N,N',N'-tetramethyl
      phosphoryl guanidine Group
<220> FEATURE:
<221> NAME/KEY: misc_feature
<222> LOCATION: (2)..(3)
<223> OTHER INFORMATION: In an embodiment, N,N,N',N'-tetramethyl
      phosphoryl guanidine group
<220> FEATURE:
<221> NAME/KEY: misc_feature
<222> LOCATION: (3)..(4)
<223> OTHER INFORMATION: In an embodiment, N,N,N',N'-tetramethyl
      phosphoryl guanidine group
<220> FEATURE:
<221> NAME/KEY: misc_feature
<222> LOCATION: (4)..(5)
<223> OTHER INFORMATION: In an embodiment, N,N,N',N'-tetramethyl
      phosphoryl guanidine group
<220> FEATURE:
<221> NAME/KEY: misc_feature
<222> LOCATION: (5)..(6)
<223> OTHER INFORMATION: In an embodiment, N,N,N',N'-tetramethyl
      phosphoryl guanidine group
<220> FEATURE:
<221> NAME/KEY: misc_feature
<222> LOCATION: (6)..(7)
<223> OTHER INFORMATION: In an embodiment, N,N,N',N'-tetramethyl
      phosphoryl guanidine group
<220> FEATURE:
<221> NAME/KEY: misc_feature
<222> LOCATION: (7)..(8)
<223> OTHER INFORMATION: In an embodiment, N,N,N',N'-tetramethyl
      phosphoryl guanidine group
<220> FEATURE:
<221> NAME/KEY: misc_feature
<222> LOCATION: (8)..(9)
<223> OTHER INFORMATION: In an embodiment, N,N,N',N'-tetramethyl
      phosphoryl guanidine group
<220> FEATURE:
<221> NAME/KEY: misc_feature
<222> LOCATION: (9)..(10)
<223> OTHER INFORMATION: In an embodiment, N,N,N',N'-tetramethyl
      phosphoryl guanidine group
<220> FEATURE:
<221> NAME/KEY: misc_feature
<222> LOCATION: (9)..(10)
<223> OTHER INFORMATION: In an embodiment,
      1,3-dimethyl-2-(phosphorylimino)imidazolidine group
<220> FEATURE:
<221> NAME/KEY: misc_feature
<222> LOCATION: (9)..(10)
<223> OTHER INFORMATION: In an embodiment,
      N,N'-bis(tetramethylene)-N"-phosphoryl guanidine group

<400> SEQUENCE: 1
gcgccaaaca                                                          10

<210> SEQ ID NO 2
<211> LENGTH: 20
<212> TYPE: DNA
<213> ORGANISM: Artificial sequence
<220> FEATURE:
<223> OTHER INFORMATION: Synthetic modified oligonucleotide
<220> FEATURE:
<221> NAME/KEY: misc_feature
<222> LOCATION: (2)..(3)
<223> OTHER INFORMATION: In an embodiment, N,N,N',N'-tetramethyl
      phosphoryl guanidine group
<220> FEATURE:
<221> NAME/KEY: misc_feature
<222> LOCATION: (11)..(12)
<223> OTHER INFORMATION: In an embodiment, N,N,N',N'-tetramethyl
```

```
    phosphoryl guanidine group
<220> FEATURE:
<221> NAME/KEY: misc_feature
<222> LOCATION: (19)..(20)
<223> OTHER INFORMATION: In an embodiment, N,N,N',N'-tetramethyl
      phosphoryl guanidine group
<220> FEATURE:
<221> NAME/KEY: misc_feature
<222> LOCATION: (19)..(20)
<223> OTHER INFORMATION: In an embodiment, phosphoryl guanidine group

<400> SEQUENCE: 2
tttttttttt tttttttttt                                              20

<210> SEQ ID NO 3
<211> LENGTH: 13
<212> TYPE: DNA
<213> ORGANISM: Artificial sequence
<220> FEATURE:
<223> OTHER INFORMATION: Synthetic modified oligonucleotide
<220> FEATURE:
<221> NAME/KEY: misc_feature
<222> LOCATION: (12)..(13)
<223> OTHER INFORMATION: In an embodiment, N,N,N',N'-tetramethyl
      phosphoryl guanidine group

<400> SEQUENCE: 3
ggaaggggag aga                                                     13

<210> SEQ ID NO 4
<211> LENGTH: 16
<212> TYPE: DNA
<213> ORGANISM: Artificial sequence
<220> FEATURE:
<223> OTHER INFORMATION: Synthetic modified oligonucleotide
<220> FEATURE:
<221> NAME/KEY: misc_feature
<222> LOCATION: (16)..(16)
<223> OTHER INFORMATION: Covalently linked to BHQ via an
      N,N,N',N'-tetramethyl phosphoryl guanidine group

<400> SEQUENCE: 4
aacgtcaggg tcttcc                                                  16

<210> SEQ ID NO 5
<211> LENGTH: 15
<212> TYPE: DNA
<213> ORGANISM: Artificial sequence
<220> FEATURE:
<223> OTHER INFORMATION: Synthetic modified oligonucleotide
<220> FEATURE:
<221> NAME/KEY: misc_feature
<222> LOCATION: (1)..(1)
<223> OTHER INFORMATION: Linked to Flu, 5(6)-carboxyfluorescein label
<220> FEATURE:
<221> NAME/KEY: misc_feature
<222> LOCATION: (5)..(6)
<223> OTHER INFORMATION: Linked by 1,12-dodecanediol phosphate
<220> FEATURE:
<221> NAME/KEY: misc_feature
<222> LOCATION: (15)..(15)
<223> OTHER INFORMATION: Covalently linked to BHQ via an
      N,N,N',N'-tetramethyl phosphoryl guanidine group

<400> SEQUENCE: 5
ggaagccctg acgtt                                                   15

<210> SEQ ID NO 6
<211> LENGTH: 12
<212> TYPE: DNA
<213> ORGANISM: Artificial sequence
```

```
<220> FEATURE:
<223> OTHER INFORMATION: Synthetic modified oligonucleotide
<220> FEATURE:
<221> NAME/KEY: misc_feature
<222> LOCATION: (6)..(7)
<223> OTHER INFORMATION: (N,N,N',N'-tetramethyl phosphoryl guanidine
      group) - (2-hydroxymethyl-3-hydroxytetrahydrofurane
      (apurinic/apyrimidinic site) phosphate)
<220> FEATURE:
<221> NAME/KEY: misc_feature
<222> LOCATION: (11)..(12)
<223> OTHER INFORMATION: N,N,N',N'-tetramethyl phosphoryl guanidine
      group

<400> SEQUENCE: 6
tctctccctt cc                                                              12

<210> SEQ ID NO 7
<211> LENGTH: 10
<212> TYPE: RNA
<213> ORGANISM: Artificial sequence
<220> FEATURE:
<223> OTHER INFORMATION: Synthetic modified
      oligo-2'-O-methylribonucleotide
<220> FEATURE:
<221> NAME/KEY: misc_feature
<222> LOCATION: (8)..(9)
<223> OTHER INFORMATION: In an embodiment, N,N,N',N'-tetramethyl
      phosphoryl guanidine group
<220> FEATURE:
<221> NAME/KEY: misc_feature
<222> LOCATION: (9)..(10)
<223> OTHER INFORMATION: In an embodiment, N,N,N',N'-tetramethyl
      phosphoryl guanidine group

<400> SEQUENCE: 7
gcgccaaaca                                                                 10

<210> SEQ ID NO 8
<211> LENGTH: 21
<212> TYPE: RNA
<213> ORGANISM: Artificial sequence
<220> FEATURE:
<223> OTHER INFORMATION: Synthetic modified
      oligo-2'-O-methylribonucleotide
<220> FEATURE:
<221> NAME/KEY: misc_feature
<222> LOCATION: (1)..(2)
<223> OTHER INFORMATION: In the embodiments of Examples 32 & 33,
      phosphorothioate residue
<220> FEATURE:
<221> NAME/KEY: misc_feature
<222> LOCATION: (1)..(1)
<223> OTHER INFORMATION: In the embodiment of Example 33, linked to Flu,
      5(6)-carboxyfluorescein label
<220> FEATURE:
<221> NAME/KEY: misc_feature
<222> LOCATION: (2)..(3)
<223> OTHER INFORMATION: In the embodiments of Examples 32 & 33,
      phosphorothioate residue
<220> FEATURE:
<221> NAME/KEY: misc_feature
<222> LOCATION: (3)..(4)
<223> OTHER INFORMATION: In the embodiments of Examples 32 & 33,
      phosphorothioate residue
<220> FEATURE:
<221> NAME/KEY: misc_feature
<222> LOCATION: (4)..(5)
<223> OTHER INFORMATION: In the embodiments of Examples 32 & 33,
      phosphorothioate residue
<220> FEATURE:
<221> NAME/KEY: misc_feature
<222> LOCATION: (5)..(6)
<223> OTHER INFORMATION: In the embodiments of Examples 32 & 33,
      phosphorothioate residue
```

```
<220> FEATURE:
<221> NAME/KEY: misc_feature
<222> LOCATION: (6)..(7)
<223> OTHER INFORMATION: In the embodiments of Examples 32 & 33,
      phosphorothioate residue
<220> FEATURE:
<221> NAME/KEY: misc_feature
<222> LOCATION: (7)..(8)
<223> OTHER INFORMATION: In the embodiments of Examples 32 & 33,
      phosphorothioate residue
<220> FEATURE:
<221> NAME/KEY: misc_feature
<222> LOCATION: (8)..(9)
<223> OTHER INFORMATION: In the embodiments of Examples 32 & 33,
      phosphorothioate residue
<220> FEATURE:
<221> NAME/KEY: misc_feature
<222> LOCATION: (9)..(10)
<223> OTHER INFORMATION: In the embodiments of Examples 32 & 33,
      phosphorothioate residue
<220> FEATURE:
<221> NAME/KEY: misc_feature
<222> LOCATION: (10)..(11)
<223> OTHER INFORMATION: In the embodiments of Examples 32 & 33,
      phosphorothioate residue
<220> FEATURE:
<221> NAME/KEY: misc_feature
<222> LOCATION: (11)..(12)
<223> OTHER INFORMATION: In the embodiments of Examples 32 & 33,
      phosphorothioate residue
<220> FEATURE:
<221> NAME/KEY: misc_feature
<222> LOCATION: (12)..(13)
<223> OTHER INFORMATION: In the embodiments of Examples 32 & 33,
      phosphorothioate residue
<220> FEATURE:
<221> NAME/KEY: misc_feature
<222> LOCATION: (13)..(14)
<223> OTHER INFORMATION: In the embodiments of Examples 32 & 33,
      phosphorothioate residue
<220> FEATURE:
<221> NAME/KEY: misc_feature
<222> LOCATION: (14)..(15)
<223> OTHER INFORMATION: In the embodiments of Examples 32 & 33,
      phosphorothioate residue
<220> FEATURE:
<221> NAME/KEY: misc_feature
<222> LOCATION: (15)..(16)
<223> OTHER INFORMATION: In the embodiments of Examples 32 & 33,
      phosphorothioate residue
<220> FEATURE:
<221> NAME/KEY: misc_feature
<222> LOCATION: (16)..(17)
<223> OTHER INFORMATION: In the embodiments of Examples 32 & 33,
      phosphorothioate residue
<220> FEATURE:
<221> NAME/KEY: misc_feature
<222> LOCATION: (17)..(18)
<223> OTHER INFORMATION: In the embodiments of Examples 32 & 33,
      phosphorothioate residue
<220> FEATURE:
<221> NAME/KEY: misc_feature
<222> LOCATION: (18)..(19)
<223> OTHER INFORMATION: In the embodiments of Examples 32 & 33,
      phosphorothioate residue
<220> FEATURE:
<221> NAME/KEY: misc_feature
<222> LOCATION: (19)..(20)
<223> OTHER INFORMATION: In the embodiments of Examples 32 & 33,
      N,N,N',N'-tetramethyl phosphoryl guanidine group
<220> FEATURE:
<221> NAME/KEY: misc_feature
<222> LOCATION: (20)..(21)
<223> OTHER INFORMATION: In the embodiments of Examples 32 & 33,
      N,N,N',N'-tetramethyl phosphoryl guanidine group

<400> SEQUENCE: 8
gacauccauu caaauggudu g                                              21
```

```
<210> SEQ ID NO 9
<211> LENGTH: 20
<212> TYPE: RNA
<213> ORGANISM: Artificial sequence
<220> FEATURE:
<223> OTHER INFORMATION: Synthetic modified
      oligo-2'-O-methylribonucleotide
<220> FEATURE:
<221> NAME/KEY: misc_feature
<222> LOCATION: (1)..(1)
<223> OTHER INFORMATION: Linked to Flu, 5(6)-carboxyfluorescein label
<220> FEATURE:
<221> NAME/KEY: misc_feature
<222> LOCATION: (1)..(2)
<223> OTHER INFORMATION: Phosphorothioate residue
<220> FEATURE:
<221> NAME/KEY: misc_feature
<222> LOCATION: (2)..(3)
<223> OTHER INFORMATION: Phosphorothioate residue
<220> FEATURE:
<221> NAME/KEY: misc_feature
<222> LOCATION: (3)..(4)
<223> OTHER INFORMATION: Phosphorothioate residue
<220> FEATURE:
<221> NAME/KEY: misc_feature
<222> LOCATION: (4)..(5)
<223> OTHER INFORMATION: Phosphorothioate residue
<220> FEATURE:
<221> NAME/KEY: misc_feature
<222> LOCATION: (5)..(6)
<223> OTHER INFORMATION: Phosphorothioate residue
<220> FEATURE:
<221> NAME/KEY: misc_feature
<222> LOCATION: (6)..(7)
<223> OTHER INFORMATION: Phosphorothioate residue
<220> FEATURE:
<221> NAME/KEY: misc_feature
<222> LOCATION: (7)..(8)
<223> OTHER INFORMATION: Phosphorothioate residue
<220> FEATURE:
<221> NAME/KEY: misc_feature
<222> LOCATION: (8)..(9)
<223> OTHER INFORMATION: Phosphorothioate residue
<220> FEATURE:
<221> NAME/KEY: misc_feature
<222> LOCATION: (9)..(10)
<223> OTHER INFORMATION: Phosphorothioate residue
<220> FEATURE:
<221> NAME/KEY: misc_feature
<222> LOCATION: (10)..(11)
<223> OTHER INFORMATION: Phosphorothioate residue
<220> FEATURE:
<221> NAME/KEY: misc_feature
<222> LOCATION: (11)..(12)
<223> OTHER INFORMATION: Phosphorothioate residue
<220> FEATURE:
<221> NAME/KEY: misc_feature
<222> LOCATION: (12)..(13)
<223> OTHER INFORMATION: Phosphorothioate residue
<220> FEATURE:
<221> NAME/KEY: misc_feature
<222> LOCATION: (13)..(14)
<223> OTHER INFORMATION: Phosphorothioate residue
<220> FEATURE:
<221> NAME/KEY: misc_feature
<222> LOCATION: (14)..(15)
<223> OTHER INFORMATION: Phosphorothioate residue
<220> FEATURE:
<221> NAME/KEY: misc_feature
<222> LOCATION: (15)..(16)
<223> OTHER INFORMATION: N,N,N',N'-tetramethyl phosphoryl guanidine
      group
<220> FEATURE:
<221> NAME/KEY: misc_feature
<222> LOCATION: (16)..(17)
<223> OTHER INFORMATION: N,N,N',N'-tetramethyl phosphoryl guanidine
      group
```

-continued

```
<220> FEATURE:
<221> NAME/KEY: misc_feature
<222> LOCATION: (17)..(18)
<223> OTHER INFORMATION: N,N,N',N'-tetramethyl phosphoryl guanidine
      group
<220> FEATURE:
<221> NAME/KEY: misc_feature
<222> LOCATION: (18)..(19)
<223> OTHER INFORMATION: N,N,N',N'-tetramethyl phosphoryl guanidine
      group
<220> FEATURE:
<221> NAME/KEY: misc_feature
<222> LOCATION: (19)..(20)
<223> OTHER INFORMATION: N,N,N',N'-tetramethyl phosphoryl guanidine
      group

<400> SEQUENCE: 9
ggccaaaccu ccgcuuaccu                                           20

<210> SEQ ID NO 10
<211> LENGTH: 20
<212> TYPE: RNA
<213> ORGANISM: Artificial sequence
<220> FEATURE:
<223> OTHER INFORMATION: Synthetic mixed
      LNA-oligo-2'-O-methylribonucleotide phosphorothioate
<220> FEATURE:
<221> NAME/KEY: misc_feature
<222> LOCATION: (1)..(1)
<223> OTHER INFORMATION: Linked to Flu, 5(6)-carboxyfluorescein label
<220> FEATURE:
<221> NAME/KEY: misc_feature
<222> LOCATION: (1)..(2)
<223> OTHER INFORMATION: Phosphorothioate residue
<220> FEATURE:
<221> NAME/KEY: misc_feature
<222> LOCATION: (2)..(3)
<223> OTHER INFORMATION: Phosphorothioate residue
<220> FEATURE:
<221> NAME/KEY: misc_feature
<222> LOCATION: (2)..(2)
<223> OTHER INFORMATION: LNA base
<220> FEATURE:
<221> NAME/KEY: misc_feature
<222> LOCATION: (3)..(4)
<223> OTHER INFORMATION: Phosphorothioate residue
<220> FEATURE:
<221> NAME/KEY: misc_feature
<222> LOCATION: (4)..(5)
<223> OTHER INFORMATION: Phosphorothioate residue
<220> FEATURE:
<221> NAME/KEY: misc_feature
<222> LOCATION: (4)..(4)
<223> OTHER INFORMATION: LNA base
<220> FEATURE:
<221> NAME/KEY: misc_feature
<222> LOCATION: (5)..(6)
<223> OTHER INFORMATION: Phosphorothioate residue
<220> FEATURE:
<221> NAME/KEY: misc_feature
<222> LOCATION: (6)..(7)
<223> OTHER INFORMATION: Phosphorothioate residue
<220> FEATURE:
<221> NAME/KEY: misc_feature
<222> LOCATION: (6)..(6)
<223> OTHER INFORMATION: LNA base
<220> FEATURE:
<221> NAME/KEY: misc_feature
<222> LOCATION: (7)..(8)
<223> OTHER INFORMATION: Phosphorothioate residue
<220> FEATURE:
<221> NAME/KEY: misc_feature
<222> LOCATION: (8)..(9)
<223> OTHER INFORMATION: Phosphorothioate residue
<220> FEATURE:
<221> NAME/KEY: misc_feature
<222> LOCATION: (9)..(10)
```

<223> OTHER INFORMATION: Phosphorothioate residue
<220> FEATURE:
<221> NAME/KEY: misc_feature
<222> LOCATION: (9)..(9)
<223> OTHER INFORMATION: LNA base
<220> FEATURE:
<221> NAME/KEY: modified_base
<222> LOCATION: (9)..(9)
<223> OTHER INFORMATION: m5c
<220> FEATURE:
<221> NAME/KEY: misc_feature
<222> LOCATION: (10)..(11)
<223> OTHER INFORMATION: Phosphorothioate residue
<220> FEATURE:
<221> NAME/KEY: misc_feature
<222> LOCATION: (11)..(12)
<223> OTHER INFORMATION: Phosphorothioate residue
<220> FEATURE:
<221> NAME/KEY: misc_feature
<222> LOCATION: (12)..(13)
<223> OTHER INFORMATION: Phosphorothioate residue
<220> FEATURE:
<221> NAME/KEY: misc_feature
<222> LOCATION: (13)..(14)
<223> OTHER INFORMATION: Phosphorothioate residue
<220> FEATURE:
<221> NAME/KEY: misc_feature
<222> LOCATION: (13)..(13)
<223> OTHER INFORMATION: LNA base
<220> FEATURE:
<221> NAME/KEY: modified_base
<222> LOCATION: (13)..(13)
<223> OTHER INFORMATION: m5c
<220> FEATURE:
<221> NAME/KEY: misc_feature
<222> LOCATION: (14)..(15)
<223> OTHER INFORMATION: Phosphorothioate residue
<220> FEATURE:
<221> NAME/KEY: misc_feature
<222> LOCATION: (15)..(16)
<223> OTHER INFORMATION: N,N,N',N'-tetramethyl phosphoryl guanidine
      group
<220> FEATURE:
<221> NAME/KEY: misc_feature
<222> LOCATION: (16)..(17)
<223> OTHER INFORMATION: N,N,N',N'-tetramethyl phosphoryl guanidine
      group
<220> FEATURE:
<221> NAME/KEY: misc_feature
<222> LOCATION: (17)..(17)
<223> OTHER INFORMATION: LNA base
<220> FEATURE:
<221> NAME/KEY: misc_feature
<222> LOCATION: (18)..(19)
<223> OTHER INFORMATION: N,N,N',N'-tetramethyl phosphoryl guanidine
      group
<220> FEATURE:
<221> NAME/KEY: misc_feature
<222> LOCATION: (19)..(20)
<223> OTHER INFORMATION: N,N,N',N'-tetramethyl phosphoryl guanidine
      group

<400> SEQUENCE: 10
ggcgaaaccu ccccuuaccu                                              20

<210> SEQ ID NO 11
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(10)
<223> OTHER INFORMATION: N,N,N',N'-tetramethyl-N"-phosphorylguanidine
      group

```
<400> SEQUENCE: 11
gcgccaaaca                                                          10

<210> SEQ ID NO 12
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(8)
<223> OTHER INFORMATION: N,N,N',N'-tetramethyl-N"-phosphorylguanidine
      group
<220> FEATURE:
<221> NAME/KEY: misc_feature
<222> LOCATION: (8)..(9)
<223> OTHER INFORMATION: N,N,N',N'-tetramethyl-N"-phosphorylguanidine
      group
<220> FEATURE:
<221> NAME/KEY: misc_feature
<222> LOCATION: (9)..(10)
<223> OTHER INFORMATION: N,N,N',N'-tetramethyl-N"-phosphorylguanidine
      group

<400> SEQUENCE: 12
gcgccaaaca                                                          10

<210> SEQ ID NO 13
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (19)..(20)
<223> OTHER INFORMATION: N-phosphorylguanidine group

<400> SEQUENCE: 13
tttttttttt tttttttttt                                               20

<210> SEQ ID NO 14
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(8)
<223> OTHER INFORMATION: N,N,N',N'-tetramethyl phosphoryl guanidine
      group (FVIII)
<220> FEATURE:
<221> NAME/KEY: misc_feature
<222> LOCATION: (9)..(10)
<223> OTHER INFORMATION: N,N,N',N'-tetramethyl phosphoryl guanidine
      group (FVIII)

<400> SEQUENCE: 14
gcgccaaaca                                                          10

<210> SEQ ID NO 15
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(7)
```

```
<223> OTHER INFORMATION: N,N,N',N'-tetramethyl phosphoryl guanidine
      group (FVIII)
<220> FEATURE:
<221> NAME/KEY: misc_feature
<222> LOCATION: (9)..(10)
<223> OTHER INFORMATION: N,N,N',N'-tetramethyl phosphoryl guanidine
      group (FVIII)

<400> SEQUENCE: 15
gcgccaaaca                                                                 10

<210> SEQ ID NO 16
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (19)..(20)
<223> OTHER INFORMATION: N,N,N',N'-tetramethyl phosphoryl guanidine
      group (FVIII)

<400> SEQUENCE: 16
tttttttttt tttttttttt                                                      20

<210> SEQ ID NO 17
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (11)..(12)
<223> OTHER INFORMATION: N,N,N',N'-tetramethyl phosphoryl guanidine
      group (FVIII)

<400> SEQUENCE: 17
tttttttttt tttttttttt                                                      20

<210> SEQ ID NO 18
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(3)
<223> OTHER INFORMATION: N,N,N',N'-tetramethyl phosphoryl guanidine
      group (FVIII).

<400> SEQUENCE: 18
tttttttttt tttttttttt                                                      20

<210> SEQ ID NO 19
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(3)
<223> OTHER INFORMATION: N,N,N',N'-tetramethyl phosphoryl guanidine
      group (FVIII)
<220> FEATURE:
<221> NAME/KEY: misc_feature
<222> LOCATION: (19)..(20)
<223> OTHER INFORMATION: N,N,N',N'-tetramethyl phosphoryl guanidine
``` group (FVIII)

<400> SEQUENCE: 19
tttttttttt tttttttttt					20

<210> SEQ ID NO 20
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(3)
<223> OTHER INFORMATION: N,N,N',N'-tetramethyl phosphoryl guanidine
      group (FVIII)
<220> FEATURE:
<221> NAME/KEY: misc_feature
<222> LOCATION: (11)..(12)
<223> OTHER INFORMATION: N,N,N',N'-tetramethyl phosphoryl guanidine
      group (FVIII)
<220> FEATURE:
<221> NAME/KEY: misc_feature
<222> LOCATION: (19)..(20)
<223> OTHER INFORMATION: N,N,N',N'-tetramethyl phosphoryl guanidine
      group (FVIII)

<400> SEQUENCE: 20
tttttttttt tttttttttt					20

<210> SEQ ID NO 21
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (19)..(20)
<223> OTHER INFORMATION: phosphoryl guanidine group (FIX)

<400> SEQUENCE: 21
tttttttttt tttttttttt					20

<210> SEQ ID NO 22
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(10)
<223> OTHER INFORMATION: 1,3-dimethyl-2-(phosphorylimino)imidazolidine
      group (FXVI).

<400> SEQUENCE: 22 gcgccaaaca					10

<210> SEQ ID NO 23
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(10)
<223> OTHER INFORMATION: N,N'-bis(tetramethylene)-N"-phosphoryl
      guanidine group (FXVII)

```
<400> SEQUENCE: 23
gcgccaaaca                                                          10

<210> SEQ ID NO 24
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(9)
<223> OTHER INFORMATION: N,N,N',N'-tetramethyl phosphoryl guanidine
      group (FVIII)
<220> FEATURE:
<221> NAME/KEY: misc_feature
<222> LOCATION: (9)..(10)
<223> OTHER INFORMATION: N,N,N',N'-tetramethyl phosphoryl guanidine
      group (FVIII)

<400> SEQUENCE: 24
gcgccaaaca                                                          10
```